(12) United States Patent
Kirn et al.

(10) Patent No.: US 11,345,930 B2
(45) Date of Patent: May 31, 2022

(54) CODON OPTIMIZED RPGRORF15 GENES AND USES THEREOF

(71) Applicant: 4D MOLECULAR THERAPEUTICS INC., Emeryville, CA (US)

(72) Inventors: David H. Kirn, Emeryville, CA (US); Melissa A. Kotterman, Emeryville, CA (US); David Schaffer, Emeryville, CA (US); Peter Francis, Emeryville, CA (US)

(73) Assignee: 4D MOLECULAR THERAPEUTICS INC., Emeryville, CA (US)

( * ) Notice: Subject to any disclaimer, the term of this patent is extended or adjusted under 35 U.S.C. 154(b) by 0 days.

(21) Appl. No.: 17/461,716

(22) Filed: Aug. 30, 2021

(65) Prior Publication Data

US 2022/0064673 A1 Mar. 3, 2022

Related U.S. Application Data

(60) Provisional application No. 63/073,843, filed on Sep. 2, 2020.

(51) Int. Cl.
*C12N 15/86* (2006.01)
*A61P 27/02* (2006.01)
*A61K 9/00* (2006.01)
*A61K 48/00* (2006.01)

(52) U.S. Cl.
CPC ............ *C12N 15/86* (2013.01); *A61K 9/0048* (2013.01); *A61K 48/005* (2013.01); *A61P 27/02* (2018.01)

(58) Field of Classification Search
CPC ........ C12N 15/86; A61P 27/02; A61K 9/0048; A61K 48/005
See application file for complete search history.

(56) References Cited

U.S. PATENT DOCUMENTS

| 9,770,491 B2 | 9/2017 | Beltran et al. |
| 10,383,922 B2 | 8/2019 | Beltran et al. |
| 10,836,803 B2 | 11/2020 | MacLaren et al. |

FOREIGN PATENT DOCUMENTS

| WO | 2015/160893 A1 | 10/2015 |
| WO | 2020/061574 A1 | 3/2020 |

OTHER PUBLICATIONS

International Search Report of PCT/US2021/048267 dated Dec. 13, 2021.
Written Opinion of PCT/US2021/048267 dated Dec. 13, 2021.

*Primary Examiner* — Antonio Galisteo Gonzalez
*Assistant Examiner* — Khaleda B Hasan
(74) *Attorney, Agent, or Firm* — Christopher M. Cabral; Much Shelist, PC

(57) ABSTRACT

The present disclosure provides codon optimized RPGRorf15 sequences, vectors, and host cells comprising codon optimized RPGRorf15 sequences, and methods of treating retinal disorders such as XLRP comprising administering to the subject a codon optimized RPGRorf15 sequence.

25 Claims, 22 Drawing Sheets

Specification includes a Sequence Listing.

FIGURE 7

```
                              NarI
                              KasI
ATGAGAGAACCCGAGGAACTGATGCCCGACTCTGGCGCCGTGTTTACCTTCGGCAAGAGC
1 ---------+---------+---------+---------+---------+---------+
TACTCTCTTGGGCTCCTTGACTACGGGCTGAGACCGCGGCACAAATGGAAGCCGTTCTCG
 M   R   E   P   E   E   L   M   P   D   S   G   A   V   F   T   F   G   K   S
 1       3       5       7       9       11      13      15      17      19

AAGTTCGCCGAGAACAACCCCGGCAAGTTCTGGTTCAAGAACGACGTGCCAGTGCACCTG 61 --
      ---------+---------+---------+---------+---------+---------+
      TTCAAGCGGCTCTTGTTGGGGCCGTTCAAGACCAAGTTCTTGCTGCACGGTCACGTGGAC
 K   F   A   E   N   N   P   G   K   F   W   F   K   N   D   V   P   V   H   L
 21      23      25      27      29      31      33      35      37      39

BstEII
AGCTGCGGAGATGAACACTCTGCCGTGGTCACCGGCAACAACAAGCTGTACATGTTCGGC
121 ---------+---------+---------+---------+---------+---------+
    TCGACGCCTCTACTTGTGAGACGGCACCAGTGGCCGTTGTTGTTCGACATGTACAAGCCG
 S   C   G   D   E   H   S   A   V   V   T   G   N   N   K   L   Y   M   F   G
 41      43      45      47      49      51      53      55      57      59

BspMI
AGCAACAACTGGGGCCAGCTCGGCCTGGGATCTAAGTCTGCCATCAGCAAGCCTACCTGC
181 ---------+---------+---------+---------+---------+---------+
    TCGTTGTTGACCCCGGTCGAGCCGGACCCTAGATTCAGACGGTAGTCGTTCGGATGGACG
 S   N   N   W   G   Q   L   G   L   G   S   K   S   A   I   S   K   P   T   C
 61      63      65      67      69      71      73      75      77      79

GTGAAGGCCCTGAAGCCTGAGAAAGTGAAACTGGCCGCCTGCGGCAGAAATCACACCCTG 241 -
      ---------+---------+---------+---------+---------+---------+
      CACTTCCGGGACTTCGGACTCTTTCACTTTGACCGGCGGACGCCGTCTTTAGTGTGGGAC
 V   K   A   L   K   P   E   K   V   K   L   A   A   C   G   R   N   H   T   L
 81      83      85      87      89      91      93      95      97      99

GTTTCTACCGAAGGCGGCAATGTGTATGCCACCGGCGGAAACAATGAGGGACAGCTTGGA 301 -
      ---------+---------+---------+---------+---------+---------+
      CAAAGATGGCTTCCGCCGTTACACATACGGTGGCCGCCTTTGTTACTCCCTGTCGAACCT
 V   S   T   E   G   G   N   V   Y   A   T   G   G   N   N   E   G   Q   L   G
 101     103     105     107     109     111     113     115     117     119
                                      BclI
CTGGGCGACACCGAGGAAAGAAACACCTTCCACGTGATCAGCTTTTTCACCAGCGAGCAC
361 ---------+---------+---------+---------+---------+---------+
    GACCCGCTGTGGCTCCTTTCTTTGTGGAAGGTGCACTAGTCGAAAAGTGGTCGCTCGTG
 L   G   D   T   E   E   R   N   T   F   H   V   I   S   F   F   T   S   E   H
 121     123     125     127     129     131     133     135     137     139

PvuII
AAGATCAAGCAGCTGAGCGCCGGCTCTAATACCTCTGCCGCTCTGACAGAGGACGGCAGA
421 ---------+---------+---------+---------+---------+---------+
    TTCTAGTTCGTCGACTCGCGGCCGAGATTATGGAGACGGCGAGACTGTCTCCTGCCGTCT
 K   I   K   Q   L   S   A   G   S   N   T   S   A   A   L   T   E   D   G   R
 141     143     145     147     149     151     153     155     157     159

CTGTTTATGTGGGGCGACAATTCTGAGGGCCAGATCGGACTGAAGAACGTGTCCAATGTG 481 -
      ---------+---------+---------+---------+---------+---------+
      GACAAATACACCCCGCTGTTAAGACTCCCGGTCTAGCCTGACTTCTTGCACAGGTTACAC
 L   F   M   W   G   D   N   S   E   G   Q   I   G   L   K   N   V   S   N   V
 161     163     165     167     169     171     173     175     177     179
```

FIGURE 7 (cont'd)

```
                                                              PvuII
        TGCGTGCCCCAGCAAGTGACAATCGGCAAGCCTGTGTCTTGGATCAGCTGCGGCTACTAC
  541   ---------+---------+---------+---------+---------+---------+
        ACGCACGGGGTCGTTCACTGTTAGCCGTTCGGACACAGAACCTAGTCGACGCCGATGATG
         C   V   P   Q   Q   V   T   I   G   K   P   V   S   W   I   S   C   G   Y   Y
        181     183     185     187     189     191     193     195     197     199

PflMI
        CACAGCGCCTTTGTGACAACCGATGGCGAGCTGTATGTGTTCGGCGAGCCAGAGAATGGC
  601   ---------+---------+---------+---------+---------+---------+
        GTGTCGCGGAAACACTGTTGGCTACCGCTCGACATACACAAGCCGCTCGGTCTCTTACCG
         H   S   A   F   V   T   T   D   G   E   L   Y   V   F   G   E   P   E   N   G
        201     203     205     207     209     211     213     215     217     219

PvuII
                      PflMI                      PvuII
        AAGCTGGGACTGCCTAACCAGCTGCTGGGCAATCACAGAACCCCTCAGCTGGTGTCTGAG
  661   ---------+---------+---------+---------+---------+---------+
        TTCGACCCTGACGGATTGGTCGACGACCCGTTAGTGTCTTGGGGAGTCGACCACAGACTC
         K   L   G   L   P   N   Q   L   L   G   N   H   R   T   P   Q   L   V   S   E
        221     223     225     227     229     231     233     235     237     239

ATCCCCGAAAAAGTGATCCAGGTGGCCTGTGGCGGAGAGCACACAGTGGTGCTGACAGAG  721 -
        ---------+---------+---------+---------+---------+---------+
        TAGGGGCTTTTTCACTAGGTCCACCGGACACCGCCTCTCGTGTGTCACCACGACTGTCTC
         I   P   E   K   V   I   Q   V   A   C   G   G   E   H   T   V   V   L   T   E
        241     243     245     247     249     251     253     255     257     259

AATGCCGTGTACACCTTTGGCCTGGGCCAGTTTGGACAACTCGGACTGGGAACCTTCCTG  781 -
        ---------+---------+---------+---------+---------+---------+
        TTACGGCACATGTGGAAACCGGACCCGGTCAAACCTGTTGAGCCTGACCCTTGGAAGGAC
         N   A   V   Y   T   F   G   L   G   Q   F   G   Q   L   G   L   G   T   F   L
        261     263     265     267     269     271     273     275     277     279

PvuII
        TTCGAGACAAGCGAGCCCAAAGTGATCGAGAACATCCGGGACCAGACCATCAGCTACATC
  841   ---------+---------+---------+---------+---------+---------+
        AAGCTCTGTTCGCTCGGGTTTCACTAGCTCTTGTAGGCCCTGGTCTGGTAGTCGATGTAG
         F   E   T   S   E   P   K   V   I   E   N   I   R   D   Q   T   I   S   Y   I
        281     283     285     287     289     291     293     295     297     299
                                BclI
        AGCTGTGGCGAGAACCACACAGCCCTGATCACAGACATCGGCCTGATGTACACATTCGGC
  901   ---------+---------+---------+---------+---------+---------+
        TCGACACCGCTCTTGGTGTGTCGGGACTAGTGTCTGTAGCCGGACTACATGTGTAAGCCG
         S   C   G   E   N   H   T   A   L   I   T   D   I   G   L   M   Y   T   F   G
        301     303     305     307     309     311     313     315     317     319

GACGGAAGGCATGGAAAGCTCGGACTTGGCCTGGAAAACTTCACCAACCACTTCATCCCT  961
        ---------+---------+---------+---------+---------+---------+
        CTGCCTTCCGTACCTTTCGAGCCTGAACCGGACCTTTTGAAGTGGTTGGTGAAGTAGGGA
         D   G   R   H   G   K   L   G   L   G   L   E   N   F   T   N   H   F   I   P
        321     323     325     327     329     331     333     335     337     339

PflMI
        ACGCTGTGCAGCAACTTCCTGCGGTTCATTGTGAAGCTGGTGGCCTGCGGAGGATGCCAC
 1021   ---------+---------+---------+---------+---------+---------+
        TGCGACACGTCGTTGAAGGACGCCAAGTAACACTTCGACCACCGGACGCCTCCTACGGTG
         T   L   C   S   N   F   L   R   F   I   V   K   L   V   A   C   G   G   C   H
        341     343     345     347     349     351     353     355     357     359
```

FIGURE 7 (cont'd)

```
          ATGGTGGTTTTTGCTGCCCCTCACAGAGGCGTGGCCAAAGAGATTGAGTTCGACGAGATC
1081 ----------+---------+---------+---------+---------+---------+
          TACCACCAAAAACGACGGGGAGTGTCTCCGCACCGGTTTCTCTAACTCAAGCTGCTCTAG
      M   V   V   F   A   A   P   H   R   G   V   A   K   E   I   E   F   D   E   I
      361 363 365 367 369 371 373 375 377 379

BspMI
          AACGATACCTGCCTGAGCGTGGCCACCTTCCTGCCTTACAGCAGCCTGACATCTGGCAAC
1141 ----------+---------+---------+---------+---------+---------+
          TTGCTATGGACGGACTCGCACCGGTGGAAGGACGGAATGTCGTCGGACTGTAGACCGTTG
      N   D   T   C   L   S   V   A   T   F   L   P   Y   S   S   L   T   S   G   N
      381 383 385 387 389 391 393 395 397 399

PstI
          GTGCTGCAGAGGACACTGAGCGCCAGAATGCGCAGACGGGAAAGAGAGAGAAGCCCCGAC
1201 ----------+---------+---------+---------+---------+---------+
          CACGACGTCTCCTGTGACTCGCGGTCTTACGCGTCTGCCCTTTCTCTCTCTTCGGGGCTG
      V   L   Q   R   T   L   S   A   R   M   R   R   R   E   R   E   R   S   P   D
      401 403 405 407 409 411 413 415 417 419

AGCTTCAGCATGAGAAGAACCCTGCCTCCAATCGAGGGCACACTGGGCCTGTCTGCCTGC
1261 ----------+---------+---------+---------+---------+---------+
          TCGAAGTCGTACTCTTCTTGGGACGGAGGTTAGCTCCCGTGTGACCCGGACAGACGGACG
      S   F   S   M   R   R   T   L   P   P   I   E   G   T   L   G   L   S   A   C
      421 423 425 427 429 431 433 435 437 439

BspMI
          TTTCTGCCTAACAGCGTGTTCCCCAGATGCAGCGAGAGAAACCTGCAAGAGAGCGTGCTG
1321 ----------+---------+---------+---------+---------+---------+
          AAAGACGGATTGTCGCACAAGGGGTCTACGTCGCTCTCTTTGGACGTTCTCTCGCACGAC
      F   L   P   N   S   V   F   P   R   C   S   E   R   N   L   Q   E   S   V   L
      441 443 445 447 449 451 453 455 457 459

BspMI
          AGCGAGCAGGATCTGATGCAGCCTGAGGAACCCGACTACCTGCTGGACGAGATGACCAAA
1381 ----------+---------+---------+---------+---------+---------+
          TCGCTCGTCCTAGACTACGTCGGACTCCTTGGGCTGATGGACGACCTGCTCTACTGGTTT
      S   E   Q   D   L   M   Q   P   E   E   P   D   Y   L   L   D   E   M   T   K
      461 463 465 467 469 471 473 475 477 479

GAGGCCGAGATCGACAACAGCAGCACAGTGGAAAGCCTGGGCGAGACAACCGACATCCTG
1441 ----------+---------+---------+---------+---------+---------+
          CTCCGGCTCTAGCTGTTGTCGTCGTGTCACCTTTCGGACCCGCTCTGTTGGCTGTAGGAC
          E   A   E   I   D   N   S   S   T   V   E   S   L   G   E   T   T   D   I   L
          481 483 485 487 489 491 493 495 497 499

AACATGACCCACATCATGAGCCTGAACAGCAACGAGAAGTCTCTGAAGCTGAGCCCCGTG
1501 ----------+---------+---------+---------+---------+---------+
          TTGTACTGGGTGTAGTACTCGGACTTGTCGTTGCTCTTCAGAGACTTCGACTCGGGGCAC
          N   M   T   H   I   M   S   L   N   S   N   E   K   S   L   K   L   S   P   V
          501 503 505 507 509 511 513 515 517 519

CAGAAGCAGAAGAAGCAGCAGACCATCGGCGAGCTGACACAGGATACTGCCCTGACCGAG
1561 ----------+---------+---------+---------+---------+---------+
          GTCTTCGTCTTCTTCGTCGTCTGGTAGCCGCTCGACTGTGTCCTATGACGGGACTGGCTC
          Q   K   Q   K   K   Q   Q   T   I   G   E   L   T   Q   D   T   A   L   T   E
          521 523 525 527 529 531 533 535 537 539
```

FIGURE 7 (cont'd)

```
                                                         StuI
       AACGACGACAGCGACGAGTACGAAGAGATGAGCGAGATGAAGGAAGGCAAGGCCTGCAAG
1621   ---------+---------+---------+---------+---------+---------+
       TTGCTGCTGTCGCTGCTCATGCTTCTCTACTCGCTCTACTTCCTTCCGTTCCGGACGTTC
        N   D   D   S   D   E   Y   E   E   M   S   E   M   K   E   G   K   A   C   K
       541 543 545 547 549 551 553 555 557 559

StuI
       CAGCACGTGTCCCAGGGCATCTTTATGACCCAGCCTGCCACCACCATCGAGGCCTTTTCC
1681   ---------+---------+---------+---------+---------+---------+
       GTCGTGCACAGGGTCCCGTAGAAATACTGGGTCGGACGGTGGTGGTAGCTCCGGAAAAGG
        Q   H   V   S   Q   G   I   F   M   T   Q   P   A   T   T   I   E   A   F   S
       561 563 565 567 569 571 573 575 577 579

NarI
                                            KasI
       GACGAGGAAGTGGAAATCCCCGAGGAAAAAGAGGGCGCCGAGGACAGCAAAGGCAACGGC
1741   ---------+---------+---------+---------+---------+---------+
       CTGCTCCTTCACCTTTAGGGGCTCCTTTTTCTCCCGCGGCTCCTGTCGTTTCCGTTGCCG
        D   E   E   V   E   I   P   E   E   K   E   G   A   E   D   S   K   G   N   G
       581 583 585 587 589 591 593 595 597 599

ATTGAGGAACAAGAGGTGGAAGCCAACGAAGAGAACGTGAAGGTGCACGGCGGACGGAAA
1801   ---------+---------+---------+---------+---------+---------+
       TAACTCCTTGTTCTCCACCTTCGGTTGCTTCTCTTGCACTTCCACGTGCCGCCTGCCTTT
        I   E   E   Q   E   V   E   A   N   E   E   N   V   K   V   H   G   G   R   K
       601 603 605 607 609 611 613 615 617 619

GAAAAGACCGAGATCCTGAGCGACGACCTGACCGATAAGGCCGAGGTTTCCGAGGGCAAA
1861   ---------+---------+---------+---------+---------+---------+
       CTTTTCTGGCTCTAGGACTCGCTGCTGGACTGGCTATTCCGGCTCCAAAGGCTCCCGTTT
        E   K   T   E   I   L   S   D   D   L   T   D   K   A   E   V   S   E   G   K
       621 623 625 627 629 631 633 635 637 639

SacII
       GCCAAGTCTGTGGGAGAAGCCGAGGATGGACCTGAAGGCCGCGGAGATGGAACCTGTGAA
1921   ---------+---------+---------+---------+---------+---------+
       CGGTTCAGACACCCTCTTCGGCTCCTACCTGGACTTCCGGCGCCTCTACCTTGGACACTT
        A   K   S   V   G   E   A   E   D   G   P   E   G   R   G   D   G   T   C   E
       641 643 645 647 649 651 653 655 657 659

GAAGGATCTAGCGGAGCCGAGCACTGGCAGGATGAGGAACGCGAGAAGGGCGAGAAAGAC
1981   ---------+---------+---------+---------+---------+---------+
       CTTCCTAGATCGCCTCGGCTCGTGACCGTCCTACTCCTTGCGCTCTTCCCGCTCTTTCTG
        E   G   S   S   G   A   E   H   W   Q   D   E   E   R   E   K   G   E   K   D
       661 663 665 667 669 671 673 675 677 679

AAAGGCAGAGGCGAGATGGAAAGACCCGGCGAGGGCGAAAAAGAGCTGGCCGAGAAAGAG
2041   ---------+---------+---------+---------+---------+---------+
       TTTCCGTCTCCGCTCTACCTTTCTGGGCCGCTCCCGCTTTTTCTCGACCGGCTCTTTCTC
        K   G   R   G   E   M   E   R   P   G   E   G   E   K   E   L   A   E   K   E
       681 683 685 687 689 691 693 695 697 699

GAATGGAAGAAACGCGACGGCGAAGAACAAGAGCAGAAAGAAAGAGAGCAGGGCCACCAG
2101   ---------+---------+---------+---------+---------+---------+
       CTTACCTTCTTTGCGCTGCCGCTTCTTGTTCTCGTCTTTCTTTCTCTCGTCCCGGTGGTC
        E   W   K   K   R   D   G   E   E   Q   E   Q   K   E   R   E   Q   G   H   Q
       701 703 705 707 709 711 713 715 717 719
```

FIGURE 7 (cont'd)

```
        AAAGAACGGAATCAAGAGATGGAAGAAGGCGGCGAGGAAGAACACGGCGAAGGGGAAGAA
2161 ---------+---------+---------+---------+---------+---------+
        TTTCTTGCCTTAGTTCTCTACCTTCTTCCGCCGCTCCTTCTTGTGCCGCTTCCCCTTCTT
         K  R  N  Q  E  M  E  E  G  G  E  E  E  H  G  E  G  E  E
        721   723  725  727  729  731  733  735  737  739

GAGGAAGGCGACCGAGAGGAAGAAGAAGAGAAAGAAGGCGAAGGCAAAGAAGAAGGCGAG
2221 ---------+---------+---------+---------+---------+---------+
        CTCCTTCCGCTGGCTCTCCTTCTTCTTCTCTTTCTTCCGCTTCCGTTTCTTCTTCCGCTC
         E  E  G  D  R  E  E  E  E  E  K  E  G  E  G  K  E  E  G  E
        741   743  745  747  749  751  753  755  757  759

GGCGAAGAGGTGGAAGGCGAGCGTGAAAAAGAAGAGGGCGAACGCAAGAAAGAAGAACGC
2281 ---------+---------+---------+---------+---------+---------+
        CCGCTTCTCCACCTTCCGCTCGCACTTTTTCTTCTCCCGCTTGCGTTCTTTCTTCTTGCG
         G  E  E  V  E  G  E  R  E  K  E  E  G  E  R  K  K  E  E  R
        761   763  765  767  769  771  773  775  777  779

GCCGGAAAAGAGGAAAAAGGCGAGGAAGAGGGCGACCAAGGCGAAGGCGAGGAAGAAGAA
2341 ---------+---------+---------+---------+---------+---------+
        CGGCCTTTTCTCCTTTTTCCGCTCCTTCTCCCGCTGGTTCCGCTTCCGCTCCTTCTTCTT
         A  G  K  E  E  K  G  E  E  E  G  D  Q  G  E  G  E  E  E
        781   783  785  787  789  791  793  795  797  799

ACTGAAGGCAGAGGGGAAGAGAAAGAGGAAGGCGGCGAAGTCGAAGGCGGAGAGGTTGAA
2401 ---------+---------+---------+---------+---------+---------+
        TGACTTCCGTCTCCCCTTCTCTTTCTCCTTCCGCCGCTTCAGCTTCCGCCTCTCCAACTT
         T  E  G  R  G  E  E  K  E  E  G  G  E  V  E  G  G  E  V  E
        801   803  805  807  809  811  813  815  817  819

GAAGGCAAAGGCGAGCGAGAAGAGGAAGAAGAAGAAGGCGAAGGCGAGGAAGAGGAAGGC
2461 ---------+---------+---------+---------+---------+---------+
        CTTCCGTTTCCGCTCGCTCTTCTCCTTCTTCTTCTTCCGCTTCCGCTCCTTCTCCTTCCG
         E  G  K  G  E  R  E  E  E  E  E  G  E  G  E  E  E  G
        821   823  825  827  829  831  833  835  837  839

GAAGGCGAAGAGGAAGAAGGCGAAGGGGAAGAAGAAGAAGGCGAAGGCAAGGGCGAAGAG
2521 ---------+---------+---------+---------+---------+---------+
        CTTCCGCTTCTCCTTCTTCCGCTTCCCCTTCTTCTTCTTCCGCTTCCGTTCCCGCTTCTC
         E  G  E  E  E  E  G  E  G  E  E  E  E  G  E  G  K  G  E  E
        841   843  845  847  849  851  853  855  857  859

GAGGGCGAAGAAGGCGAGGGCGAAGAGGAGGGCGAAGAAGGCGAAGGCGAGGGCGAAGAA
2581 ---------+---------+---------+---------+---------+---------+
        CTCCCGCTTCTTCCGCTCCCGCTTCTCCTCCCGCTTCTTCCGCTTCCGCTCCCGCTTCTT
         E  G  E  E  G  E  E  E  G  E  E  G  E  G  E  E
        861   863  865  867  869  871  873  875  877  879

GAAGAAGGCGAAGGCGAAGGCGAGGAAGAAGGCGAAGGCGAAGGGGAAGAAGAGGAAGGC
2641 ---------+---------+---------+---------+---------+---------+
        CTTCTTCCGCTTCCGCTTCCGCTCCTTCTTCCGCTTCCGCTTCCCCTTCTTCTCCTTCCG
         E  E  G  E  G  E  G  E  E  E  G  E  G  E  E  E  E  G
        881   883  885  887  889  891  893  895  897  899

GAAGGCGAAGGCGAAGAAGAAGGCGAAGGCGAGGGCGAAGAGGAAGAAGGCGAAGGCAAA
2701 ---------+---------+---------+---------+---------+---------+
        CTTCCGCTTCCGCTTCTTCTTCCGCTTCCGCTCCCGCTTCTCCTTCTTCCGCTTCCGTTT
         E  G  E  G  E  E  E  G  E  G  E  G  E  E  E  E  G  E  K
        901   903  905  907  909  911  913  915  917  919
```

FIGURE 7 (cont'd)

```
              GGGGAAGAAGAAGGCGAGGAAGGCGAAGGCGAAGGCGAGGAAGAAGAAGGCGAAGGCGAG
2761 ---------+---------+---------+---------+---------+---------+
              CCCCTTCTTCTTCCGCTCCTTCCGCTTCCGCTTCCGCTCCTTCTTCTTCCGCTTCCGCTC
               G   E   E   E   G   E   E   G   E   G   E   G   E   E   E   E   G   E   G   E
              921     923     925     927     929     931     933     935     937     939

GGCGAAGATGGCGAAGGCGAAGGCGAAGAGGAAGAGGGCGAGTGGGAGGGCGAAGAAGAG
2821 ---------+---------+---------+---------+---------+---------+
              CCGCTTCTACCGCTTCCGCTTCCGCTTCTCCTTCTCCCGCTCACCCTCCCGCTTCTTCTC
               G   E   D   G   E   G   E   G   E   E   E   G   E   W   E   G   E   E
              941     943     945     947     949     951     953     955     957     959

GAAGGCGAAGGCGAGGGCGAAGAGGAAGGCGAAGGCGAGGGCGAAGAAGGCGAAGGCGAA
2881 ---------+---------+---------+---------+---------+---------+
              CTTCCGCTTCCGCTCCCGCTTCTCCTTCCGCTTCCGCTCCCGCTTCTTCCGCTTCCGCTT
               E   G   E   G   E   E   E   G   E   G   E   G   E   E   G   E   G   E
              961     963     965     967     969     971     973     975     977     979

GGCGAGGAAGAGGAAGGCGAAGGCGAAGGGGAAGAAGAAGAGGGCGAAGAAGAAGGCGAA
2941 ---------+---------+---------+---------+---------+---------+
              CCGCTCCTTCTCCTTCCGCTTCCGCTTCCCCTTCTTCTTCTCCCGCTTCTTCTTCCGCTT
               G   E   E   E   G   E   G   E   G   E   E   E   E   G   E   E   E   G   E
              981     983     985     987     989     991     993     995     997     999

GAGGAAGGCGAAGGGGAAGAAGAAGGCGAAGGCGAAGGCGAAGAAGAGGAAGAGGGCGAA
3001 ---------+---------+---------+---------+---------+---------+
              CTCCTTCCGCTTCCCCTTCTTCTTCCGCTTCCGCTTCCGCTTCTTCTCCTTCTCCCGCTT
               E   E   G   E   G   E   E   E   G   E   G   E   G   E   E   E   E   G   E
              1001    1003    1005    1007    1009    1011    1013    1015    1017    1019

GTTGAAGGCGAGGTTGAGGGCGAAGAAGGCGAAGGCGAAGGGGAAGAAGAAGAAGGCGAG
3061 ---------+---------+---------+---------+---------+---------+
              CAACTTCCGCTCCAACTCCCGCTTCTTCCGCTTCCGCTTCCCCTTCTTCTTCTTCCGCTC
               V   E   G   E   V   E   G   E   E   G   E   G   E   G   E   E   E   E   G   E
              1021    1023    1025    1027    1029    1031    1033    1035    1037    1039

GAAGAAGGGGAAGAGAGAGAAAAAGAAGGCGAGGGCGAAGAAAACCGCCGGAACCGCGAA
3121 ---------+---------+---------+---------+---------+---------+
              CTTCTTCCCCTTCTCTCTCTTTTTCTTCCGCTCCCGCTTCTTTTGGCGGCCTTGGCGCTT
               E   E   G   E   E   R   E   K   E   G   E   G   E   E   N   R   R   N   R   E
              1041    1043    1045    1047    1049    1051    1053    1055    1057    1059

GAGGAAGAGGAAGAAGAGGGCAAGTACCAAGAGACTGGCGAGGAAGAGAACGAGCGGCAG
3181 ---------+---------+---------+---------+---------+---------+
              CTCCTTCTCCTTCTTCTCCCGTTCATGGTTCTCTGACCGCTCCTTCTCTTGCTCGCCGTC
               E   E   E   E   E   E   G   K   Y   Q   E   T   G   E   E   E   N   E   R   Q
              1061    1063    1065    1067    1069    1071    1073    1075    1077    1079

GATGGCGAAGAGTACAAGAAGGTGTCCAAGATCAAGGGCAGCGTGAAGTACGGCAAGCAC
3241 ---------+---------+---------+---------+---------+---------+
              CTACCGCTTCTCATGTTCTTCCACAGGTTCTAGTTCCCGTCGCACTTCATGCCGTTCGTG
                   D   G   E   E   Y   K   K   V   S   K   I   K   G   S   V   K   Y   G   K   H
              1081    1083    1085    1087    1089    1091    1093    1095    1097    1099

AAGACCTACCAGAAGAAGTCCGTCACCAACACGCAAGGCAATGGAAAAGAACAGCGGAGC
3301 ---------+---------+---------+---------+---------+---------+
              TTCTGGATGGTCTTCTTCAGGCAGTGGTTGTGCGTTCCGTTACCTTTTCTTGTCGCCTCG
                   K   T   Y   Q   K   K   S   V   T   N   T   Q   G   N   G   K   E   Q   R   S
              1101    1103    1105    1107    1109    1111    1113    1115    1117    1119
```

FIGURE 7 (concluded)

```
          AAGATGCCCGTGCAGTCCAAGAGGCTGCTGAAGAATGGCCCTAGCGGCAGCAAGAAATTC
3361 ----------+----------+----------+----------+----------+----------+
          TTCTACGGGCACGTCAGGTTCTCCGACGACTTCTTACCGGGATCGCCGTCGTTCTTTAAG
       K   M   P   V   Q   S   K   R   L   L   K   N   G   P   S   G   S   K   K   F
      1121    1123    1125    1127    1129    1131    1133    1135    1137    1139

XhoI
          TGGAACAATGTGCTGCCCCACTACCTCGAGCTGAAGTGA
3421 ----------+----------+----------+---------
          ACCTTGTTACACGACGGGGTGATGGAGCTCGACTTCACT
       W   N   N   V   L   P   H   Y   L   E   L   K   *
      1141    1143    1145    1147    1149    1151    1153
```

US 11,345,930 B2

CODON OPTIMIZED RPGRORF15 GENES AND USES THEREOF

CROSS-REFERENCE TO RELATED APPLICATIONS

This application claims the benefit of U.S. Provisional Patent Application Ser. No. 63/073,843, filed Sep. 2, 2020, the full disclosure of which is incorporated herein by reference.

SEQUENCE LISTING SUBMISSION VIA EFS-WEB

A computer readable text file, entitled "090400-5012-US-Sequence-Listing" created on or about Aug. 30, 2021, with a file size of about 37,837 bytes contains the sequence listing for this application and is hereby incorporated by reference in its entirety.

BACKGROUND OF THE INVENTION

X-linked retinitis pigmentosa (XLRP) is a relatively severe and genetically heterogenous inherited retinal degeneration. Approximately 70% of XLRP cases are caused by mutations in the Retinitis Pigmentosa GTPase Regulator (RPGR) gene. The RPGR gene encodes several distinct alternatively—spliced transcripts that are widely expressed. The function of the encoded protein is not well understood, but studies suggest that it plays an important role in cell structures called cilia.

One RPGR isoform contains a unique 3' region called ORF15, a Gly- and Glu-rich carboxyl terminal domain of 567 amino acids. This version of the RPGR protein, containing exons 1-13 of the RPGR gene and the ORF15 region, is expressed predominantly in photoreceptors in the retina. Mutations in the ORF15 region of RPGR account for about 60% of all XLRP cases.

Several preclinical studies support the use of wild type cDNA of RPGRorf15 to rescue the XLRP disease phenotype. However, poor sequence stability of the wild type sequence poses challenges to maintaining sequence integrity during vector production and suboptimal expression level of the wild type sequence in human photoreceptors are challenges to gene therapy approaches to treat XLRP.

SUMMARY OF THE INVENTION

Disclosed are codon optimized nucleic acid molecules encoding a human retinitis pigmentosa GTPase regulator (RPGR) protein. In one aspect, the disclosure provides a nucleic acid comprising the nucleotide sequence of SEQ ID NO:1 or a nucleic acid comprising a nucleotide sequence at least 90%, at least 95%, at least 96%, at least 97%, at least 98%, or at least 99% identical to the nucleotide sequence of SEQ ID NO:1 and which encodes a human RPGR polypeptide having the amino acid sequence of SEQ ID NO:2. In some embodiments, a nucleic acid comprising or consisting of the nucleotide sequence of SEQ ID NO:1 is provided. In related embodiments, the nucleic acid is expressed at a higher level compared with the level of expression of a wild type RPGR nucleic acid sequence (e.g. SEQ ID NO:3) in an otherwise identical cell.

In some aspects, a codon optimized nucleic acid molecule as herein described has a human codon adaptation index that is increased relative to that of the wild type RPGR cDNA (GenBank Accession No. NM 001034853; SEQ ID NO:3). In some embodiments, the codon optimized nucleic acid molecule has a human codon adaptation index of at least about 0.85, at least about 0.88, or at least about 0.89.

In certain embodiments, the nucleic acid contains a higher percentage of G/C nucleotides compared to the percentage of G/C nucleotides in SEQ ID NO:3. In other embodiments, the nucleic acid contains a percentage of G/C nucleotides that is at most about 59%, at most about 58%, or at most about 57%. In some aspects, the average G/C content of the nucleic acid is from about 55% to about 59%, from about 56% to about 58%. In some preferred embodiments, the average G/C content is about 57%.

In other embodiments, the nucleic acid comprises one or more optimized parameters relative to SEQ ID NO:3 selected from removal of negative cis-acting sites including without limitation TATA-boxes and splice sites, and increasing the frequency of optimal codons.

In another embodiment, the nucleic acid is operatively linked to at least one transcription control sequence, preferably a transcription control sequence that is heterologous to the nucleic acid. In some aspects, the transcription control sequence is a cell- or tissue-specific promoter that results in cell-specific expression of the nucleic acid e.g. in photoreceptor cells such as human rod photoreceptor-specific human G-protein coupled receptor rhodopsin kinase 1 (hGRK) promoter or a human interphotoreceptor retinoid-binding protein (IRBP) promoter. In preferred embodiments, the transcription control sequence comprises a human rod photoreceptor-specific human G-protein coupled receptor rhodopsin kinase 1 (hGRK) promoter. In other aspects, the transcription control sequence is a constitutive promoter that results in similar expression level of the nucleic acid in many cell types (e.g. a CAG, CBA, CMV, or PGK promoter). In preferred embodiments, the transcription control sequence comprises a human G protein-coupled receptor kinase (hGRK, also known as Rhodopsin Kinase) promoter as described in Young et al., Investigative Ophthalmology and Visual Science, 44(9):4076-4085 (2003). In a particularly preferred embodiment, the hGRK promoter comprises the sequence of SEQ ID NO:4 or comprises a sequence at least 95%, at least 96%, at least 97%, at least 98% or at least 99% identical thereto:

```
                                           (SEQ ID NO: 4)
GGGCCCCAGAAGCCTGGTGGTTGTTTGTCCTTCTCAGGGGAAAAGTGAGG

CGGCCCCTTGGAGGAAGGGGCCGGGCAGAATGATCTAATCGGATTCCAAG

CAGCTCAGGGGATTGTCTTTTTCTAGCACCTTCTTGCCACTCCTAAGCGT

CCTCCGTGACCCCGGCTGGGATTTAGCCTGGTGCTGTGTCAGCCCCGGG
```

In related embodiments, provided herein is an expression cassette comprising a nucleic acid comprising the nucleotide sequence of SEQ ID NO:1, or a nucleotide sequence at least 90% identical thereto, operably linked to an expression control sequence.

In related embodiments, provided herein is a vector comprising a comprising a nucleic acid comprising the nucleotide sequence of SEQ ID NO:1, or a nucleotide sequence at least 90% identical thereto. In preferred embodiments, the vector is a recombinant adeno-associated (rAAV) expression vector. In some embodiments, the rAAV vector comprises a native capsid (e.g. a capsid of AAV serotype 2 or AAV serotype 5 or AAV serotype 8). In other embodiments, the rAAV vector comprises a capsid that is modified (e.g. comprises one or more peptide insertions and/or one or more amino acid substitutions (e.g. tyrosine to phenylalanine) and/or amino acid insertions or amino acid deletions) relative to a native AAV capsid (e.g. comprising one or more modifications relative to an AAV capsid of serotype 2, 5 or 8).

In another embodiment, provided herein is a host cell comprising a nucleic acid comprising the nucleotide sequence of SEQ ID NO:1, or a nucleotide sequence at least 90% identical thereto. In some aspects, the host cell is a mammalian cell, including without limitation, a CHO cell, an HEK293 cell, a HeLa cell, a BHK21 cell, a Vero cell or a V27 cell. In related aspects, the host cell is selected from a CHO cell, an HEK293 cell, an HEK293T cell, a HeLa cell, a BHK21 cell and a Vero cell. In other aspects, the host cell is a photoreceptor cell (e.g. rods; cones), a retinal ganglion cell (RGC), a glial cell (e.g. a Müller glial cell, a microglial cell), a bipolar cell, an amacrine cell, a horizontal cell, or a retinal pigmented epithelium (RPE) cell. In related embodiments, the disclosure provides a method of increasing expression of a polypeptide of SEQ ID NO: 2 comprising culturing the host cell under conditions whereby a polypeptide of SEQ ID NO: 2 is expressed by the nucleic acid molecule, wherein the expression of the polypeptide is increased relative to a host cell cultured under the same conditions comprising a reference nucleic acid comprising the nucleotide sequence of SEQ ID NO:3 (comparator sequence).

In another embodiment, the disclosure provides a method of increasing expression of a polypeptide of SEQ ID NO: 2 in a human subject comprising administering to the subject an isolated nucleic acid molecule comprising a nucleotide sequence at least 85%, at least 90%, at least 95%, at least 96%, at least 97%, at least 98%, or at least 99% identical to the nucleotide sequence of SEQ ID NO:1 and which encodes a polypeptide having the amino acid sequence of SEQ ID NO:2 or a vector comprising such a nucleotide sequence, wherein the expression of the polypeptide is increased relative to a reference nucleic acid molecule comprising the nucleotide sequence of SEQ ID NO:3 (comparator sequence) or a vector comprising the reference nucleic acid molecule.

In some embodiments, the disclosure provides a method of treating an ocular disorder associated with insufficient RGRP ORF15 activity in a human subject comprising administering to the subject a nucleic acid molecule or a vector disclosed herein. In some embodiments, the retinal disorder is X-linked retinitis pigmentosa.

DESCRIPTION OF THE DRAWINGS

FIG. 7 is the codon optimized sequence of SEQ ID NO:1 and the encoded amino acid sequence.

DETAILED DESCRIPTION OF THE INVENTION

Definitions

Figure 1:
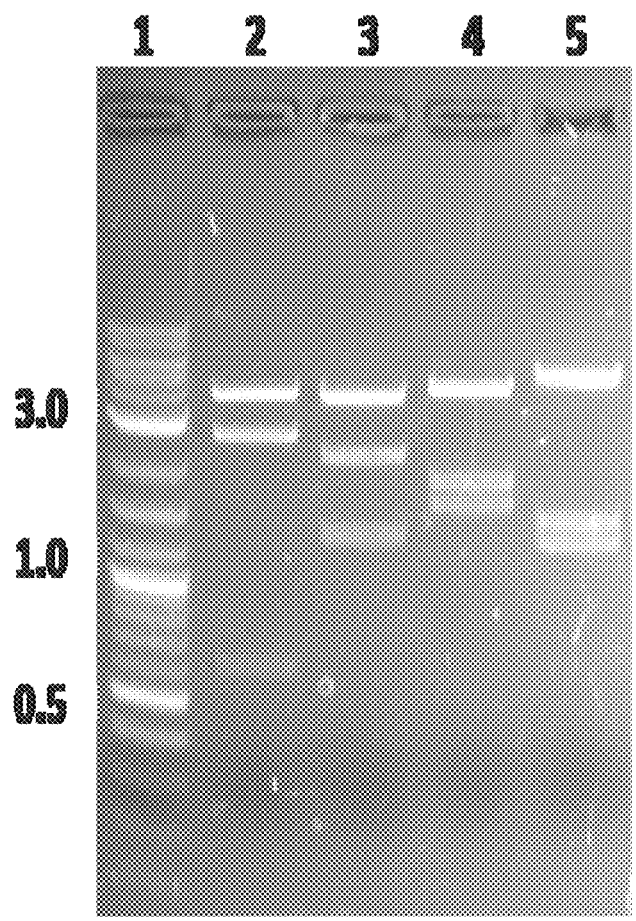
FIG. 1 illustrates gel electrophoresis of restriction digests of pAAV-GRK-cohRPGRorf15-SV40. Maxiprep DNA was digested with various enzymes and analyzed by agarose gel electrophoresis: Lane 1=2-log ladder; Lane 2=BsrGI-H+BglII; Lane 3=Pml+Sph-HF; Lane 4=HindIII-HF+Sph-HF; Lane 5=Pst. The resulting restriction fragments matched the predicted fragments in all digests (Lane 2 fragments of 3.9, 2.5, 0.6 kb; Lane 3 fragments of 3.7, 2.1, 1.3 kb; Lane 4 fragments of 3.9, 1.7 and 1.5 kb; Lane 5 fragments of 4.6, 1.4 and 1.2 kb). The sizes of the prominent 2-log ladder bands in kilobase pairs are indicated to the left of the gel.

A "codon adaptation index," as used herein, refers to a measure of codon usage bias. A codon adaptation index (CAI) measures the deviation of a given protein coding gene sequence with respect to a reference set of genes (Sharp P M and Li W H, Nucleic Acids Res. 15(3):1281-95 (1987)). CAI is calculated by determining the geometric mean of the weight associated to each codon over the length of the gene sequence (measured in codons):

$$CAI = \exp\left(1/L \sum_{i=1}^{L} \ln(w_1(l))\right), \quad (I)$$

For each amino acid, the weight of each of its codons, in CAI, is computed as the ratio between the observed frequency of the codon (fi) and the frequency of the synonymous codon (fj) for that amino acid:

$$w_i = \frac{f_i}{\max(f_j)} = ij \in [\text{synonymous codons for amino acid}] \quad (II)$$

The term "isolated" designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

The term "4D-125" refers to a recombinant AAV particle comprising (i) a capsid protein comprising the amino acid sequence of SEQ ID NO:9 and a heterologous nucleic acid comprising the nucleotide sequence of SEQ ID NO:5.

The term "R100" refers to a variant AAV capsid protein comprising the amino acid sequence of SEQ ID NO:9.

As used herein, a "coding region" or "coding sequence" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions can be present in a single polynucleotide construct, e.g., on a single vector, or in separate polynucleotide constructs, e.g., on separate (different) vectors. It follows, then that a single vector can contain just a single coding region, or comprise two or more coding regions.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

As used herein, the term "nucleic acid" is interchangeable with "polynucleotide" or "nucleic acid molecule" and a polymer of nucleotides is intended.

A polynucleotide which encodes a gene product, e.g., a polypeptide, can include a promoter and/or other transcription or translation control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other transcription control elements, besides a promoter, for example enhancers, operators, repressors, and transcription termination signals, can also be operably associated with a coding region to direct gene product expression.

"Transcriptional control sequences" refer to DNA regulatory sequences, such as promoters, enhancers, terminators, and the like, that provide for the expression of a coding sequence in a host cell. A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit beta-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

A "vector" refers to any vehicle for the cloning of and/or transfer of a nucleic acid into a host cell. A vector can be a replicon to which another nucleic acid segment can be attached so as to bring about the replication of the attached segment. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion, of a polynucleotide into a suitable vector can be accomplished by ligating the appropriate polynucleotide fragments into a chosen vector that has complementary cohesive termini.

Vectors can be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), -galactosidase (LacZ), -glucuronidase (Gus), and the like. Selectable markers can also be considered to be reporters.

Eukaryotic viral vectors that can be used include, but are not limited to, adenovirus vectors, retrovirus vectors, adeno-associated virus vectors, poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

"Promoter" and "promoter sequence" are used interchangeably and refer to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity.

The term "plasmid" refers to an extra-chromosomal element often carrying a gene that is not part of the central metabolism of the cell, and usually in the form of circular double-stranded DNA molecules. Such elements can be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA. Other techniques for alignment are described in Methods in Enzymology, vol. 266: Computer Methods for Macromolecular Sequence Analysis (1996), ed. Doolittle, Academic Press, Inc. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970).

In one embodiment, the present invention provides a modified nucleic acid molecule comprising a nucleotide sequence that encodes a polypeptide of SEQ ID NO:2 (human RGPGR ORF15), wherein the nucleic acid sequence has been codon optimized. In another embodiment, the starting nucleic acid sequence that encodes a polypeptide of SEQ ID NO:2 and that is subject to codon optimization has the nucleotide sequence set forth as SEQ ID NO:3. In preferred embodiments, the sequence that encodes a polypeptide of SEQ ID NO:2 is codon optimized for human expression. SEQ ID NO:1 is a codon optimized version of SEQ ID NO:3, optimized for human expression:

```
                                                         (SEQ ID NO: 1)
ATGAGAGAACCCGAGGAACTGATGCCCGACTCTGGCGCCGTGTTTACCTTCGGCAA

GAGCAAGTTCGCCGAGAACAACCCCGGCAAGTTCTGGTTCAAGAACGACGTGCCA

GTGCACCTGAGCTGCGGAGATGAACACTCTGCCGTGGTCACCGGCAACAACAAGC

TGTACATGTTCGGCAGCAACAACTGGGGCCAGCTCGGCCTGGGATCTAAGTCTGCC

ATCAGCAAGCCTACCTGCGTGAAGGCCCTGAAGCCTGAGAAAGTGAAACTGGCCG

CCTGCGGCAGAAATCACACCCTGGTTTCTACCGAAGGCGGCAATGTGTATGCCACC

GGCGGAAACAATGAGGGACAGCTTGGACTGGGCGACACCGAGGAAAGAAACACC

TTCCACGTGATCAGCTTTTTCACCAGCGAGCACAAGATCAAGCAGCTGAGCGCCGG

CTCTAATACCTCTGCCGCTCTGACAGAGGACGGCAGACTGTTTATGTGGGGCGACA

ATTCTGAGGGCCAGATCGGACTGAAGAACGTGTCCAATGTGTGCGTGCCCCAGCA

AGTGACAATCGGCAAGCCTGTGTCTTGGATCAGCTGCGGCTACTACCACAGCGCCT

TTGTGACAACCGATGGCGAGCTGTATGTGTTCGGCGAGCCAGAGAATGGCAAGCT

GGGACTGCCTAACCAGCTGCTGGGCAATCACAGAACCCCTCAGCTGGTGTCTGAGA

TCCCCGAAAAAGTGATCCAGGTGGCCTGTGGCGGAGAGCACACAGTGGTGCTGAC

AGAGAATGCCGTGTACACCTTTGGCCTGGGCCAGTTTGGACAACTCGGACTGGGAA

CCTTCCTGTTCGAGACAAGCGAGCCCAAAGTGATCGAGAACATCCGGGACCAGAC

CATCAGCTACATCAGCTGTGGCGAGAACCACACAGCCCTGATCACAGACATCGGC

CTGATGTACACATTCGGCGACGGAAGGCATGGAAAGCTCGGACTTGGCCTGGAAA

ACTTCACCAACCACTTCATCCCTACGCTGTGCAGCAACTTCCTGCGGTTCATTGTGA

AGCTGGTGGCCTGCGGAGGATGCCACATGGTGGTTTTTGCTGCCCCTCACAGAGGC

GTGGCCAAAGAGATTGAGTTCGACGAGATCAACGATACCTGCCTGAGCGTGGCCA

CCTTCCTGCCTTACAGCAGCCTGACATCTGGCAACGTGCTGCAGAGGACACTGAGC

GCCAGAATGCGCAGACGGGAAAGAGAGAGAAGCCCCGACAGCTTCAGCATGAGA

AGAACCCTGCCTCCAATCGAGGGCACACTGGGCCTGTCTGCCTGCTTTCTGCCTAA

CAGCGTGTTCCCCAGATGCAGCGAGAGAAACCTGCAAGAGAGCGTGCTGAGCGAG

CAGGATCTGATGCAGCCTGAGGAACCCGACTACCTGCTGGACGAGATGACCAAAG

AGGCCGAGATCGACAACAGCAGCACAGTGGAAAGCCTGGGCGAGACAACCGACA

TCCTGAACATGACCCACATCATGAGCCTGAACAGCAACGAGAAGTCTCTGAAGCT

GAGCCCCGTGCAGAAGCAGAAGAAGCAGCAGACCATCGGCGAGCTGACACAGGA

TACTGCCCTGACCGAGAACGACGACAGCGACGAGTACGAAGAGATGAGCGAGATG

AAGGAAGGCAAGGCCTGCAAGCAGCACGTGTCCCAGGGCATCTTTATGACCCAGC

CTGCCACCACCATCGAGGCCTTTTCCGACGAGGAAGTGGAAATCCCCGAGGAAAA

AGAGGGCGCCGAGGACAGCAAAGGCAACGGCATTGAGGAACAAGAGGTGGAAGC

CAACGAAGAGAACGTGAAGGTGCACGGCGGACGGAAAGAAAAGACCGAGATCCT
```

-continued
```
GAGCGACGACCTGACCGATAAGGCCGAGGTTTCCGAGGGCAAAGCCAAGTCTGTG

GGAGAAGCCGAGGATGGACCTGAAGGCCGCGGAGATGGAACCTGTGAAGAAGGA

TCTAGCGGAGCCGAGCACTGGCAGGATGAGGAACGCGAGAAGGGCGAGAAAGAC

AAAGGCAGAGGCGAGATGGAAAGACCCGGCGAGGGCGAAAAAGAGCTGGCCGAG

AAAGAGGAATGGAAGAAACGCGACGGCGAAGAACAAGAGCAGAAAGAAAGAGA

GCAGGGCCACCAGAAAGAACGGAATCAAGAGATGGAAGAAGGCGGCGAGGAAGA

ACACGGCGAAGGGGAAGAAGAGGAAGGCGACCGAGAGGAAGAAGAAGAGAAAG

AAGGCGAAGGCAAAGAAGAAGGCGAGGGCGAAGAGGTGGAAGGCGAGCGTGAA

AAAGAAGAGGGCGAACGCAAGAAAGAAGAACGCGCCGGAAAAGAGGAAAAAGG

CGAGGAAGAGGGCGACCAAGGCGAAGGCGAGGAAGAAGAAACTGAAGGCAGAG

GGGAAGAGAAAGAGGAAGGCGGCGAAGTCGAAGGCGGAGAGGTTGAAGAAGGCA

AAGGCGAGCGAGAAGAGGAAGAAGAAGAAGGCGAAGGCGAGGAAGAGGAAGGC

GAAGGCGAAGAGGAAGAAGGCGAAGGGGAAGAAGAAGAAGGCGAAGGCAAGGG

CGAAGAGGAGGGCGAAGAAGGCGAGGGCGAAGAGGAGGGCGAAGAAGGCGAAG

GCGAGGGCGAAGAAGAAGAAGGCGAAGGCGAAGGCGAGGAAGAAGGCGAAGGC

GAAGGGGAAGAAGAGGAAGGCGAAGGCGAAGGCGAAGAAGAAGGCGAAGGCGA

GGGCGAAGAGGAAGAAGGCGAAGGCAAAGGGGAAGAAGAAGGCGAGGAAGGCG

AAGGCGAAGGCGAGGAAGAAGAAGGCGAAGGCGAGGGCGAAGATGGCGAAGGC

GAAGGCGAAGAGGAAGAGGGCGAGTGGGAGGGCGAAGAAGAGGAAGGCGAAGG

CGAGGGCGAAGAGGAAGGCGAAGGCGAGGGCGAAGAAGGCGAAGGCGAAGGCG

AGGAAGAGGAAGGCGAAGGCGAAGGGGAAGAAGAAGAGGGCGAAGAAGAAGGC

GAAGAGGAAGGCGAAGGGGAAGAAGAAGGCGAAGGCGAAGGCGAAGAAGAGGA

AGAGGGCGAAGTTGAAGGCGAGGTTGAGGGCGAAGAAGGCGAAGGCGAAGGGGA

AGAAGAAGGCGAGGAAGAAGGGGAAGAGAGAGAAAAAGAAGGCGAGGGCG

AAGAAACCGCCGGAACCGCGAAGAGGAAGAGGAAGAAGAGGGCAAGTACCAAG

AGACTGGCGAGGAAGAGAACGAGCGGCAGGATGGCGAAGAGTACAAGAAGGTGT

CCAAGATCAAGGGCAGCGTGAAGTACGGCAAGCACAAGACCTACCAGAAGAAGTC

CGTCACCAACACGCAAGGCAATGGAAAAGAACAGCGGAGCAAGATGCCCGTGCA

GTCCAAGAGGCTGCTGAAGAATGGCCCTAGCGGCAGCAAGAAATTCTGGAACAAT

GTGCTGCCCCACTACCTCGAGCTGAAGTGA
```

In some embodiments, a codon-optimized sequence encoding human RPGR ORF15 is provided lacking the TGA stop codon of SEQ ID NO:1 (i.e. consisting of nucleotides 1-3456 of SEQ ID NO:1).

In one aspect, the disclosure provides a polynucleotide comprising the nucleotide sequence of SEQ ID NO:1 or polynucleotide comprising a nucleotide sequence at least 90%, at least 95%, at least 96%, at least 97%, at least 98%, or at least 99% identical to the nucleotide sequence of SEQ ID NO:1 and which encodes a human RPGR polypeptide having the amino acid sequence of SEQ ID NO:2:

```
                                              (SEQ ID NO: 2)
MREPEELMPDSGAVFTFGKSKFAENNPGKFWFKNDVPVHLSCGDEHSAVV

TGNNKLYMFGSNNWGQLGLGSKSAISKPTCVKALKPEKVKLAACGRNHTL
```
-continued
```
VSTEGGNVYATGGNNEGQLGLGDTEERNTFHVISFFTSEHKIKQLSAGSN

TSAALTEDGRLFMWGDNSEGQIGLKNVSNVCVPQQVTIGKPVSWISCGYY

HSAFVTTDGELYVFGEPENGKLGLPNQLLGNHRTPQLVSEIPEKVIQVAC

GGEHTVVLTENAVYTFGLGQFGQLGLGTFLFETSEPKVIENIRDQTISYI

SCGENHTALITDIGLMYTFGDGRHGKLGLGLENFTNHFIPTLCSNFLRFI

VKLVACGGCHMVVFAAPHRGVAKEIEFDEINDTCLSVATFLPYSSLTSGN

VLQRTLSARMRRRERERSPDSFSMRRTLPPIEGTLGLSACFLPNSVFPRC

SERNLQESVLSEQDLMQPEEPDYLLDEMTKEAEIDNSSTVESLGETTDIL

NMTHIMSLNSNEKSLKLSPVQKQKKQQTIGELTQDTALTENDDSDEYEEM
```

-continued

SEMKEGKACKQHVSQGIFMTQPATTIEAFSDEEVEIPEEKEGAEDSKGNG

IEEQEVEANEENVKVHGGRKEKTEILSDDLTDKAEVSEGKAKSVGEAEDG

PEGRGDGTCEEGSSGAEHWQDEEREKGEKDKGRGEMERPGEGEKELAEKE

EWKKRDGEEQEQKEREQGHQKERNQEMEEGGEEEHGEGEEEEGDREEEEE

KEGEGKEEGEGEEVEGEREKEEGERKKEERAGKEEKGEEEGDQGEGEEEE

TEGRGEEKEEGGEVEGGEVEEGKGEREEEEEGEGEEEEGEGEEEEGEGE

EEEGEGKGEEEGEEGEGEEEGEEGEGEGEEEEGEGEGEEEGEGEGEEEG

EGEGEEEGEGEGEEEEGEGKGEEEGEGEGEEEEGEGEGEDGEGEGEE

EEGEWEGEEEEGEGEGEEEGEGEGEEGEGEGEEEEGEGEGEEEEGEEEGE

EEGEGEEEGEGEGEEEEEGEVEGEVEGEEGEGEGEEEEGEEEGEEREKEG

EGEENRRNREEEEEEEGKYQETGEEEENERQDGEEYKKVSKIKGSVKYGKH

KTYQKKSVTNTQGNGKEQRSKMPVQSKRLLKNGPSGSKKFWNNVLPHYLE

LK

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprises the codons encoding the amino acids of, any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

| | | T | C | A | G |
|---|---|---|---|---|---|
| T | | TTT Phe (F) | TCT Ser (S) | TAT Tyr (Y) | TGT Cys (C) |
| | | TTC | TCC | TAC" | TGC |
| | | TTA Leu (L) | TCA | TAA Stop | TGA Stop |
| | | TTG | TCG | TAG Stop | TGG Trp (W) |
| C | | CAT Leu (L) | CCT Pro (P) | CAT His (H) | CGT Arg (R) |
| | | CTC | CCC | CAC | CGC |
| | | CTA | CCA | CAA Gln (Q) | CGA |
| | | CTG | CCG | CAG | CGG |
| A | | ATT Ile (I) | ACT Thr (T) | AAT Asn (N) | AGT Ser (S) |
| | | ATC | ACC | AAC | AGC |
| | | ATA | ACA | AAA Lys (K) | AGA Arg (R) |
| | | ATG Met (M) | ACG | AAG | AGG |

TABLE 1-continued

The Standard Genetic Code

| | T | C | A | G |
|---|---|---|---|---|
| G | GTT (Val) V | GCT Ala (A) | GAT Asp (D | GGT Gly (G) |
| | GTC | GCC | GAC | GGC |
| | GTA | GCA | GAA Glu (E) | GGA |
| | GTG | GCG | GAG | GGG |

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, the relative frequencies of codon usage have been calculated. Codon usage tables are available, for example, at the "Codon Usage Database" available at www.kazusa.or.jp/codon/(visited Jun. 18, 2012). See Nakamura, Y., et al. Nucl. Acids Res. 28:292 (2000).

Randomly assigning codons at an optimized frequency to encode a given polypeptide sequence can be done manually by calculating codon frequencies for each amino acid, and then assigning the codons to the polypeptide sequence randomly. Additionally, various algorithms and computer software programs can be used to calculate an optimal sequence.

Non-Viral Vectors

In some embodiments, a non-viral vector (e.g. an expression plasmid) comprising a modified nucleic acid as herein described is provided. Preferably, the non-viral vector is a plasmid comprising a nucleic acid sequence of SEQ ID NO: 1, or a sequence at least 90% identical thereto.

Viral Vectors

In preferred embodiments, a viral vector comprising a modified (codon optimized) nucleic acid as herein described is provided. Preferably, the viral vector comprises a nucleic acid sequence of SEQ ID NO: 1, or a sequence at least 90% identical thereto, operably linked to an expression control sequence. Examples of suitable viral vectors include but are not limited to adenoviral, retroviral, lentiviral, herpesvirus and adeno-associated virus (AAV) vectors.

In a preferred embodiment, the viral vector includes a portion of a parvovirus genome, such as an AAV genome with the rep and cap genes deleted and/or replaced by the modified RPGRorf15 gene sequence and its associated expression control sequences. The modified human RPGRorf15 gene sequence is typically inserted adjacent to one or two (i.e., is flanked by) AAV TRs or TR elements adequate for viral replication (Xiao et al., 1997, J. Virol. 71(2): 941-948), in place of the nucleic acid encoding viral rep and cap proteins. Other regulatory sequences suitable for use in facilitating tissue-specific expression of the modified RPGRorf15 gene sequence in the target cell may also be included.

In some preferred embodiments, the AAV viral vector comprises a nucleic acid comprising from 5' to 3': (a) an AAV2 terminal repeat (b) an hGRK promoter (c) a codon optimized RPGRorf15 gene as herein described (d) a polyadenylation sequence and (e) an AAV2 terminal repeat. In a particularly preferred embodiment, the AAV viral vector comprises a nucleic acid (transgene cassette) comprising the sequence of SEQ ID NO:5 or a sequence at least 90%, at least 95%, at least 98% or at least 99% identical thereto:

```
                                                          (SEQ ID NO: 5)
TTGGCCACTC CCTCTCTGCG CGCTCGCTCG CTCACTGAGG CCGGGCGACC AAAGGTCGCC     60

CGACGCCCGG GCTTTGCCCG GGCGGCCTCA GTGAGCGAGC GAGCGCGCAG AGAGGGAGTG    120

GCCAACTCCA TCACTAGGGG TTCCTATCGA TTGAATTCCC CGGGGATCCG GGCCCCAGAA    180

GCCTGGTGGT TGTTTGTCCT TCTCAGGGGA AAAGTGAGGC GGCCCCTTGG AGGAAGGGGC    240

CGGGCAGAAT GATCTAATCG GATTCCAAGC AGCTCAGGGG ATTGTCTTTT TCTAGCACCT    300

TCTTGCCACT CCTAAGCGTC CTCCGTGACC CCGGCTGGGA TTTAGCCTGG TGCTGTGTCA    360

GCCCCGGGTC TAGAGTCGAC CTGCAGAAGC TTCCACCATG AGAGAACCCG AGGAACTGAT    420

GCCCGACTCT GGCGCCGTGT TTACCTTCGG CAAGAGCAAG TTCGCCGAGA CAACCCCGG    480

CAAGTTCTGG TTCAAGAACG ACGTGCCAGT GCACCTGAGC TGCGGAGATG AACACTCTGC    540

CGTGGTCACC GGCAACAACA AGCTGTACAT GTTCGGCAGC AACAACTGGG GCCAGCTCGG    600

CCTGGGATCT AAGTCTGCCA TCAGCAAGCC TACCTGCGTG AAGGCCCTGA AGCCTGAGAA    660

AGTGAAACTG GCCGCCTGCG GCAGAAATCA CACCCTGGTT CTACCGAAG GCGGCAATGT    720

GTATGCCACC GGCGGAAACA ATGAGGGACA GCTTGGACTG GGCGACACCG AGGAAAGAAA    780

CACCTTCCAC GTGATCAGCT TTTTCACCAG CGAGCACAAG ATCAAGCAGC TGAGCGCCGG    840

CTCTAATACC TCTGCCGCTC TGACAGAGGA CGGCAGACTG TTTATGTGGG GCGACAATTC    900

TGAGGGCCAG ATCGGACTGA AGAACGTGTC CAATGTGTGC GTGCCCCAGC AAGTGACAAT    960

CGGCAAGCCT GTGTCTTGGA TCAGCTGCGG CTACTACCAC AGCGCCTTTG TGACAACCGA   1020

TGGCGAGCTG TATGTGTTCG GCGAGCCAGA GAATGGCAAG CTGGGACTGC CTAACCAGCT   1080

GCTGGGCAAT CACAGAACCC CTCAGCTGGT GTCTGAGATC CCCGAAAAAG TGATCCAGGT   1140

GGCCTGTGGC GGAGAGCACA CAGTGGTGCT GACAGAGAAT GCCGTGTACA CCTTTGGCCT   1200

GGGCCAGTTT GGACAACTCG GACTGGGAAC CTTCCTGTTC GAGACAAGCG AGCCCAAAGT   1260

GATCGAGAAC ATCCGGGACC AGACCATCAG CTACATCAGC TGTGGCGAGA ACCACACAGC   1320

CCTGATCACA GACATCGGCC TGATGTACAC ATTCGGCGAC GGAAGGCATG AAAGCTCGG   1380

ACTTGGCCTG GAAAACTTCA CCAACCACTT CATCCCTACG CTGTGCAGCA ACTTCCTGCG   1440

GTTCATTGTG AAGCTGGTGG CCTGCGGAGG ATGCCACATG GTGGTTTTTG CTGCCCCTCA   1500

CAGAGGCGTG GCCAAAGAGA TTGAGTTCGA CGAGATCAAC GATACCTGCC TGAGCGTGGC   1560

CACCTTCCTG CCTTACAGCA GCCTGACATC TGGCAACGTG CTGCAGAGGA CACTGAGCGC   1620

CAGAATGCGC AGACGGGAAA GAGAGAGAAG CCCCGACAGC TTCAGCATGA AAGAACCCT   1680

GCCTCCAATC GAGGGCACAC TGGGCCTGTC TGCCTGCTTT CTGCCTAACA GCGTGTTCCC   1740

CAGATGCAGC GAGAGAAACC TGCAAGAGAG CGTGCTGAGC GAGCAGGATC TGATGCAGCC   1800

TGAGGAACCC GACTACCTGC TGGACGAGAT GACCAAAGAG GCCGAGATCG ACAACAGCAG   1860

CACAGTGGAA AGCCTGGGCG AGACAACCGA CATCCTGAAC ATGACCCACA TCATGAGCCT   1920

GAACAGCAAC GAGAAGTCTC TGAAGCTGAG CCCCGTGCAG AAGCAGAAGA AGCAGCAGAC   1980

CATCGGCGAG CTGACACAGG ATACTGCCCT GACCGAGAAC GACGACAGCG ACGAGTACGA   2040

AGAGATGAGC GAGATGAAGG AAGGCAAGGC CTGCAAGCAG CACGTGTCCC AGGGCATCTT   2100

TATGACCCAG CCTGCCACCA CCATCGAGGC CTTTTCCGAC GAGGAAGTGG AAATCCCCGA   2160

GGAAAAAGAG GGCGCCGAGG ACAGCAAAGG CAACGGCATT GAGGAACAAG AGGTGGAAGC   2220

CAACGAAGAG AACGTGAAGG TGCACGGCGG ACGGAAAGAA AAGACCGAGA TCCTGAGCGA   2280
```

```
CGACCTGACC GATAAGGCCG AGGTTTCCGA GGGCAAAGCC AAGTCTGTGG GAGAAGCCGA    2340

GGATGGACCT GAAGGCCGCG GAGATGGAAC CTGTGAAGAA GGATCTAGCG GAGCCGAGCA    2400

CTGGCAGGAT GAGGAACGCG AGAAGGGCGA GAAAGACAAA GGCAGAGGCG AGATGGAAAG    2460

ACCCGGCGAG GGCGAAAAAG AGCTGGCCGA GAAAGAGGAA TGGAAGAAAC GCGACGGCGA    2520

AGAACAAGAG CAGAAAGAAA GAGAGCAGGG CCACCAGAAA GAACGGAATC AAGAGATGGA    2580

AGAAGGCGGC GAGGAAGAAC ACGGCGAAGG GGAAGAAGAG GAAGGCGACC GAGAGGAAGA    2640

AGAAGAGAAA GAAGGCGAAG GCAAAGAAGA AGGCGAGGGC GAAGAGGTGG AAGGCGAGCG    2700

TGAAAAAGAA GAGGGCGAAC GCAAGAAAGA AGAACGCGCC GGAAAAGAGG AAAAAGGCGA    2760

GGAAGAGGGC GACCAAGGCG AAGGCGAGGA AGAAGAAACT GAAGGCAGAG GGGAAGAGAA    2820

AGAGGAAGGC GGCGAAGTCG AAGGCGGAGA GGTTGAAGAA GGCAAAGGCG AGCGAGAAGA    2880

GGAAGAAGAA GAAGGCGAAG GCGAGGAAGA GGAAGGCGAA GGCGAAGAGG AAGAAGGCGA    2940

AGGGGAAGAA GAAGAAGGCG AAGGCAAGGG CGAAGAGGAG GGCGAAGAAG GCGAGGGCGA    3000

AGAGGAGGGC GAAGAAGGCG AAGGCGAGGG CGAAGAAGAA GAAGGCGAAG GCGAAGGCGA    3060

GGAAGAAGGC GAAGGCGAAG GGAAGAAGAA GGAAGGCGAA GGCGAAGGCG AAGAAGAAGG    3120

CGAAGGCGAG GGCGAAGAGG AAGAAGGCGA AGGCAAAGGG GAAGAAGAAG GCGAGGAAGG    3180

CGAAGGCGAA GGCGAGGAAG AAGAAGGCGA AGGCGAGGGC GAAGATGGCG AAGGCGAAGG    3240

CGAAGAGGAA GAGGGCGAGT GGGAGGGCGA AGAAGAGGAA GGCGAAGGCG AGGGCGAAGA    3300

GGAAGGCGAA GGCGAGGGCG AAGAAGGCGA AGGCGAAGGC GAGGAAGAGG AAGGCGAAGG    3360

CGAAGGGGAA GAAGAAGAGG GCGAAGAAGA AGGCGAAGAG GAAGGCGAAG GGAAGAAGAA    3420

AGGCGAAGGC GAAGGCGAAG AAGAGGAAGA GGGCGAAGTT GAAGGCGAGG TTGAGGGCGA    3480

AGAAGGCGAA GGCGAAGGGG AAGAAGAAGA AGGCGAGGAA GAAGGGGAAG AGAGAGAAAA    3540

AGAAGGCGAG GGCGAAGAAA CCGCCGGAAC CGCGAAGAGG AAGAGGAAG AAGAGGGCAA     3600

GTACCAAGAG ACTGGCGAGG AAGAGAACGA GCGGCAGGAT GGCGAAGAGT ACAAGAAGGT    3660

GTCCAAGATC AAGGGCAGCG TGAAGTACGG CAAGCACAAG ACCTACCAGA GAAGTCCGT     3720

CACCAACACG CAAGGCAATG GAAAAGAACA GCGGAGCAAG ATGCCCGTGC AGTCCAAGAG    3780

GCTGCTGAAG AATGGCCCTA GCGGCAGCAA GAAATTCTGG AACAATGTGC TGCCCCACTA    3840

CCTCGAGCTG AAGTGAGCCT CGAGCAGCGC TGCTCGAGAG ATCTGCGGCC GCGAGCTCGG    3900

GGATCCAGAC ATGATAAGAT ACATTGATGA GTTTGGACAA ACCACAACTA GAATGCAGTG    3960

AAAAAAATGC TTTATTTGTG AAATTTGTGA TGCTATTGCT TTATTTGTAA CCATTATAAG    4020

CTGCAATAAA CAAGTTAACA ACAACAATTG CATTCATTTT ATGTTTCAGG TTCAGGGGGA    4080

GGTGTGGGAG GTTTTTTAAA GCAAGTAAAA CCTCTACAAA TGTGGTATGG CTGATTATGA    4140

TCAATGCATC CTAGCCGGAG GAACCCCTAG TGATGGAGTT GGCCACTCCC TCTCTGCGCG    4200

CTCGCTCGCT CACTGAGGCC GCCCGGGCAA AGCCCGGGCG TCGGGCGACC TTTGGTCGCC    4260

CGGCCTCAGT GAGCGAGCGA GCGCGCAGAG AGGGAGTGGC CAA                       4303
```

The components of the transgene cassette of SEQ ID NO:5 and their respective locations are identified in Table 2 below:

TABLE 2

| Location (bp) | Component | Length (bp) |
|---|---|---|
| 1-145 | 5' ITR | 145 |
| 170-368 | GRK promoter | 199 |
| 398-3856 | RPGRorf15 cDNA | 3459 |
| 3899-4143 | SV40 PolyA | 245 |
| 4159-4304 | 3' ITR | 145 |

The 5' ITR has the following sequence:

(SEQ ID NO: 6)
TTGGCCACTCCCTCTCTGCGCGCTCGCTCGCTCACTGAGGCCGGGCGACC

AAAGGTCGCCCGACGCCCGGGCTTTGCCCGGGCGGCCTCAGTGAGCGAGC

GAGCGCGCAGAGAGGGAGTGGCCAACTCCATCACTAGGGGTTCCT

The 3' ITR has the following sequence:

(SEQ ID NO: 7)
AGGAACCCCTAGTGATGGAGTTGGCCACTCCCTCTCTGCGCGCTCGCTCG

CTCACTGAGGCCGCCCGGGCAAAGCCCGGGCGTCGGGCGACCTTTGGTCG

CCCGGCCTCAGTGAGCGAGCGAGCGCGCAGAGAGGGAGTGGCCAA

The SV40 polyadenylation sequence has the following sequence:

(SEQ ID NO: 8)
GGGGATCCAGACATGATAAGATACATTGATGAGTTTGGACAAACCACAAC

TAGAATGCAGTGAAAAAAATGCTTTATTTGTGAAATTTGTGATGCTATTG

CTTTATTTGTAACCATTATAAGCTGCAATAAACAAGTTAACAACAACAAT

TGCATTCATTTTATGTTTCAGGTTCAGGGGGAGGTGTGGGAGGTTTTTTA

AAGCAAGTAAAACCTCTACAAATGTGGTATGGCTGATTATGATCA

Those skilled in the art will appreciate that an AAV vector comprising a transgene and lacking virus proteins needed for viral replication (e.g., cap and rep), cannot replicate since such proteins are necessary for virus replication and packaging. Helper viruses include, typically, adenovirus or herpes simplex virus. Alternatively, as discussed below, the helper functions (E1a, E1b, E2a, E4, and VA RNA) can be provided to a packaging cell including by transfecting the cell with one or more nucleic acids encoding the various helper elements and/or the cell can comprise the nucleic acid encoding the helper protein. For instance, HEK 293 were generated by transforming human cells with adenovirus 5 DNA and now express a number of adenoviral genes, including, but not limited to E1 and E3 (see, e.g., Graham et al., 1977, J. Gen. Virol. 36:59-72). Thus, those helper functions can be provided by the HEK 293 packaging cell without the need of supplying them to the cell by, e.g., a plasmid encoding them.

The viral vector may be any suitable nucleic acid construct, such as a DNA or RNA construct and may be single stranded, double stranded, or duplexed (i.e., self complementary as described in WO 2001/92551).

The viral capsid component of the packaged viral vectors may be a parvovirus capsid. AAV Cap and chimeric capsids are preferred. For example, the viral capsid may be an AAV capsid (e.g., AAV1, AAV2, AAV3, AAV4, AAV5, AAV6, AAV7 AAV8, AAV5, AAV10, AAV11, AAV12, AAV1.1, AAV2.5, AAV6.1, AAV6.3.1, AAV9.45, AAVrh10, AAVrh74, RHM4-1, AAV2-TT, AAV2-TT-S312N, AAV3B-S312N, AAV-LK03, snake AAV, avian AAV, bovine AAV, canine AAV, equine AAV, ovine AAV, goat AAV, shrimp AAV, and any other AAV now known or later discovered. see, e.g., Fields et al., VIROLOGY, volume 2, chapter 69 (4.sup.th ed., Lippincott-Raven Publishers).

In some embodiments, the viral capsid component of the packaged viral vector is a variant of a native AAV capsid (i.e. comprises one or more modifications relative to a native AAV capsid). In some embodiments, the capsid is a variant of an AAV2, AAV5 or AAV8 capsid. In preferred embodiments, the capsid is a variant of an AAV2 capsid, such as those described in U.S. Patent Application Publication Number 2019/0255192A1 (e.g. comprising the amino acid sequence of any of SEQ ID NOs: 42-59). In a particularly preferred embodiment, the capsid comprises a VP1 capsid protein having the following amino acid sequence:

(SEQ ID NO: 9)
MAADGYLPDWLEDTLSEGIRQWWKLKPGPPPPKAAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLAISDQTKHARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL

The variant AAV capsid protein of SEQ ID NO:9 contains the following modifications relative to native AAV2 capsid: (i) a proline (P) to alanine (A) mutation at amino acid position 34, which is located inside the assembled capsid (VP1 protein only), and (ii) an insertion of 10 amino acids (leucine-alanine-isoleucine-serine-aspartic acid-glutamine-threonine-lysine-histidine-alanine/LAISDQTKHA) at amino acid position 588, which is present in VP1, VP2, and VP3.

A full complement of AAV Cap proteins includes VP1, VP2, and VP3. The ORF comprising nucleotide sequences encoding AAV VP capsid proteins may comprise less than a full complement AAV Cap proteins or the full complement of AAV Cap proteins may be provided.

In yet another embodiment the present invention provides for the use of ancestral AAV vectors for use in therapeutic in vivo gene therapy. Specifically, in silico-derived sequences were synthesized de novo and characterized for biological activities. This effort led to the generation of nine functional putative ancestral AAVs and the identification of Anc80, the predicted ancestor of AAV serotypes 1, 2, 8 and 9 (Zinn et al., 2015, Cell Reports 12:1056-1068). Predicting and synthesis of such ancestral sequences in addition to assembling into a virus particle may be accomplished by using the methods described in WO 2015/054653, the contents of which are incorporated by reference herein. Notably, the use of the virus particles assembled from ancestral viral sequences may exhibit reduced susceptibility to pre-existing immunity in current day human population than do contemporary viruses or portions thereof.

The invention includes packaging cells, which are encompassed by "host cells," which may be cultured to produce packaged viral vectors of the invention. The packaging cells of the invention generally include cells with heterologous (1) viral vector function(s), (2) packaging function(s), and (3) helper function(s). Each of these component functions is discussed in the ensuing sections.

Initially, the vectors can be made by several methods known to skilled artisans (see, e.g., WO 2013/063379). A preferred method is described in Grieger, et al. 2015, Molecular Therapy 24(2):287-297, the contents of which are incorporated by reference herein for all purposes. Briefly, efficient transfection of HEK293 cells is used as a starting point, wherein an adherent HEK293 cell line from a qualified clinical master cell bank is used to grow in animal component-free suspension conditions in shaker flasks and WAVE bioreactors that allow for rapid and scalable rAAV production. Using the triple transfection method (e.g., WO 96/40240), the suspension HEK293 cell line generates greater than $10^5$ vector genome containing particles (vg)/cell or greater than $10^{14}$ vg/L of cell culture when harvested 48 hours post-transfection. More specifically, triple transfection refers to the fact that the packaging cell is transfected with three plasmids: one plasmid encodes the AAV rep and cap genes, another plasmid encodes various helper functions (e.g., adenovirus or HSV proteins such as E1a, E1b, E2a, E4, and VA RNA, and another plasmid encodes the transgene and its various control elements (e.g., modified RPGRorf15 gene and hGRK promoter).

To achieve the desired yields, a number of variables are optimized such as selection of a compatible serum-free suspension media that supports both growth and transfection, selection of a transfection reagent, transfection conditions and cell density. A universal purification strategy, based on ion exchange chromatography methods, was also developed that resulted in high purity vector preps of AAV serotypes 1-6, 8, 9 and various chimeric capsids. This user-friendly process can be completed within one week, results in high full to empty particle ratios (>90% full particles), provides post-purification yields (>1.times.10.sup.13 vg/L) and purity suitable for clinical applications and is universal with respect to all serotypes and chimeric particles. This scalable manufacturing technology has been utilized to manufacture GMP Phase I clinical AAV vectors for retinal neovascularization (AAV2), Hemophilia B (scAAV8), Giant Axonal Neuropathy (scAAV9) and Retinitis Pigmentosa (AAV2), which have been administered into patients. In addition, a minimum of a 5-fold increase in overall vector production by implementing a perfusion method that entails harvesting rAAV from the culture media at numerous time-points post-transfection.

The packaging cells include viral vector functions, along with packaging and vector functions. The viral vector functions typically include a portion of a parvovirus genome, such as an AAV genome, with rep and cap deleted and replaced by the modified RPGRorf15 sequence and its associated expression control sequences. The viral vector functions include sufficient expression control sequences to result in replication of the viral vector for packaging. Typically, the viral vector includes a portion of a parvovirus genome, such as an AAV genome with rep and cap deleted and replaced by the transgene and its associated expression control sequences. The transgene is typically flanked by two AAV TRs, in place of the deleted viral rep and cap ORFs. Appropriate expression control sequences are included, such as a tissue-specific promoter and other regulatory sequences suitable for use in facilitating tissue-specific expression of the transgene in the target cell. The transgene is typically a nucleic acid sequence that can be expressed to produce a therapeutic polypeptide or a marker polypeptide.

The terminal repeats (TR(s)) (resolvable and non-resolvable) selected for use in the viral vectors are preferably AAV sequences, with serotypes 1, 2, 3, 4, 5 and 6 being preferred. Resolvable AAV TRs need not have a wild-type TR sequence (e.g., a wild-type sequence may be altered by insertion, deletion, truncation or missense mutations), as long as the TR mediates the desired functions, e.g., virus packaging, integration, and/or provirus rescue, and the like. The TRs may be synthetic sequences that function as AAV inverted terminal repeats, such as the "double-D sequence" as described in U.S. Pat. No. 5,478,745 to Samulski et al., the entire disclosure of which is incorporated in its entirety herein by reference. Typically, but not necessarily, the TRs are from the same parvovirus, e.g., both TR sequences are from AAV2.

The packaging functions include capsid components. The capsid components are preferably from a parvoviral capsid, such as an AAV capsid or a chimeric AAV capsid function. Examples of suitable parvovirus viral capsid components are capsid components from the family Parvoviridae, such as an autonomous parvovirus or a Dependovirus. For example, the capsid components may be selected from AAV capsids, e.g., AAV1, AAV2, AAV3, AAV4, AAV5, AAV6, AAV7, AAV8, AAV9, AAV10, AAV11, AAV12, AAVrh10, AAVrh74, RHM4-1, RHM15-1, RHM15-2, RHM15-3/RHM15-5, RHM15-4, RHM15-6, AAV Hu.26, AAV1.1, AAV2.5, AAV6.1, AAV6.3.1, AAV9.45, AAV2i8, AAV2G9, AAV2i8G9, AAV2-TT, AAV2-TT-S312N, AAV3B-S312N, and AAV-LK03, and other novel capsids as yet unidentified or from non-human primate sources. Capsid components may include components from two or more AAV capsids.

The packaged viral vector generally includes the modified RPGRorf15 gene sequence and expression control sequences flanked by TR elements, referred to herein as the "transgene" or "transgene expression cassette," sufficient to result in packaging of the vector DNA and subsequent expression of the modified RPGRorf15 gene sequence in the transduced cell. The viral vector functions may, for example, be supplied to the cell as a component of a plasmid or an amplicon. The viral vector functions may exist extrachromosomally within the cell line and/or may be integrated into the cell's chromosomal DNA.

Any method of introducing the nucleotide sequence carrying the viral vector functions into a cellular host for replication and packaging may be employed, including but not limited to, electroporation, calcium phosphate precipitation, microinjection, cationic or anionic liposomes, and liposomes in combination with a nuclear localization signal. In embodiments wherein the viral vector functions are provided by transfection using a virus vector; standard methods for producing viral infection may be used.

The packaging functions include genes for viral vector replication and packaging. Thus, for example, the packaging functions may include, as needed, functions necessary for viral gene expression, viral vector replication, rescue of the viral vector from the integrated state, viral gene expression, and packaging of the viral vector into a viral particle. The packaging functions may be supplied together or separately to the packaging cell using a genetic construct such as a plasmid or an amplicon, a Baculovirus, or HSV helper construct. The packaging functions may exist extrachromosomally within the packaging cell, but are preferably integrated into the cell's chromosomal DNA. Examples include genes encoding AAV Rep and Cap proteins.

The helper functions include helper virus elements needed for establishing active infection of the packaging cell, which is required to initiate packaging of the viral vector. Examples include functions derived from adenovirus, baculovirus and/or herpes virus sufficient to result in packaging of the viral vector. For example, adenovirus helper functions will typically include adenovirus components Ela, E1b, E2a, E4, and VA RNA. The packaging functions may be supplied by infection of the packaging cell with the required virus. The packaging functions may be supplied together or separately to the packaging cell using a genetic construct such as a plasmid or an amplicon. See, e.g., pXR helper plasmids as described in Rabinowitz et al., 2002, J. Virol. 76:791, and pDG plasmids described in Grimm et al., 1998, Human Gene Therapy 9:2745-2760. The packaging functions may exist extrachromosomally within the packaging cell, but are preferably integrated into the cell's chromosomal DNA (e.g., E1 or E3 in HEK 293 cells).

Any suitable helper virus functions may be employed. For example, where the packaging cells are insect cells, baculovirus may serve as a helper virus. Herpes virus may also be used as a helper virus in AAV packaging methods. Hybrid herpes viruses encoding the AAV Rep protein(s) may advantageously facilitate for more scalable AAV vector production schemes.

Any method of introducing the nucleotide sequence carrying the helper functions into a cellular host for replication and packaging may be employed, including but not limited to, electroporation, calcium phosphate precipitation, microinjection, cationic or anionic liposomes, and liposomes in combination with a nuclear localization signal. In embodiments wherein the helper functions are provided by transfection using a virus vector or infection using a helper virus; standard methods for producing viral infection may be used.

Any suitable permissive or packaging cell known in the art may be employed in the production of the packaged viral vector. Mammalian cells or insect cells are preferred. Examples of cells useful for the production of packaging cells in the practice of the invention include, for example, human cell lines, such as VERO, WI38, MRCS, A549, HEK 293 cells (which express functional adenoviral E1 under the control of a constitutive promoter), B-50 or any other HeLa cells, HepG2, Saos-2, HuH7, and HT1080 cell lines. In one aspect, the packaging cell is capable of growing in suspension culture, more preferably, the cell is capable of growing in serum-free culture. In one embodiment, the packaging cell is a HEK293 that grows in suspension in serum free medium. In another embodiment, the packaging cell is the HEK293 cell described in U.S. Pat. No. 9,441,206 and deposited as ATCC No. PTA 13274. Numerous rAAV packaging cell lines are known in the art, including, but not limited to, those disclosed in WO 2002/46359. In another aspect, the packaging cell is cultured in the form of a cell stack (e.g. 10-layer cell stack seeded with HEK293 cells).

Cell lines for use as packaging cells include insect cell lines. Any insect cell which allows for replication of AAV and which can be maintained in culture can be used in accordance with the present invention. Examples include *Spodoptera frugiperda*, such as the Sf9 or Sf21 cell lines, *Drosophila* spp. cell lines, or mosquito cell lines, e.g., *Aedes albopictus* derived cell lines. A preferred cell line is the *Spodoptera frugiperda* Sf9 cell line. The following references are incorporated herein for their teachings concerning use of insect cells for expression of heterologous polypeptides, methods of introducing nucleic acids into such cells, and methods of maintaining such cells in culture: Methods in Molecular Biology, ed. Richard, Humana Press, N J (1995); O'Reilly et al., Baculovirus Expression Vectors: A Laboratory Manual, Oxford Univ. Press (1994); Samulski et al., 1989, J. Virol. 63:3822-3828; Kajigaya et al., 1991, Proc. Nat'l. Acad. Sci. USA 88: 4646-4650; Ruffing et al., 1992, J. Virol. 66:6922-6930; Kimbauer et al., 1996, Virol. 219: 37-44; Zhao et al., 2000, Virol. 272:382-393; and Samulski et al., U.S. Pat. No. 6,204,059.

Virus capsids according to the invention can be produced using any method known in the art, e.g., by expression from a baculovirus (Brown et al., (1994) Virology 198:477-488). As a further alternative, the virus vectors of the invention can be produced in insect cells using baculovirus vectors to deliver the rep/cap genes and rAAV template as described, for example, by Urabe et al., 2002, Human Gene Therapy 13:1935-1943.

In another aspect, the present invention provide for a method of rAAV production in insect cells wherein a baculovirus packaging system or vectors may be constructed to carry the AAV Rep and Cap coding region by engineering these genes into the polyhedrin coding region of a baculovirus vector and producing viral recombinants by transfection into a host cell. Notably when using Baculavirus production for AAV, preferably the AAV DNA vector product is a self-complementary AAV like molecule without using mutation to the AAV ITR. This appears to be a by-product of inefficient AAV rep nicking in insect cells which results in a self-complementary DNA molecule by virtue of lack of functional Rep enzyme activity. The host cell is a baculovirus-infected cell or has introduced therein additional nucleic acid encoding baculovirus helper functions or includes these baculovirus helper functions therein. These baculovirus viruses can express the AAV components and subsequently facilitate the production of the capsids.

During production, the packaging cells generally include one or more viral vector functions along with helper functions and packaging functions sufficient to result in replication and packaging of the viral vector. These various functions may be supplied together or separately to the packaging cell using a genetic construct such as a plasmid or an amplicon, and they may exist extrachromosomally within the cell line or integrated into the cell's chromosomes.

The cells may be supplied with any one or more of the stated functions already incorporated, e.g., a cell line with one or more vector functions incorporated extrachromosomally or integrated into the cell's chromosomal DNA, a cell line with one or more packaging functions incorporated extrachromosomally or integrated into the cell's chromosomal DNA, or a cell line with helper functions incorporated extrachromosomally or integrated into the cell's chromosomal DNA The rAAV vector may be purified by methods standard in the art such as by column chromatography or cesium chloride gradients. Methods for purifying rAAV vectors are known in the art and include methods described in Clark et al., 1999, Human Gene Therapy 10(6):1031-1039; Schenpp and Clark, 2002, Methods Mol. Med. 69:427-443; U.S. Pat. No. 6,566,118 and WO 98/09657.

Treatment Methods

In certain embodiments, a method is provided for the treatment of XLRP in a subject in need of such treatment by administering to the subject a therapeutically effective amount of a nucleic acid having a nucleotide sequence at least 90%, at least 95%, at least 98% identical, or 100% identical to the nucleotide sequence of SEQ ID NO:1 or a pharmaceutical composition comprising such a nucleic acid and at least one pharmaceutically acceptable excipient.

In related aspects, a nucleic acid comprising a nucleotide sequence at least 90%, at least 95%, at least 98% identical or 100% identical to the nucleotide sequence of SEQ ID NO:1 for use in the treatment of XLRP is provided.

In other related aspects, the use of a nucleic acid comprising a nucleotide sequence at least 90%, at least 95%, at least 98% identical or 100% identical to the nucleotide sequence of SEQ ID NO:1 for the manufacture of a medicament is provided.

In other related aspects, the use of a nucleic acid comprising a nucleotide sequence at least 90%, at least 95%, at least 98% identical or 100% identical to the nucleotide sequence of SEQ ID NO:1 for the manufacture of a medicament for the treatment of XLRP is provided.

In some aspects, the nucleotide sequence at least 90%, at least 95%, at least 98% identical or 100% identical to the nucleotide sequence of SEQ ID NO:1 is operably linked to an expression control sequence. In some embodiments, the nucleotide sequence of SEQ ID NO:1 is operably linked to a human G protein-coupled receptor rhodopsin kinase 1 (hGRK) promoter. In some preferred embodiments, the hGRK promoter has the sequence of SEQ ID NO:4.

In some embodiments, the nucleotide sequence at least 90%, at least 95%, at least 98% identical or 100% identical to the nucleotide sequence of SEQ ID NO:1 forms part of an expression cassette. In some aspects, the expression cassette comprises from 5' to 3': (a) an AAV2 terminal repeat (b) an hGRK promoter (c) codon optimized RPGRorf15 gene of SEQ ID NO:1 (d) an SV40 polyadenylation sequence and (e) an AAV2 terminal repeat. In preferred embodiments, the 5' AAV2 terminal repeat has the nucleotide sequence set forth as SEQ ID NO:6 and/or the hGRK promoter has the nucleotide sequence set forth as SEQ ID NO:4 and/or the SV40 polyadenylation sequence has the nucleotide sequence set forth as SEQ ID NO:8 and/or the 3' AAV2 terminal repeat has the nucleotide sequence set forth as SEQ ID NO:7. In a particularly preferred embodiment, the expression cassette comprises a nucleic acid comprising the nucleotide sequence of SEQ ID NO:5 or a sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identical thereto.

In further embodiments, a method is provided for the treatment of XLRP in a subject in need of such treatment by administering to the subject a therapeutically effective amount of a recombinant AAV (rAAV) virion, or a pharmaceutical composition comprising same, the rAAV virion comprising (i) a nucleic acid having a nucleotide sequence at least 90%, at least 95%, at least 98% identical or 100% identical to the nucleotide sequence of SEQ ID NO:1 operably linked to an expression control sequence and (ii) an AAV capsid.

In related embodiments, provided is the use of a recombinant AAV (rAAV) virion comprising (i) a nucleic acid having a nucleotide sequence at least 90%, at least 95%, at least 98% identical or 100% identical to the nucleotide sequence of SEQ ID NO:1 operably linked to an expression control sequence and (ii) an AAV capsid for the treatment of XLRP.

In other related embodiments, provided is the use of a recombinant AAV (rAAV) virion comprising (i) a nucleic acid having a nucleotide sequence at least 90%, at least 95%, at least 98% identical or 100% identical to the nucleotide sequence of SEQ ID NO:1 operably linked to an expression control sequence and (ii) an AAV capsid for the manufacture of a medicament for the treatment of XLRP.

In some embodiments, the rAAV virion comprises a native AAV2, AAV4, AAV5 or AAV8 capsid. In other embodiments, the rAAV virion comprises a variant AAV capsid that comprises one or more modifications relative to AAV2, AAV4, AAV5 or AAV8. In a preferred embodiment, the AAV capsid comprises a capsid protein comprising the sequence of SEQ ID NO:9.

In some embodiments, the rAAV virion comprises (i) a native AAV2 capsid or variant thereof and (ii) an expression cassette comprising from 5' to 3': (a) an AAV2 terminal repeat (b) an hGRK promoter (c) codon optimized RPGRorf15 gene of SEQ ID NO:1 (d) an SV40 polyadenylation sequence and (e) an AAV2 terminal repeat. In preferred embodiments, the rAAV comprises (i) a capsid comprising a capsid protein of SEQ ID NO:9 and (ii) a nucleic acid comprising a 5' AAV2 terminal repeat of SEQ ID NO:6, an hGRK promoter of SEQ ID NO:4, an SV40 polyadenylation sequence of SEQ ID NO:8 and a 3' AAV2 terminal repeat of SEQ ID NO:7. In a particularly preferred embodiment, the rAAV comprises (i) a capsid comprising a capsid protein of SEQ ID NO:9 and (ii) an expression cassette comprising the nucleotide sequence of SEQ ID NO:5.

In particularly preferred embodiments, the use of an rAAV in the treatment of XLRP or for the manufacture of a medicament for the treatment of XLRP is provided, wherein the rAAV comprises (i) a nucleic acid comprising a nucleotide sequence of SEQ ID NO:5 and (ii) a capsid comprising a capsid protein having the amino acid sequence of SEQ ID NO:9. In some aspects, the rAAV is administered by intravitreal injection.

In other particularly preferred embodiments, a method for the treatment of XLRP is provided comprising administering to the subject an effective amount of an rAAV comprising (i) a nucleic acid comprising a nucleotide sequence of SEQ ID NO:5 and (ii) a capsid comprising a capsid protein having the amino acid sequence of SEQ ID NO:9. In some aspects, the rAAV is administered to the subject by intravitreal injection.

In other aspects, a pharmaceutical composition is provided comprising a nucleic acid having a nucleotide sequence at least 90%, at least 95% at least 98% identical or 100% identical to the nucleotide sequence of SEQ ID NO:1, optionally operably linked to an expression control sequence, and at least one pharmaceutically acceptable excipient.

In some embodiments, the pharmaceutical composition comprises a nucleic acid comprising the nucleotide sequence of SEQ ID NO:1 operably linked to a constitutive promoter, preferably an hGRK promoter having a sequence at least 90%, at least 95% at least 98% identical or 100% identical to the nucleotide sequence of SEQ ID NO:4.

In other aspects, a pharmaceutical composition is provided comprising at least one pharmaceutically acceptable excipient and an infectious rAAV comprising (i) an AAV capsid and (ii) a nucleic acid comprising from 5' to 3': (a) an AAV2 terminal repeat (b) an hGRK promoter (c) codon optimized RPGRorf15 gene of SEQ ID NO:1 (d) an SV40 polyadenylation sequence and (e) an AAV2 terminal repeat. In related embodiments, the pharmaceutical composition comprises between $10^9$ and $10^{14}$ vg, preferably between $10^{10}$ and $10^{13}$ vg of the rAAV, more preferably comprises $3 \times 10^{11}$ vg or $1 \times 10^{12}$ vg of the rAAV.

In preferred embodiments, the pharmaceutical composition comprises an rAAV comprising (i) a capsid comprising a capsid protein comprising or consisting of the sequence of SEQ ID NO:9 and (ii) a nucleic acid comprising a 5' AAV2 terminal repeat of SEQ ID NO:6 and/or an hGRK promoter of SEQ ID NO:4 and/or an SV40 polyadenylation sequence of SEQ ID NO:8 and/or an AAV2 terminal repeat of SEQ ID NO:7. In related embodiments, the pharmaceutical composition comprises between $10^9$ vg and $10^{14}$ vg, preferably between $10^{10}$ vg and $10^{13}$ vg of the rAAV, more preferably comprises about $3 \times 10^{11}$ vg or about $1 \times 10^{12}$ vg of the rAAV.

In some embodiments, a method for expressing RPGR in one or more photoreceptor cells of a human subject is provided comprising administering to the human subject an effective amount of an infectious rAAV as herein described, wherein the RPGR is expressed in the one or more photoreceptor cells. In some preferred embodiments, the effective amount of infectious rAAV is $10^9$ to $10^{14}$ vg/eye and/or a single dose of the rAAV is intravitreally administered (bilaterally or unilaterally) to the human subject and/or the rAAV comprises a capsid of SEQ ID NO:9 and/or the rAAV comprises a heterologous nucleic acid comprising the nucleotide sequence of SEQ ID NO:5.

In a particularly preferred embodiment, a pharmaceutical composition is provided comprising at least one pharmaceutically acceptable excipient and an infectious rAAV comprising (i) a capsid comprising a capsid protein comprising or consisting of the sequence of SEQ ID NO:9 and (ii) a nucleic acid comprising or consisting of the nucleotide sequence of SEQ ID NO:5. In related embodiments, the pharmaceutical composition comprises between $10^{10}$ and $10^{13}$ vg of the rAAV, preferably comprises about $3 \times 10^{11}$ vg or about $1 \times 10^{12}$ vg of the rAAV.

In some embodiments, a nucleic acid or infectious rAAV as herein described is administered by periocular or intraocular (intravitreal, suprachoroidal or subretinal) injection to a human with XLRP, whereby the XLRP is treated in the subject. In other embodiments, a nucleic acid or infectious rAAV as herein described is administered subretinally or intravitreally to a human with XLRP, whereby the XLRP is treated in the subject. In preferred embodiments, a human subject with XLRP is administered a single intravitreal injection (bilateral or unilateral) of an rAAV as herein described.

In related aspects, treatment of XLRP in a treated subject comprises (i) an improvement (i.e. gain) in visual function or functional vision relative to a control (e.g. relative to a baseline measurement in the treated patient prior to treatment, relative to the untreated eye if the nucleic acid or rAAV is administered unilaterally, or relative to an untreated concurrent or historical control group of XLRP patients) and/or (ii) a decrease in loss of visual function and/or retinal degeneration in a treated eye compared to a control (e.g. untreated eye in same patient or untreated control group) at e.g. 6 months, 12 months or 24 months after treatment. These improvements can be assessed by an appropriate ophthalmological test, including but not limited to visual acuity testing, microperimetry and other visual field testing, anatomical testing, such as optical coherence tomography scans and fundus autofluorescence imaging, retinal electrophysiology, and/or quality of life (QoL) assessments.

In some aspects, an effective amount of a nucleic acid or rAAV (or pharmaceutical composition comprising same) as herein described is an amount effective to treat XLRP in a human patient. In related aspects, an effective amount of an rAAV as herein described is between $10^9$ and $10^{14}$ rAAV particles (or vector genomes (vg))/eye, preferably between $10^{10}$ and $10^{13}$ vg/eye or between $1 \times 10^{11}$ vg/eye and $5 \times 10^{12}$ vg/eye, more preferably is about $3 \times 10^{11}$ vg/eye or about $1 \times 10^{12}$ vg/eye. In some preferred embodiments, a single dose of about $3 \times 10^{11}$ vg/eye or about $1 \times 10^{12}$ vg/eye is intravitreally administered to a human patient with XLRP, whereby the XLRP is treated.

Some embodiments of the invention are exemplified in the following items 1 to 41:

1. A nucleic acid encoding human retinitis pigmentosa GTPase regulator (RPGR) protein of SEQ ID NO:2 and codon optimized for expression in humans, the nucleic acid comprising the nucleotide sequence set forth as SEQ ID NO: 1 or comprising a nucleotide sequence at least 95% identical thereto, wherein the nucleic acid is expressed at a greater level compared with the level of expression of the wild type RPGR nucleotide sequence of SEQ ID NO: 3 in an otherwise identical cell.

2. The nucleic acid according to item 1, wherein the nucleotide sequence has a codon adaptation index of at least 0.89.

3. The nucleic acid according to item 1, comprising the nucleotide sequence set forth as SEQ ID NO: 1.

4. An expression cassette comprising the nucleic acid according to any one of items 1 to 3 and an expression control sequence operably linked and heterologous to the nucleic acid sequence.

5. The expression cassette of item 4, wherein the expression control sequence is a constitutive promoter.

6. The expression cassette of item 4, wherein the expression control sequence is a promoter that directs preferential expression of the nucleic acid in rods and cones, preferably a human G protein-coupled receptor rhodopsin kinase 1 (hGRK) promoter comprising the nucleotide sequence set forth as SEQ ID NO:4 or a sequence at least 90%, at least 95%, or at least 98% identical thereto.

7. The expression cassette of item 6, comprising from 5' to 3': (a) an AAV2 terminal repeat (b) an hGRK promoter (c) codon optimized RPGRorf15 gene of SEQ ID NO:1 (d) an SV40 polyadenylation sequence and (e) an AAV2 terminal repeat.

8. The expression cassette of item 7, wherein the 5' AAV2 terminal repeat has the nucleotide sequence set forth as SEQ ID NO:6 and/or wherein the hGRK promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

9. The expression cassette of item 8, comprising or consisting of the nucleotide sequence of SEQ ID NO:5 or a sequence at least 90%, at least 95%, at least 98% identical thereto.

10. A vector comprising the nucleic acid according to any one of items 1 to 3 or an expression cassette according to any one of items 4 to 9.

11. The vector of item 10, wherein the vector is a recombinant adeno-associated (rAAV) vector.

12. The vector of item 11, wherein the rAAV vector comprises an AAV capsid of serotype 2, 5 or 8 or a variant thereof.

13. The vector of item 12, wherein the rAAV vector comprises an AAV2 capsid or variant thereof.

14. The vector of item 13, wherein the rAAV vector comprises an AAV2 capsid variant comprising a capsid protein comprising or consisting of the sequence of SEQ ID NO:9.

15. The vector of any one of items 11-14, wherein the rAAV vector comprises a nucleic acid comprising from 5' to 3': (a) an AAV2 terminal repeat (b) an hGRK promoter (c) codon optimized RPGRorf15 gene of SEQ ID NO:1 and (d) an AAV2 terminal repeat.

16. The vector of item 15, wherein the 5' AAV2 terminal repeat has the nucleotide sequence set forth as SEQ ID NO:6 and/or wherein the hGRK promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

17. The vector of item 16, wherein the rAAV vector comprises a nucleic acid comprising the nucleotide sequence of SEQ ID NO:5 or a sequence at least 90%, at least 95% or at least 98% identical thereto.

18. The vector of item 17, wherein the rAAV vector comprises (i) a capsid comprising a capsid protein comprising or consisting of the sequence of SEQ ID NO:9 and (ii) a nucleic acid comprising or consisting of the nucleotide sequence of SEQ ID NO:5.

19. A host cell comprising the nucleic acid according to any one of items 1 to 3 or an expression cassette according to any one of items 4 to 9.

20. The host cell according to item 19, wherein the host cell is a mammalian cell.

21. The host cell of item 19 or 20, wherein the host cell is a CHO cell, an HEK293 cell, an HEK293T cell, a HeLa cell, a BHK21 cell or a Vero cell and/or wherein the host cell is grown in a suspension or cell stack culture and/or wherein the host cell is a photoreceptor cell, a retinal ganglion cell, a glial cell, a bipolar cell, an amacrine cell, a horizontal cell, or a retinal pigmented epithelium cell.

22. A method for treating XLRP in a subject in need thereof, comprising administering to the subject a therapeutically effective amount of a nucleic acid according to any one of items 1-3, an expression cassette according to any one of items 4-9 or a vector according to any one of items 10-18.

23. A method for treating XLRP in a subject in need thereof, comprising administering to the subject an infectious rAAV comprising (i) an AAV capsid and (ii) a nucleic acid comprising from 5' to 3': (a) an AAV2 terminal repeat (b) an hGRK promoter (c) codon optimized RPGRorf15 gene of SEQ ID NO:1 (d) an SV40 polyadenylation sequence and (e) an AAV2 terminal repeat.

24. The method according to item 23, wherein the 5' AAV2 terminal repeat has the nucleotide sequence set forth as SEQ ID NO:6 and/or wherein the hGRK promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

25. The method according to item 23 or 24, wherein the rAAV comprises (i) a capsid comprising a capsid protein comprising or consisting of the sequence of SEQ ID NO:9 and (ii) a nucleic acid comprising or consisting of the nucleotide sequence of SEQ ID NO:5.

26. The method according to any one of items 22-25, wherein the nucleic acid or vector is administered to the subject by periocular, intravitreal, suprachoroidal or subretinal injection and/or wherein the vector is administered to the subject at a dosage from about $10^{10}$ vector genomes (vg)/eye to about $10^{13}$ vg/eye, preferably from about $1\times10^{11}$ vg/eye to about $5\times10^{12}$ vg/eye, more preferably at a dosage of about $3\times10^{11}$ vg/eye or at a dosage of about $1\times10^{12}$ vg/eye.

27. A nucleic acid according to any one of items 1-3, an expression cassette according to any one of items 4-9, or a vector according to any one of items 10-18 for use in the treatment of XLRP.

28. A nucleic acid according to any one of items 1-3, an expression cassette according to any one of items 4-9, or a vector according to any one of items 10-18 for use in the manufacture of a medicament for the treatment of XLRP.

29. The nucleic acid, expression cassette or vector for use according to item 27 or 28, wherein the nucleic acid or vector is administered by periocular, intravitreal, suprachoroidal or subretinal injection and/or wherein the vector is for administration at a dosage from about $10^{10}$ vector genomes (vg)/eye to about $10^{13}$ vg/eye, preferably from about $1\times10^{11}$ vg/eye to about $5\times10^{12}$ vg/eye, more preferably is for administration at a dosage of about $3\times10^{11}$ vg/eye or at a dosage of about $1\times10^{12}$ vg/eye.

30. An infectious rAAV comprising (i) an AAV capsid and (ii) a nucleic acid comprising from 5' to 3': (a) an AAV2 terminal repeat (b) an hGRK promoter (c) codon optimized RPGRorf125 gene of SEQ ID NO:1 (d) an SV40 polyadenylation sequence and (e) an AAV2 terminal repeat, for use in the treatment of XLRP.

31. An infectious rAAV comprising (i) an AAV capsid and (ii) a nucleic acid comprising from 5' to 3': (a) an AAV2 terminal repeat (b) an hGRK promoter (c) codon optimized RPGRorf125 gene of SEQ ID NO:1 (d) an SV40 polyadenylation sequence and (e) an AAV2 terminal repeat, for use in the manufacture of a medicament for the treatment of XLRP.

32. The infectious rAAV according to item 30 or 31, wherein the 5' AAV2 terminal repeat has the nucleotide sequence set forth as SEQ ID NO:6 and/or wherein the hGRK promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

33. The infectious rAAV according to item 32, wherein the rAAV comprises (i) a capsid comprising a capsid protein comprising or consisting of the sequence of SEQ ID NO:9 and (ii) a nucleic acid comprising or consisting of the nucleotide sequence of SEQ ID NO:5.

34. The infectious rAAV for use according to any one of items 30-33, wherein the rAAV is administered by intravitreal injection and/or wherein the vector is administered at a dosage from about $10^{10}$ vector genomes (vg)/eye to about $10^{13}$ vg/eye, preferably from about $1\times10^{11}$ vg/eye to about $5\times10^{12}$ vg/eye, more preferably is administered at a dosage of about $3\times10^{11}$ vg/eye or at a dosage of about $1\times10^{12}$ vg/eye.

35. A method for treating a disease or condition mediated by a decreased level of RPGRorf15 in a mammal, the method comprising administering a therapeutically effective amount of a nucleic acid according to any one of items 1-3, an expression cassette according to any one of items 4-9, or a vector according to any one of items 10-18.

36. A method for increasing the level of RPGRorf15 in a mammal, the method comprising administering to the mammal a nucleic acid according to any one of items 1-3, an expression cassette according to any one of items 4-9, or a vector according to any one of items 10-18.

37. A pharmaceutical composition comprising a nucleic acid according to any one of items 1-3, an expression cassette according to any one of items 4-9, or a vector according to any one of items 10-18, and at least one pharmaceutically acceptable excipient.

38. A pharmaceutical composition comprising an infectious rAAV comprising (i) an AAV capsid and (ii) a nucleic acid comprising from 5' to 3': (a) an AAV2 terminal repeat (b) an hGRK promoter (c) codon optimized RPGRorf gene of SEQ ID NO:1 (d) an SV40 polyadenylation sequence and (e) an AAV2 terminal repeat.

39. The pharmaceutical composition according to item 38, wherein the 5' AAV2 terminal repeat has the nucleotide sequence set forth as SEQ ID NO:6 and/or wherein the hGRK promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

40. The pharmaceutical composition according to item 39, wherein the rAAV comprises (i) a capsid comprising a capsid protein comprising or consisting of the sequence of SEQ ID NO:9 and (ii) a nucleic acid comprising or consisting of the nucleotide sequence of SEQ ID NO:5.

41. The pharmaceutical composition according to any one of items 38-40, wherein the pharmaceutical composition comprises between $10^9$ vg and $10^{14}$ vg of the rAAV, preferably between $10^{10}$ vg and $10^{13}$ vg of the rAAV, more preferably comprises about $3 \times 10^{11}$ vg or about $1 \times 10^{12}$ vg of the rAAV.

EXAMPLES

The following examples illustrate preferred embodiments of the present invention and are not intended to limit the scope of the invention in any way. While this invention has been described in relation to its preferred embodiments, various modifications thereof will be apparent to one skilled in the art from reading this application.

Example 1—Codon Optimization of RPGRorf15 cDNA Sequence with Improved Stability The human Retinitis Pigmentosa GTPase Regulator open reading frame 15 (hRPGRorf15) sequence contains a highly repetitive, purine-rich region that leads to sequence instability during transgene cassette cloning and plasmid amplification. The hRPGRorf15 cDNA sequence (NCBI Reference Sequence NM 001034853.1) was codon optimized to generate an RPGRorf15 cDNA sequence with increased expression in human cells and improved sequence stability The codon optimized nucleotide sequence is set forth below:

```
                                                    (SEQ ID NO: 10)
ATGAGAGAGCCTGAAGAGCTGATGCCTGATAGCGGAGCAGTGTTTACCTTTGGGA

AGAGCAAGTTCGCAGAGAATAACCCTGGGAAATTCTGGTTTAAGAACGACGTGCC

CGTGCACCTGAGCTGTGGCGATGAGCACTCCGCCGTGGTGACAGGCAACAATAAG

CTGTACATGTTCGGCTCTAACAATTGGGACAGCTGGGCCTGGGAAGCAAGTCCGC

CATCAGCAAGCCAACCTGCGTGAAGGCCCTGAAGCCCGAGAAGGTGAAGCTGGCC

GCCTGTGGCAGAAACCACACACTGGTGAGCACCGAGGGAGGAAACGTGTACGCAA

CAGGAGGCAACAATGAAGGCCAGCTGGGCCTGGGCGACACAGAGGAGAGGAATA

CCTTTCACGTGATCAGCTTCTTTACCTCCGAGCACAAGATCAAGCAGCTGTCCGCC

GGCTCTAACACAAGCGCCGCCCTGACCGAGGACGGCCGCCTGTTCATGTGGGGCG

ATAATAGCGAGGGCCAGATCGGCCTGAAGAACGTGTCCAACGTGTGCGTGCCTCA

GCAGGTGACCATCGGCAAGCCAGTGTCCTGGATCTCTTGTGGCTACTATCACAGCG

CCTTCGTGACCACAGATGGCGAGCTGTACGTGTTTGGAGAGCCAGAGAACGGCAA

GCTGGGCCTGCCTAACCAGCTGCTGGGCAATCACCGGACACCCCAGCTGGTGTCCG

AGATCCCTGAGAAAGTGATCCAGGTGGCATGCGGAGGAGAGCACACAGTGGTGCT

GACCGAGAATGCCGTGTATACCTTCGGCCTGGGACAGTTTGGACAGCTGGGCCTGG

GCACATTCCTGTTTGAGACAAGCGAGCCAAAAGTGATCGAGAACATCCGCGACCA

GACAATCAGCTACATCTCCTGCGGCGAGAATCACACAGCCCTGATCACCGACATCG

GCCTGATGTATACCTTTGGCGATGGCCGGCACGGCAAGCTGGGCCTGGGCCTGGAG

AACTTCACAAATCACTTTATCCCCACCCTGTGCTCTAACTTCCTGCGGTTCATCGTG

AAGCTGGTGGCCTGCGGCGGCTGTCACATGGTGGTGTTCGCAGCACCTCACAGGGG

AGTGGCCAAGGAGATCGAGTTTGACGAGATCAACGATACATGCCTGTCCGTGGCC

ACCTTCCTGCCATACAGCTCCCTGACATCCGGCAATGTGCTGCAGCGCACCCTGTC

TGCCAGGATGCGGAGAAGGGAGGGGAGCGGTCCCCTGACTCTTTCAGCATGAGG

CGGACACTGCCACCTATCGAGGGCACCCTGGGCCTGTCTGCCTGCTTCCTGCCTAA
```

-continued

```
CAGCGTGTTCCCAAGATGTAGCGAGAGGAATCTGCAGGAGTCTGTGCTGAGCGAG
CAGGATCTGATGCAGCCAGAGGAGCCCGACTACCTGCTGGATGAGATGACAAAGG
AGGCCGAGATCGACAACTCTAGCACCGTGGAGAGCCTGGGCGAGACAACAGATAT
CCTGAATATGACACACATCATGTCCCTGAACTCTAATGAGAAGTCTCTGAAGCTGA
GCCCAGTGCAGAAGCAGAAGAAGCAGCAGACCATCGGCGAGCTGACCCAGGACA
CAGCCCTGACCGAGAACGACGATTCTGATGAGTATGAGGAGATGAGCGAGATGAA
GGAGGGCAAGGCCTGTAAGCAGCACGTGTCCCAGGGCATCTTCATGACCCAGCCA
GCCACCACAATCGAGGCCTTTTCTGACGAAGAGGTGGAGATCCCCGAGGAGAAGG
AGGGCGCCGAGGATAGCAAGGGCAATGGCATCGAGGAGCAGGAGGTGGAGGCCA
ACGAGGAGAATGTGAAGGTGCACGGCGGCAGAAAGGAGAAGACAGAGATCCTGT
CCGACGATCTGACCGACAAGGCCGAGGTGTCCGAGGGCAAGGCCAAGTCTGTGGG
AGAGGCAGAGGACGGACCAGAGGGACGCGGCGATGGAACCTGCGAGGAGGGATC
CTCTGGAGCAGAGCACTGGCAGGACGAAGAAAGAGAGAAGGGCGAGAAGGATAA
GGGCAGAGGAGAGATGGAGAGGCCTGGAGAGGGAGAGAAGGAGCTGGCAGAGAA
GGAGGAGTGGAAGAAGAGGGACGGCGAGGAGCAGGAGCAGAAGGAGAGAGAGC
AGGGCCACCAGAAGGAGAGGAACCAGGAGATGGAGGAGGGAGGAGAGGAGGAG
CACGGCGAGGGAGAGGAGGAGGAGGGCGATAGAGAGGAAGAAGAGGAGAAGGA
GGGAGAGGGCAAGGAGGAAGGCGAGGGAGAGGAGGTGGAGGGAGAAAGGGAGA
AGGAGGAGGGAGAGCGCAAGAAGGAAGAAAGAGCAGGCAAGGAAGAGAAGGGA
GAGGAGGAGGGCGATCAGGGCGAAGGAGAGGAGGAGGAGACAGAGGGAAGGGG
AGAGGAGAAGGAGGAGGGAGGAGAGGTCGAAGGAGGAGAAGTGGAGGAGGGCA
AGGGCGAAAGAGAAGAGGAGGAGGAGGAAGGCGAGGGCGAAGAAGAGGAGGGC
GAGGGCGAGGAAGAAGAGGGCGAGGGCGAAGAGGAAGAAGGCGAGGGCAAGGG
CGAGGAGGAGGGCGAAGAAGGCGAAGGGGAGGAGGAGGGCGAAGAGGGAGAGG
GCGAGGGCGAGGAGGAAGAAGGCGAAGGCGAAGGCGAAGAAGAAGGAGAAGGA
GAGGGCGAAGAGGAGGAAGGCGAAGGAGAAGGAGAGGAGGAAGGAGAAGGGGA
GGGCGAAGAGGAGGAGGGAGAAGGCAAGGAGAAGAAGAAGGCGAAGAAGGCG
AGGGAGAAGGCGAGGAAGAAGAAGGCGAGGGAGAGGGAGAGGACGGCGAAGGC
GAGGGCGAGGAAGAGGAAGGAGAGTGGGAGGGCGAGGAAGAGGAGGGAGAAGG
AGAAGGCGAAGAAGAAGGGGAAGGAGAGGGCGAGGAAGGAGAAGGCGAAGGCG
AAGAGGAGGAGGGGAAGGGGAGGGCGAGGAGGAAGAGGGAGAAGAGGAAGGC
GAAGAAGAGGGAGAAGGCGAAGAGGAAGGAGAAGGCGAGGGAGAAGAAGAGGA
GGAGGGCGAGGTCGAAGGCGAGGTGGAGGGCGAAGAGGGGAAGGCGAAGGCG
AGGAGGAGGAAGGGGAAGAAGAAGGCGAGGAGAGAGAAAGAAGGCGAGGGC
GAGGAGAACAGAAGGAATCGCGAAGAAGAAGAGGAAGAAGAGGGCAAGTACCA
GGAGACAGGCGAGGAGGAGAACAGCGGCAGGATGGCGAGGAGTATAAGAAGGT
GTCCAAGATCAAGGGCTCTGTGAAGTACGGCAAGCACAAGACCTATCAGAAGAAG
AGCGTGACCAACACACAGGGCAATGGCAAGGAGCAGCGCAGCAAGATGCCTGTGC
AGTCCAAGCGGCTGCTGAAGAATGGCCCCTCTGGGAGCAAGAAGTTTTGGAATAA
TGTCCTGCCACACTACCTGGAGCTGAAATGA
```

AAV plasmids containing the codon optimized hRPGRorf15 gene (SEQ ID NO:10) under the control of either the control of human G protein-coupled receptor kinase 1 promoter, also known as the human rhodopsin kinase promoter (hGRK) or the ubiquitous 3-phosphoglycerate kinase (PGK) promoter were constructed by GenScript.

20 ng of AAV plasmid DNA was used to transform competent E. coli (Cat. #C3040H, New England BioLabs, Ipswich, Mass.) and the cells were spread on Kanamycin 50 µg/ml plates (#L1025, Teknova, Hollister, Calif.). Miniprep cultures were grown from the resulting colonies, DNA was prepared with the GeneJET Plasmid Miniprep kit (Cat. #0503, ThermoFisher, Waltham, Mass.) and restriction digested to identify positive clones.

Despite codon optimization, sequence instability of the codon optimized hRPGRorf15 (SEQ ID NO:10) during plasmid production was detected following restriction digestion.

A second codon optimized hRPGRorf15 sequence was developed using a different optimization algorithm that included parameters including, but not limited to, codon usage bias, GC content, AT-rich or GC-rich regions, mRNA secondary structure, RNA instability motifs, cryptic splicing sites, internal chi sites and ribosomal binding sites, and repeat sequences. The codon usage bias in humans was changed by upgrading the codon adaptation index (CAI) to 0.89. The average GC content was optimized from 59.16 in the native sequence to 57 in the optimized sequence to prolong the half-life of the mRNA. The resulting codon optimized nucleotide sequence, set forth herein as SEQ ID NO:1, contains improved codon usage, altered GC content, better mRNA stability, and modification of negative cis acting elements.

An AAV plasmid (pAAV-GRK promoter-cohRPGRorf15-SV40) was constructed comprising the nucleotide sequence of SEQ ID NO:5 (SEQ ID NO:5 comprises (i) 5' AAV2 ITR (SEQ ID NO:6); (ii) codon optimized hRPGRorf15 cDNA (SEQ ID NO:1) under the control of hGRK promoter (SEQ ID NO:4); (iii) SV40 late polyA element (SEQ ID NO:8) and (iv) 3' AAV2 ITR (SEQ ID NO:7)).

pAAV-GRK promoter-cohRPGRorf15-SV40 DNA was prepared as follows. Plasmid DNA from GenScript (20 ng) was used to transform competent E. coli (Cat. #C3040H, New England BioLabs, Ipswich, Mass.) and the cells were spread on Kanamycin 50 µg/ml plates (#L1025, Teknova, Hollister, Calif.). Miniprep cultures were grown from the resulting colonies, DNA was prepared with the GeneJET Plasmid Miniprep kit (Cat. #0503, ThermoFisher, Waltham, Mass.) and restriction digested to identify positive clones. A 50 ml culture in Terrific Broth was grown from one positive clone and DNA was prepared with the Qiagen EndoFree Plasmid Maxi Kit (Cat. #12362, Qiagen, Hilden, Germany). The maxiprep of pAAV-GRK-cohRPGRorf15-SV40 was digested with multiple restriction enzymes to verify the identity of the plasmid. Gel electrophoresis of the restriction digests and the expected fragments are shown in FIG. 1. All actual fragments matched the expected fragments. The sequence of the expression cassette was verified by Sanger DNA sequencing.

Conclusion: The maxiprep of pAAV-GRK-cohRPGRorf15-SV40 mapped correctly by restriction digest and its integrity was verified by Sanger DNA sequencing. Thus, the codon optimized hRPGRorf15 sequence set forth as SEQ ID NO:1 exhibits superior stability relative to both the native sequence of SEQ ID NO:3 and the codon optimized sequence of SEQ ID NO:10.

Example 2—Expression and Activity of Human RPGRorf15 Protein Expressed from Codon Optimized hRPGRorf15 of SEQ ID NO:1

Expression and activity of human RPGRorf15 protein expressed from pAAV-GRK-cohRPGRorf15-SV40 was assessed in transfected HEK293T cells.

Briefly, HEK293T cells were seeded in 12-well plates at 2.0×10^5 cells/well in 1.0 ml DMEM/10% FBS media. HEK293T cells were used due to their high transfectability and protein expression. The next day, 1.0 µg AAV plasmid DNA complexed with 3.0 µl FuGene6 (Cat. #E2691, Promega, Madison, Wis.) was added to the cells in duplicate wells. Two days after transfection, the cells were washed with PBS and lysed in 0.25 ml 1× Passive Lysis Buffer (Promega) containing 1× Halt Protease Inhibitor (ThermoFisher), rocking for 15 minutes at room temperature. Cell debris was pelleted by centrifugation in a microcentrifuge at 12,000 g for 10 minutes at 4° C. The supernatant was collected and stored at −20° C. No-plasmid and pAAV-PGK promoter-cohRPGRorf15-SV40 samples were included in the transfection as negative and positive controls, respectively. pAAV-PGK promoter-cohRPGRorf15-SV40 is identical to the aforementioned AAV vector except that codon optimized hRPGRorf15 is operably linked to a ubiquitous promoter 3-phosphoglycerate kinase (PGK) promoter rather than an hGRK promoter.

Cell lysate (20 µl) was mixed with 10 µl 4×LDS, 4 µl 10× Reducing Agent, and 6 µl water (final volume=40 µl) and denatured at 70° C. for 10 minutes. Samples were loaded on a 12-well Bolt 4-12% Bis-Tris Plus polyacrylamide gel (Invitrogen, NW04122BOX) and ran in 1× MOPS buffer at 200 V for 32 minutes. Separated proteins were transferred to a nitrocellulose filter with the iBlot 2 device (ThermoFisher) for 10 minutes and probed with primary anti-RPGR (Sigma HPA001593 1:2000 and GenScript CT-15 U1729DC260_16 1:500), and anti-polyglutamylation GT335 (AG-20B-0020 1:500, Adipogen, San Diego, Calif.) antibodies using the iBind Flex device (ThermoFisher). Secondary antibodies were HRP-conjugated goat anti-rabbit (ThermoFisher 31460) for the anti-RPGR primary antibodies and HRP-conjugated goat anti-mouse (ThermoFisher 31430) for the anti-polyglutamylation primary antibody. Proteins were visualized with SuperSignal West Dura Chemiluminescent Substrate (ThermoFisher 34076) and imaged on a ChemiDoc MP (BioRad, Hercules, Calif.). All antibodies used are listed below in Table 3.

TABLE 3

| Western Blot Antibodies | | | | |
|---|---|---|---|---|
| Antibody | Host species | Vendor | Catalog # | Dilution |
| Anti-RPGR polyclonal | Rabbit | Sigma | HPA001593 | 1:2,000 |
| Anti-CT-15 | Rabbit | GenScript | U1729DC260_16 | 1:500 |
| Anti-Polyglutamylation GT335 | Mouse | Adipogen | AG-20B-0020 | 1:500 |
| HRP anti-Rabbit IgG (H + L) | Goat | Thermo | 31460 | 1:5,000 |
| HRP anti-Mouse IgG (H + L) | Goat | Thermo | 31430 | 1:5,000 |

Figure 2:
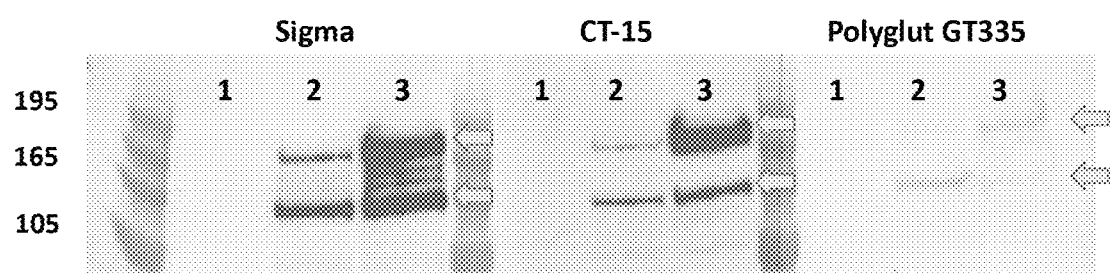
FIG. 2 is Western Blot of cell lysates from HEK293T cells transfected with pAAV-GRK-cohRPGRorf15-SV40. Expression of human RPGRorf15 protein in HEK293 cells was assessed with the indicated primary antibodies (Sigma; CT-15; Polyglut GT335) For each antibody, lane 1=untransfected control; lane 2=pAAV-GRK-cohRPGRorf15-SV40; lane 3=pAAV-PGK-cohRPGRorf15-SV40. The arrows indicate hRPGRorf15 protein. Molecular weight marker (in kilodaltons) is shown on the left-hand side.

FIG. 2 shows an image of a representative Western blot of lysates from transfected HEK293T cells. The CT-15 and Sigma antibodies detect the same 135-140 kD species that appears to be RPGRorf15, as it is present in RPGR-transfected but not untransfected lysates, is the correct size and is recognized by the polyglutamylation-detecting antibody GT335. Expression is higher when driven by the ubiquitous PGK promoter, which is not preferentially active in photoreceptor cells.

Conclusion—Western blot analysis of lysates from transfected HEK293T cells demonstrates expression and polyglutamylation of the correct size hRPGRorf15 protein expressed from the codon optimized hRPGRorf15 of SEQ ID NO:1.

Example 3—Functional Expression of hRPGRorf15 in an In Vitro Model of Human XLRP A human in vitro model system was generated to evaluate correction of the X-linked Retinitis Pigmentosa (XLRP) disease phenotype with the codon optimized human RPGRorf15 nucleic acid having the nucleotide sequence of SEQ ID NO:1. To that end, an AAV vector was constructed comprising the nucleotide sequence of SEQ ID NO:1 driven by the human G-protein coupled receptor rhodopsin kinase 1 (hGRK) promoter (i.e. the AAV vector backbone described in Examples 1 and 2, having the sequence of SEQ ID NO:5) and a variant capsid protein having the amino acid sequence of SEQ ID NO:9. The hGRK promoter was chosen to limit expression of RPGRorf15 to photoreceptors.

Peripheral blood mononuclear cells (PBMCs) were isolated from whole blood drawn from individuals with XLRP and reprogrammed into induced pluripotent stem cells (iPSCs) using the CytoTune iPS 2.0 Sendai Reprogramming Kit (Thermo Fisher Scientific, Waltham, Mass.). Pluripotency of the pluripotent stem cells was confirmed by immunoctyochemistry examining iPSC markers including Sox2, Oct4 and Nanog. The induced pluripotent stem cells were then differentiated into photoreceptors by the methods described in Gonzalez-Cordero et al., Stem Cell Report, 9, 820:837 (2017); Gonzalez Cordero et al., Human Gene Therapy, 29(1) (2018); and Meyer et al., Stem Cells, 29(8): 1206-1218 (2011). Photoreceptor differentiation was confirmed by immunocytochemistry examining specific markers, Recoverin and Rhodopsin. The photoreceptors were confirmed to lack hRPGRorf15 protein expression and glutamylation of the hRPGorf15 protein, which is known to confer functionality.

Immunocytochemistry was as follows: Cells were fixed with 4% paraformaldehyde (PFA) (Santa Cruz Biotechnologies, Dallas, Tex.) for 15 minutes at 4° C. All antibody staining was done in a blocking solution of PBS with 0.2% Triton-X100 (Sigma-Aldrich), 2% bovine serum albumin (Millipore Sigma, Burlington, Mass.), and 5% goat serum (Thermo Fisher Scientific). Primary antibody incubations were done overnight at 4° C. Cells were then incubated with secondary antibodies for one hour at room temperature and then counterstained with DAPI (Sigma Aldrich) in PBS for five minutes at room temperature. Cells were imaged using a Zeiss Axio Observer.D1 Fluorescent Microscope. Image processing was performed using Zeiss Zen 2 software (Carl Zeiss Microscopy LLC, White Plains, N.Y.). A list of primary and secondary antibodies is provided at Table 4:

TABLE 4

| Antibody | Host | Company-Catalog No. | Dilution |
| --- | --- | --- | --- |
| Primary Antibodies | | | |
| OCT4 | Mouse | Millipore- MAB4401 | 1:50 |
| Nanog | Rabbit | Abcam- ab21624 | 1:50 |
| SOX2 | Rabbit | Abcam- ab92494 | 1:50 |

TABLE 4-continued

| Antibody | Host | Company-Catalog No. | Dilution |
| --- | --- | --- | --- |
| Beta-Tubulin III | Mouse | Sigma- T8578 | 1:200 |
| HNF4-α | Rabbit | Santa Cruz-SC-8987 | 1:100 |
| A-SMA | Mouse | Sigma Aldrich- A2547 | 1:500 |
| Recoverin | Rabbit | EMD Millipore- AB5585 | 1:100 |
| Rhodopsin | Mouse | Abcam- AB98887 | 1:100 |
| RPGR | Rabbit | Sigma- HPA001593 | 1:2000 |
| GT335 | Mouse | Fisher Adipogen-50-463-394# | 1:4000 |
| Alpha Tubulin | Rabbit | Abcam- ab52866 | 1:4000 |
| Secondary Antibodies | | | |
| Alexa Fluor488 anti-rabbit | Goat | Invitrogen-A11078 | 1:500 |
| Alexa Fluor555 anti-rabbit | Goat | Invitrogen-A21428 | 1:500 |
| Alexa Fluor680 anti-rabbit | Goat | Invitrogen-A21109 | 1:500 |
| Alexa Fluor488 anti-mouse | Goat | Invitrogen-A11029 | 1:500 |
| Alexa Fluor555 anti-mouse | Goat | Invitrogen-A21422 | 1:500 |
| Alexa Fluor680 anti-mouse | Goat | Invitrogen-35518 | 1:500 |
| Horseradish Peroxidase anti-Rabbit IgG (H + L) | Goat | Thermo-31460 | 1:5000 |
| Horseradish Peroxidase anti-Mouse IgG (H + L) | Goat | Thermo-31430 | 1:5000 |

To assess transcript levels of codon optimized RPGRorf15 transgene following transduction into the XLRP-iPSC derived diseased photoreceptors, XLRP photoreceptors (PR) were transduced with the above-described AAV vectors at a multiplicity of infection (MOI, viral genomes per cell) of 50,000 to ensure levels above the limit of detection of the assays. RNA was isolated 30 days post transduction and cDNA was synthesized. Digital droplet PCR was run on the prepared samples and transcript levels per droplet were analyzed as a copies/mL value. Quantification of the number of droplets, above the set threshold, containing the transcript of the primer/probe set was examined. Two primer/probe sets were created to specifically differentiate the codon optimized human RPGRorf15 transgene from the endogenous human RPGR1-19 constitutive isoform (hRPGR1-19).

Figure 3:
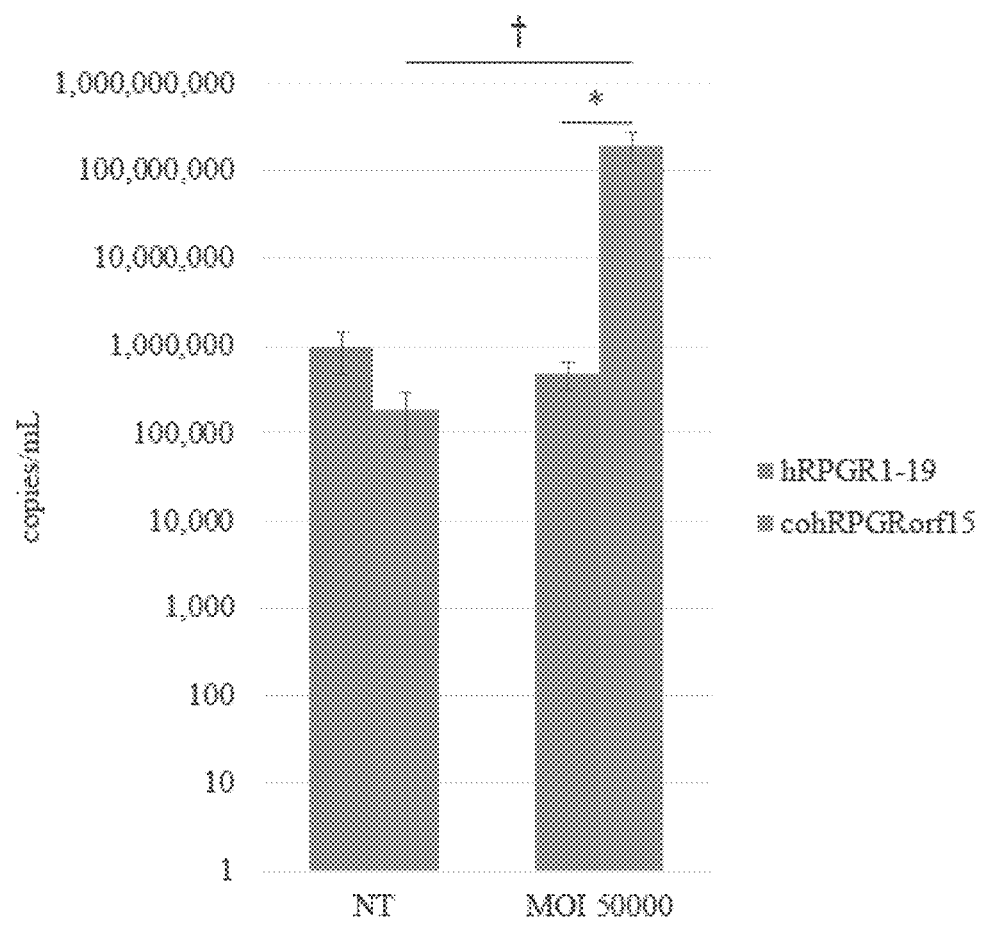
FIG. 3 Transduction with recombinant AAV (rAAV) virions comprising codon optimized RPGRorf15 of SEQ ID NO:1 under the control of an hGRK1 promoter leads to a robust increase of cohRPGRorf15 (SEQ ID NO:1) transcript levels in XLRP-iPSC-derived photoreceptor cells. Digital droplet PCR was performed on RNA extracted from XLRP-iPSC derived photoreceptor cultures following transduction with rAAV comprising pAAV-GRK-cohRPGRorf15-SV40 and capsid of SEQ ID NO:9 at MOI of 50,000, thirty days post transduction. hRPGR1-19 (internal control) and cohRPGRorf15 transcript levels were determined and quantified as copies/mL above a set threshold and plotted on a log scale. Following transduction, codon optimized hRPGRorf15 (SEQ ID NO:1) transcript level was statistically greater than hRPGR1-19. NT=non-transduced, MOI=multiplicity of infection, hRPGR1-19=human retinitis pigmentosa GTPase regulator exon 1-19, constitutive isoform, cohRPGRorf15=codon optimized human retinitis pigmentosa GTPase regulator open reading frame 15, retinal specific isoform of SEQ ID NO:1. *p≤0.05 compared to MOI 50,000 hRPGR1-19, †p≤0.05 compared to NT cohRPGRorf15. Error bars±Standard Deviation. n=3 per Patient. Y-axis in log scale.

Non-transduced XLRP diseased cells expressed low, background levels of cohRPGRorf15 transcript, as expected. Following transduction with AAV vector, cells showed over a 400-fold increase of cohRPGRorf15 transcript levels compared to hRPGR1-19. Transduced cells displayed over a 1000-fold increase in cohRPGRorf15 transcript compared to non-transduced cell cohRPGRorf15 levels. Non-transduced cells had a higher level of hRPGR1-19 than cohRPGRorf15. See FIG. 3. Analysis was done in triplicate and levels were averaged. Transduction with AAV vector comprising codon optimized hRPGRorf15 of SEQ ID NO:1 significantly increased transcript levels of cohRPGRorf15 in photoreceptor cultures.

Figure 4:
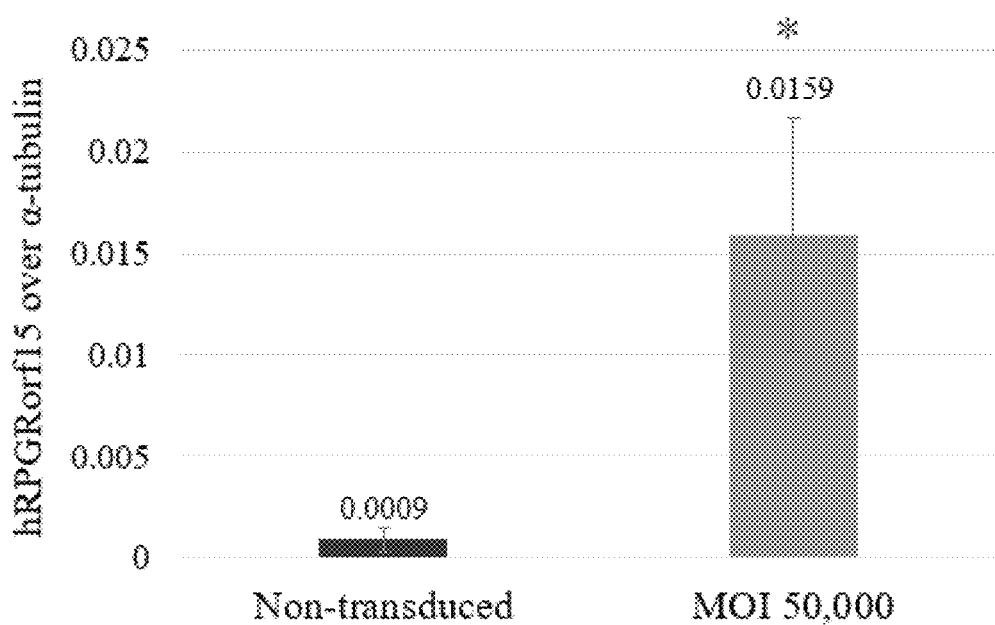
FIG. 4 Transduction with rAAV comprising codon optimized RPGRorf15 of SEQ ID NO:1 under the control of an hGRK promoter increases hRPGRorf15 protein levels in XLRP photoreceptor cultures. XLRP-iPSC derived photoreceptor cultures were transduced at MOI of 50,000 and protein lysates were harvested 30 days post transduction. SDS-PAGE and Western blot showed an increase in hRPGRorf15, at 127 kDa, compared to non-transduced cells (NT) for both patients, normalized to the loading control α-tubulin. Band intensity was quantified and averaged between patients. Transduction with rAAV yielded a significant increase in hRPGRorf15 protein. *p≤0.05 compared to NT. Error bars±Standard Deviation. n=3 per Patient.

To assess protein levels of codon optimized human RPGRorf15 transgene produced by transduction of XLRP-iPSC derived photoreceptor cells with the AAV vectors, XLRP-iPSC derived diseased photoreceptors were transduced at a MOI of 50,000 vg/cell. Cell lysates were collected 30 days post transduction and SDS-PAGE and Western blot analysis were carried out to evaluate hRPGRorf15 protein levels. Band intensity was quantified and is depicted as a histogram in FIG. 4. Transduction with AAV vector elicited a significant increase in expression of human RPGRorf15 protein, compared to non-transduced cells.

Figure 5:
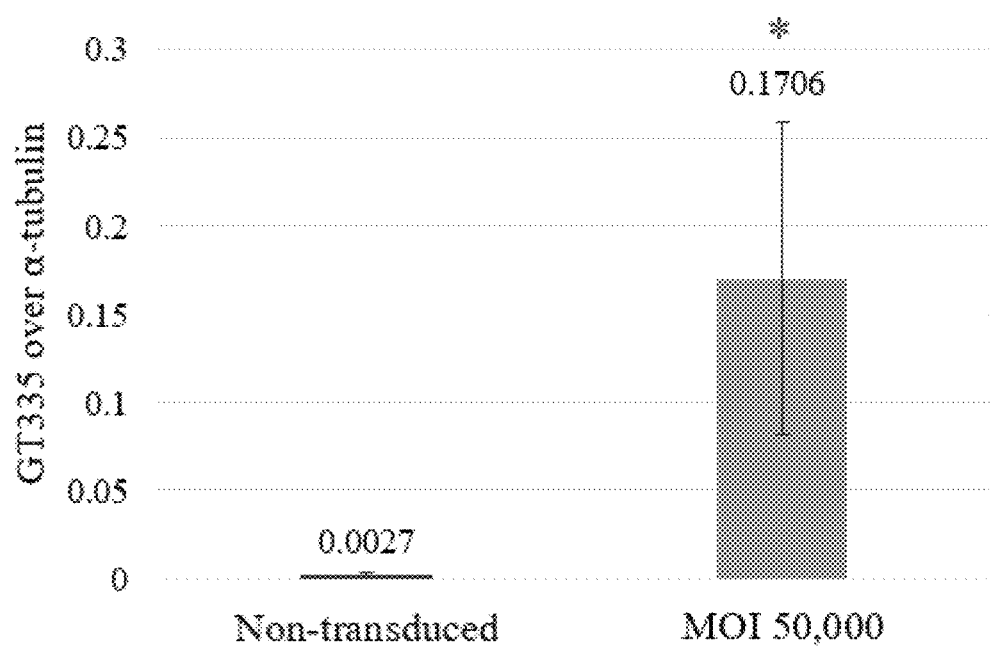
FIG. 5 Glutamylation of hRPGRorf15 following transduction with rAAV comprising codon optimized RPGRorf15 of SEQ ID NO:1 under the control of an hGRK promoter in XLRP photoreceptor cultures. XLRP-iPSC derived photoreceptor cultures were transduced at a MOI of 50,000 and protein lysates were harvested 30 days post transduction. SDS-PAGE and Western blot analyses showed an increase in glutamylation of a 127 kDa protein, hRPGRorf15, compared to nontransduced (NT) control for both patients, normalized to the loading control, α-tubulin band intensity was quantified and averaged between patients. Transduction with rAAV yielded a significant increase in glutamylation of hRPGRorf15 protein. GT335=anti-glutamylation antibody, NT=non-transduced, MOI=Multiplicity of Infection, hRPGRorf15=human Retinitis Pigmentosa GTPase Regulator Open Reading Frame 15, retinal specific isoform. *p≤0.05 compared to NT. Error bars±Standard Deviation. n=3 per Patient.

In order to determine whether the cohRPGRorf15 protein exogenously introduced into photoreceptors was functional, glutamylation, a surrogate of function, was examined. Glutamylation of hRPGRorf15 and protein function are strongly correlated according to published work. (Fischer et al., 2017; Rao et al., 2016; Sun et al., 2016). XLRP-iPSC-derived diseased PR were transduced at a MOI of 50,000 vg/cell. Cell lysates were collected 30 days post transduction and SDS-PAGE and Western blot analysis was carried out to evaluate glutamylation of the expressed hRPGRorf15 protein. Glutamylation was determined by probing the membrane with a glutamylation specific antibody, GT335, and examining positive banding patterns at the hRPGRorf15 size, 127 kDa. Band intensity was quantified and depicted as a histogram at FIG. 5. Transduction of PR cells with AAV vector comprising codon optimized hRPGRorf15 nucleotide sequence led to a significant increase in glutamylation of human RPGRorf15 protein, compared to non-transduced cells in both XLRP patient-derived diseased photoreceptors.

Figure 6:
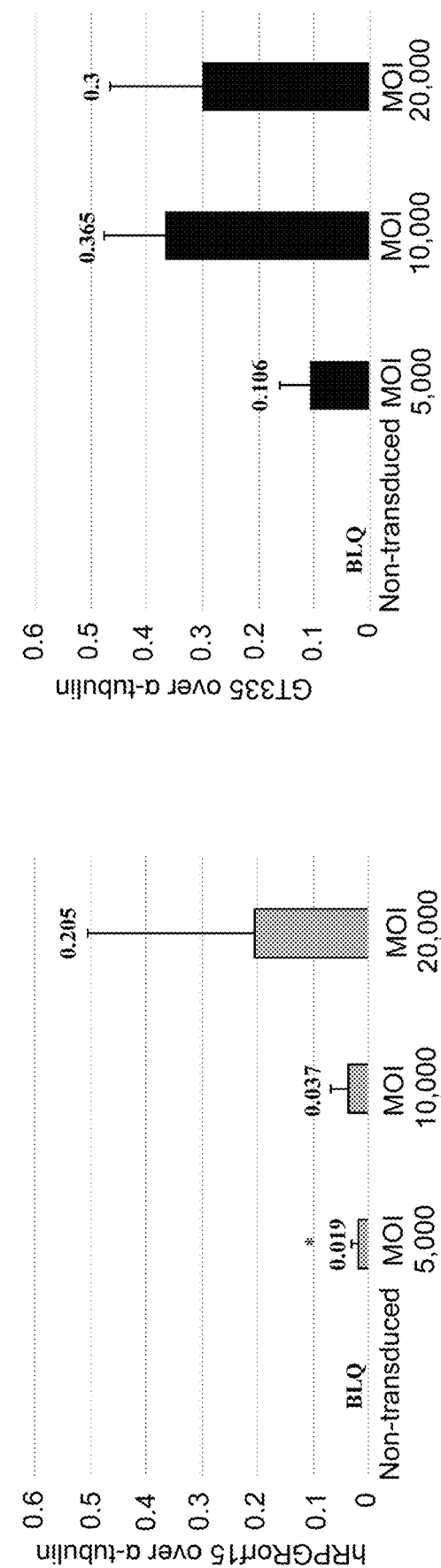
FIG. 6 Constitutive promoter drives increase in hRPGRorf15 protein and glutamylation in XLRP photoreceptor cultures. XLRP-iPSC derived photoreceptor cultures were transduced with rAAV comprising codon optimized RPGRorf15 of SEQ ID NO:1 under the control of a PGK promoter at MOIs of 5,000, 10,000 and 20,000. Protein lysates were harvested 30 days post transduction. SDS-PAGE and Western blot showed an increase in hRPGRorf15, and glutamylation at 127 kDa, compared to non-transduced (NT) control for Patient 78, normalized to the loading control, α-tubulin. Band intensity was quantified. Transduction yielded a significant increase in hRPGRorf15 protein. NT=non-transduced, MOI=Multiplicity of Infection, hRPGRorf15=human Retinitis Pigmentosa GTPase Regulator Open Reading Frame 15, retinal specific isoform, GT335=anti-glutamylation antibody. *p≤0.05 compared to NT. Error bars±Standard Deviation. n=3.
Figure 8:
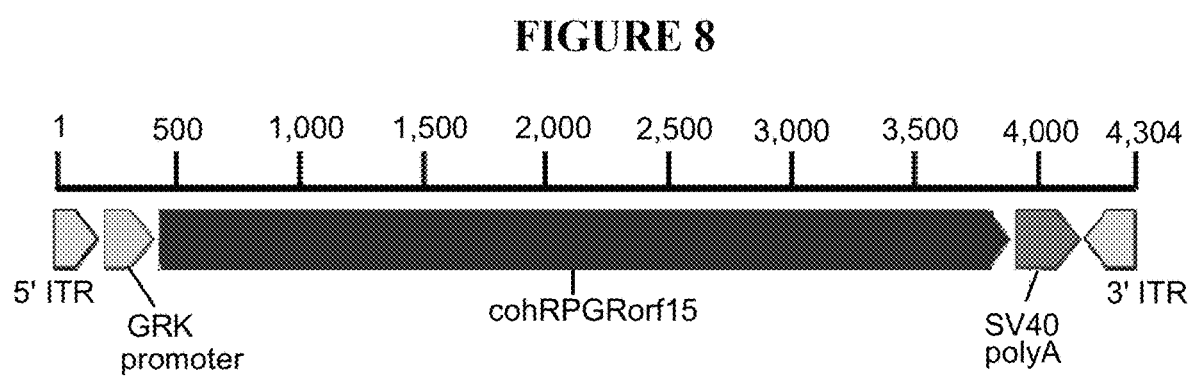
FIG. 8 is a schematic of the transgene cassette contained within the rAAV described in the Examples below. The transgene cassette comprises a 5'AAV2 ITR, a human rhodopsin kinase (aka hGRK) Promoter, a Codon Optimized Human RPGRorf15 cDNA of SEQ ID NO:1, a late SV40 Polyadenylation Signal, and a 3' AAV2 ITR and has the nucleotide sequence of SEQ ID NO:5.

Due to the low hRPGRorf15 protein levels detected in the Western blot with use of a high MOI, a dose response of the hRPGRorf15 codon optimized transgene (cohRPGRorf15) was verified. To this end, an AAV vector was constructed comprising the codon optimized RPGRorf15 sequence of SEQ ID NO:1 operably linked to a ubiquitous promoter 3-phosphoglycerate kinase (PGK) and a capsid of SEQ ID NO:9 (this AAV vector was identical to the AAV vector described above aside from the promoter). Diseased photoreceptors were transduced at three MOIs, 5,000, 10,000 and 20,000. Cell lysates were collected 30 days post transduction and SDS-PAGE and Western blot analyses were carried out to evaluate hRPGRorf15 protein levels and glutamylation (GT335=anti-glutamylation antibody). Band intensity was quantified and depicted as a histogram (FIG. 6). Although there was high variability, due to the heterogeneity of the cultures, hRPGRorf15 protein and glutamylation of hRPGRorf15 were observed at lower MOIs using a constitutive promoter to drive cohRPGRorf15 expression.

Conclusion—the in vitro studies with iPSC-derived photoreceptors have demonstrated that AAV-mediated delivery of codon optimized hRPGRorf15 of SEQ ID NO:1 restores human RPGRorf15 transcript and transgene expression in human XLRP diseased photoreceptors. Furthermore, the RPGRorf15 protein, expressed following transduction of 4D-125, was post-translationally glutamylated. Based on published literature, glutamylation confers functionality of RPGRorf15.

Example 4—Assessment of Safety and Biodistribution of Codon Optimized RPGRorf15 cDNA Sequence Delivered by R100 Via Intravitreal Administration in Non-Human Primates Materials and Methods
GLP Toxicology and Biodistribution Studies Male cynomolgus macaques (*Macaca fascicularis*) aged 2-14 years were dosed via two 50 µL intravitreal injections into each eye through the sclera for a total dose volume of 100 µL/eye. Doses of $1\times10^{11}$ vg/eye and $1\times10^{12}$ vg/eye were evaluated. The animals were anesthetized with Ketamine IM and given topical ophthalmic solutions to eliminate pain. 20-80 mg of methylprednisolone was administered by IM injection weekly post-injection. Euthanasia was performed by trained veterinary staff at Week 3, Week 13, and Week 26 post-administration.

4D-125 (rAAV comprising a capsid protein of SEQ ID NO:9 and a heterologous nucleic acid comprising the nucleotide sequence of SEQ ID NO:5) genome biodistribution was assessed in all major ocular compartments (retina, optic nerve, ciliary body, iris, trabecular meshwork), and major systemic organs (including the testes) using validated, GLP-compliant qPCR assay. In tissues where genomes were detected, transgene expression was assessed by a qualified, GLP-compliant RT-qPCR assay.

Serial toxicology assessments performed in the study were: clinical ocular evaluations (complete ophthalmic examinations, including SD-OCT imaging and ERG), systemic evaluations, clinical pathology, gross pathology and microscopic pathology. Assays were validated to determine the anti-capsid and anti-transgene antibody responses. ELISpot assays were validated to detect cellular responses to the R100 (comprising a variant capsid protein of SEQ ID NO:9) capsid and expressed proteins.

Neutralizing Antibody Assay

2v6.11 cells were plated at a density of $3\times10^4$ cells/well 24 hours prior to infection. rAAV vectors encoding firefly luciferase driven by the CAG promoter were incubated at 37° C. for 1 hour with individual serum samples prior to infection, and cells were then infected at a genomic MOI of 1,000. Luciferase activity was assessed 48 hours post infection using the Luc-Screen Extended-Glow Luciferase Reporter Gene Assay System (Invitrogen) or the ONE-Glo Luciferase Assay System (Promega) and quantified using the BioTek Cytation 3 Cell Imaging Multi-Mode Reader and Gen5 software.

Prior to enrollment in studies, non-human primates (NHP) serum was screened for the presence of neutralizing antibodies against R100. NHPs were enrolled in studies when samples resulted in less than 50% neutralization of AAV transduction at a 1:10 serum dilution.

AAV Manufacturing

Recombinant R100 viral vectors were produced by transient transfection in HEK293 cells. Cells were cultured in DMEM supplemented with FBS and were maintained at 37° C. in a 5% $CO_2$ environment. Cells were triply transfected (payload, capsid, and helper plasmids) using polyethylenimine (PEI). 48-96 hours post-transfection, viral particles were harvested from cells and/or supernatant and cells lysed via microfluidization. Cell lysate and/or supernatant was enzymatically treated to degrade plasmid and host-cell DNA, then clarified and concentrated by tangential flow filtration (TFF). The TFF retentate was then loaded onto an affinity resin column for purification. Following pH-gradient elution, post-affinity material was buffer exchanged, then further purified (if needed) by anion-exchange chromatography. Purified rAAV was then formulated into DPBS with 0.001% polysorbate-20, sterile filtered, and filled to yield rAAV Drug Product.

Results 4D-125 Delivery is Safe and Results in Expression of Therapeutic Transgene in NHP 4D-125 (R100.GRK-cohRPGRorf15) has been advanced into a Phase 1-2 clinical trial. Investigational New Drug (IND)-enabling data for this product includes evaluation in a 6-month Good Laboratory Practices (GLP) toxicology and biodistribution study (Table 5). A total of 30 eyes of 30 NHPs were injected by intravitreal injection with a single eye administration.

TABLE 5

Good Laboratory Practices (GLP) Toxicology and Biodistribution Studies

| 4DMT Study Number | Lot Number | Number | Gender | Eye(s) | Dose | In-Life |
|---|---|---|---|---|---|---|
| 4D18-08 | N/A | 1 | Male | OD | vehicle | 3 weeks |
|  | 4DEP000008.01 | 5 | Male | OD | 1E+11 vg/eye |  |
|  |  | 5 | Male | OD | 1E+12 vg/eye |  |
|  | N/A | 1 | Male | OD | vehicle | 13 weeks |
|  | 4DEP000008.01 | 5 | Male | OD | 1E+11 vg/eye |  |
|  |  | 5 | Male | OD | 1E+12 vg/eye |  |
|  | N/A | 1 | Male | OD | vehicle | 26 weeks |
|  | 4DEP000008.01 | 5 | Male | OD | 1E+11 vg/eye |  |
|  |  | 5 | Male | OD | 1E+12 vg/eye |  |

Figure 9:
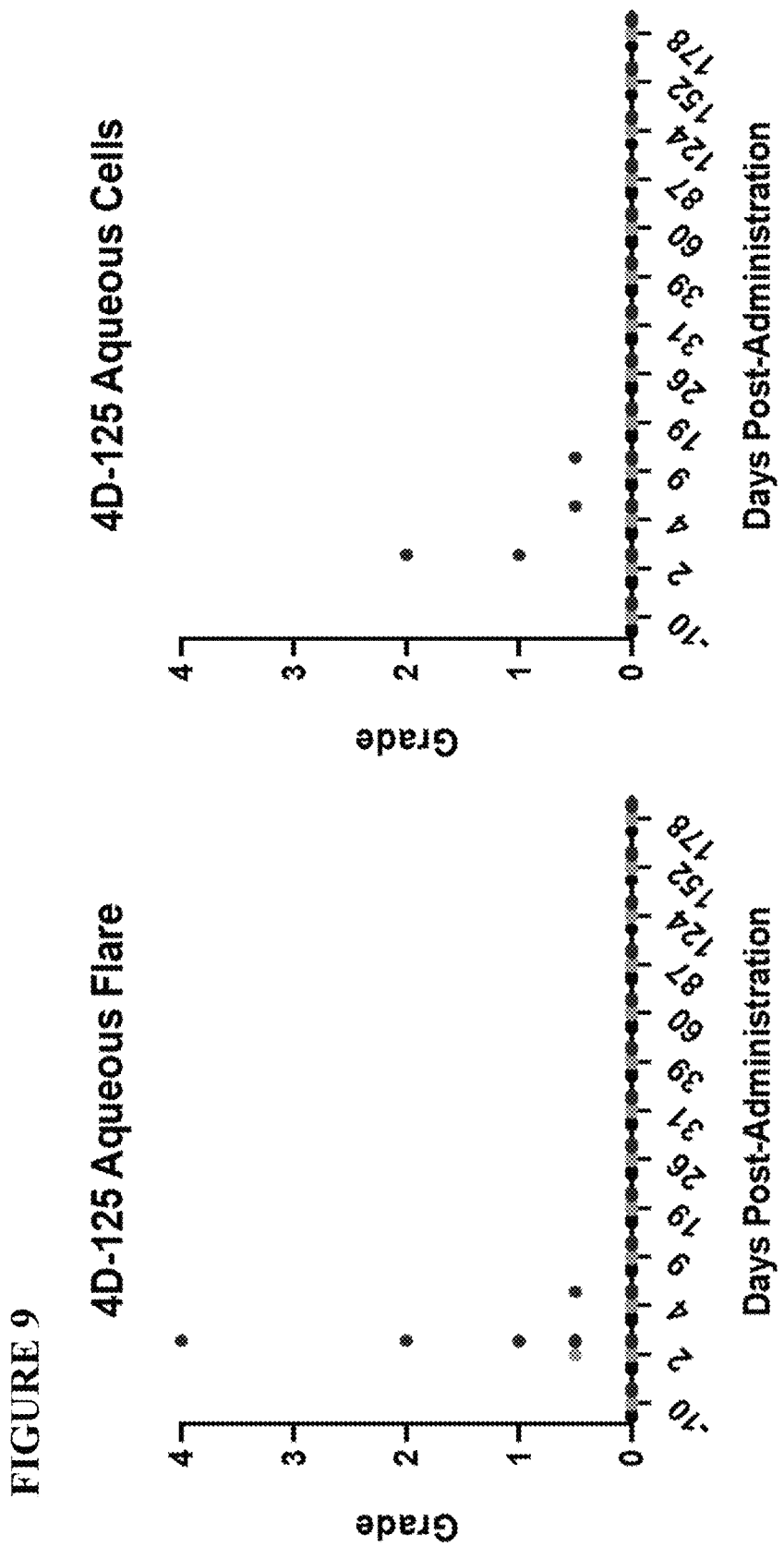
FIG. 9 illustrates safety of 4D-125 (comprising the transgene cassette shown in FIG. 8 and a capsid protein of SEQ ID NO:9) through quantification of ocular inflammation, as assessed by aqueous flare, aqueous cells, and vitreous cells. Ophthalmoscopic signs of transient mild ocular inflammation were observed at the high dose. These changes responded to an increase in the systemic steroid treatment. There were no adverse findings considered related to 4D-125. IOP values were within normal limits for all animals at the different examination intervals. ERG values and OCT images including macular morphology were also within normal limits.
Figure 9:
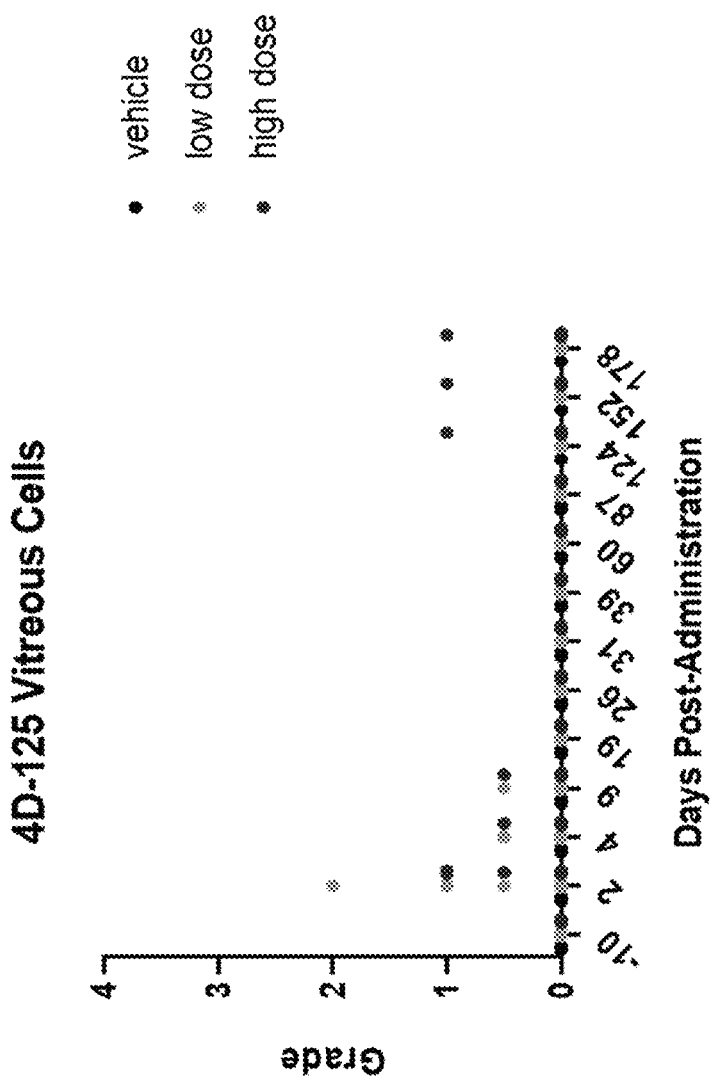

No significant toxicities were observed with 4D-125 at either dose level, as determined by clinical observations, histopathology, OCT, or ERG. Administration of 4D-125 into a single eye resulted in only minimal to mild anterior uveitis that was restricted to the immediate post-administration period and resolved by Week 3 (FIG. 9); in some cases systemic steroid doses were transiently increased.

Figure 10:
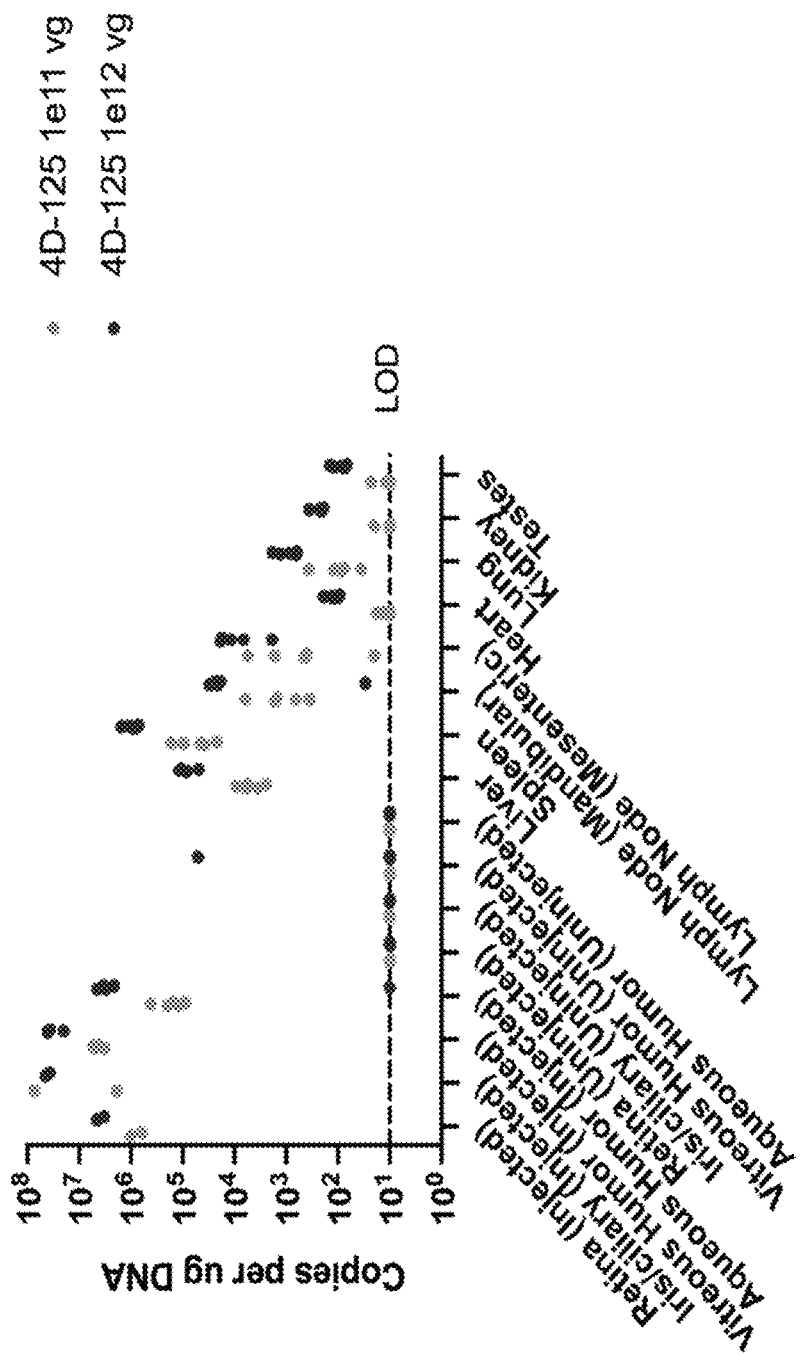
FIG. 10 illustrates vector genome biodistribution in selected retinal, ocular, and non-ocular tissues, as measured by qPCR at 3 necropsy timepoints in NHPs intravitreally administered 4D-125. LOD=lower limit of detection; all samples "BLOD" graphed at LOD value for visualization purposes.
Figure 10:
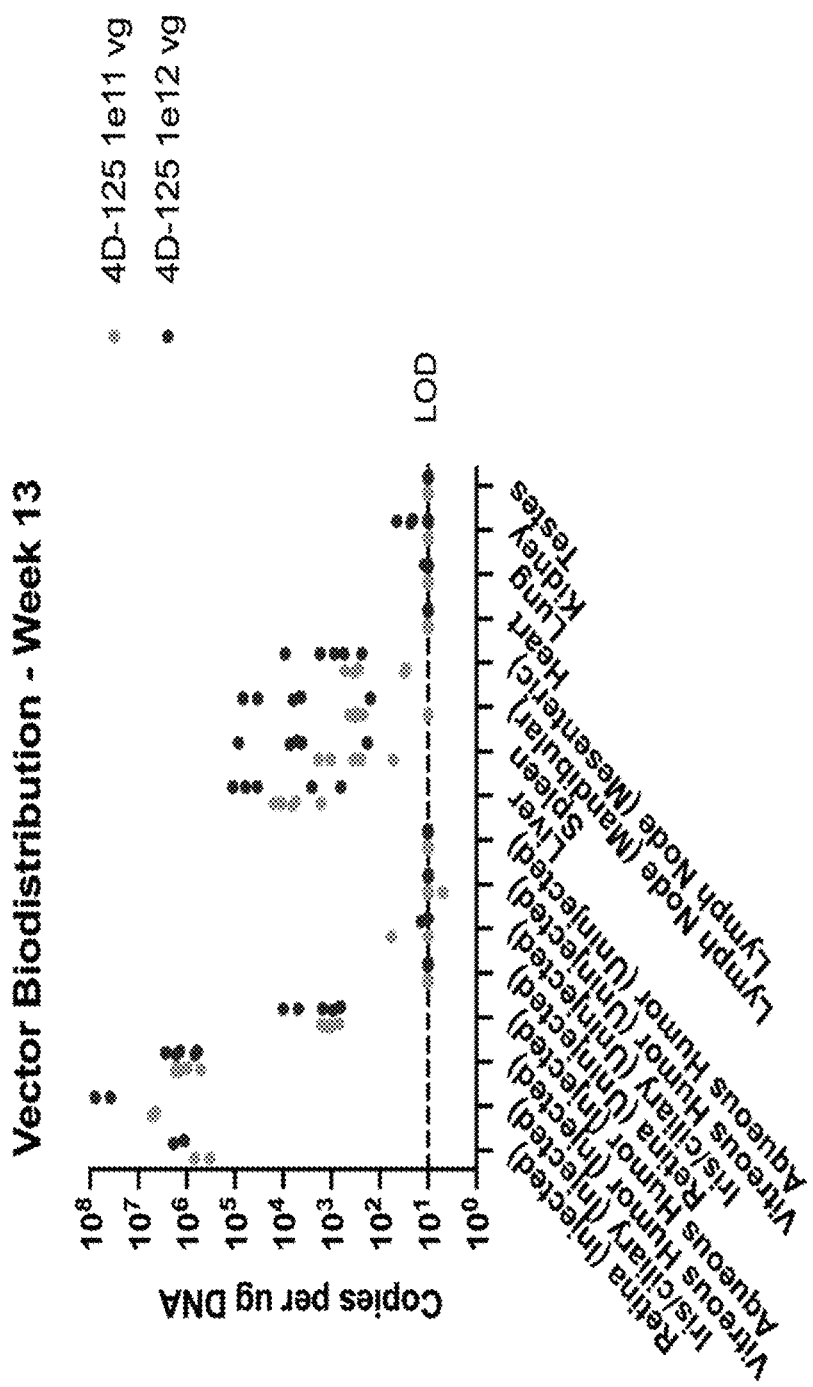
Figure 10:
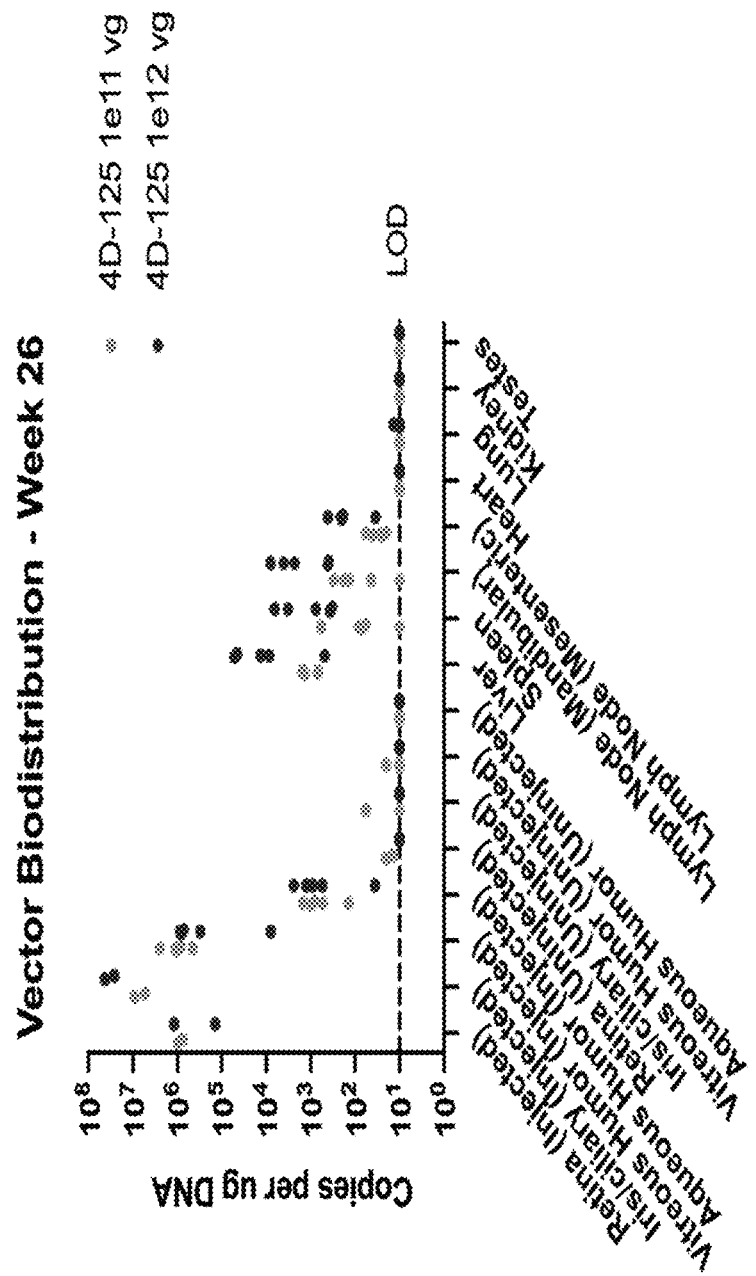
Figure 11:
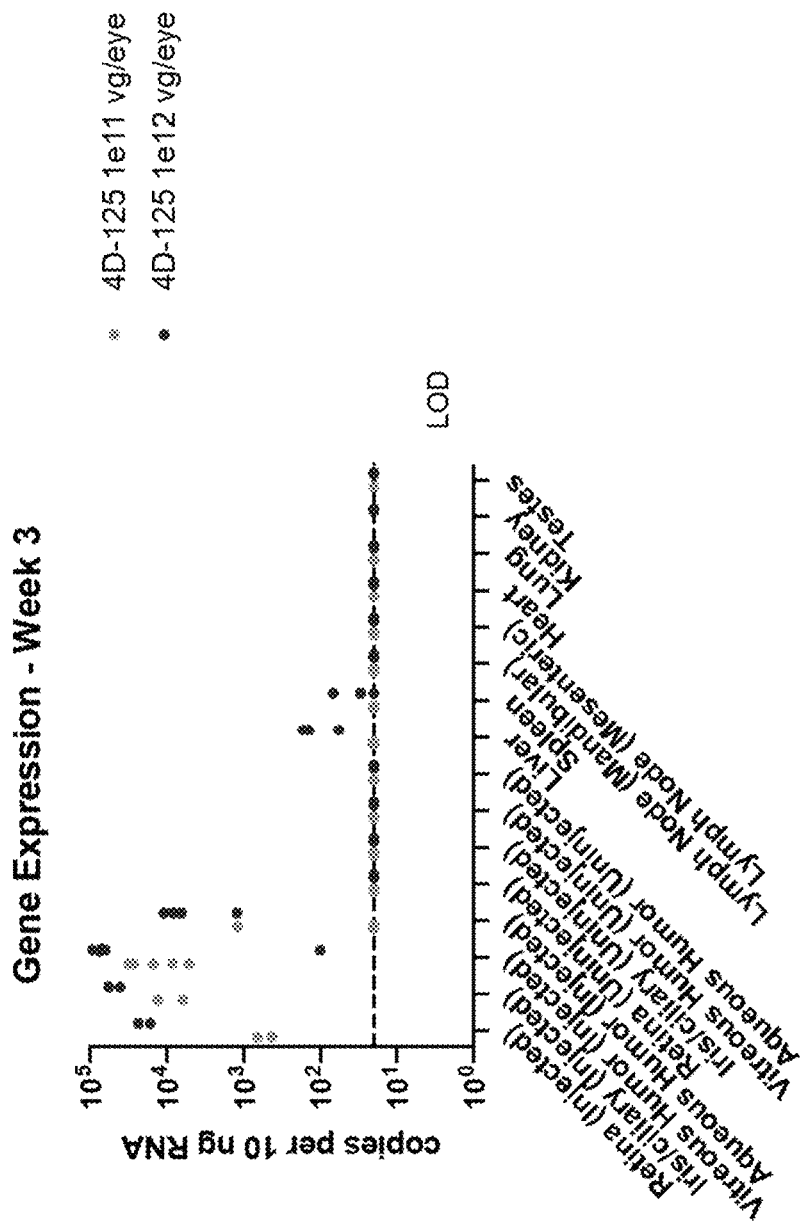
FIG. 11 illustrates RPGR transgene mRNA expression in selected retinal, ocular, and non-ocular tissues, as measured by RT-qPCR at 3 necropsy timepoints in NHPs intravitreally administered 4D-125. LOD=lower limit of detection; all samples "BLOD" graphed at LOD value for visualization purposes.
Figure 11:
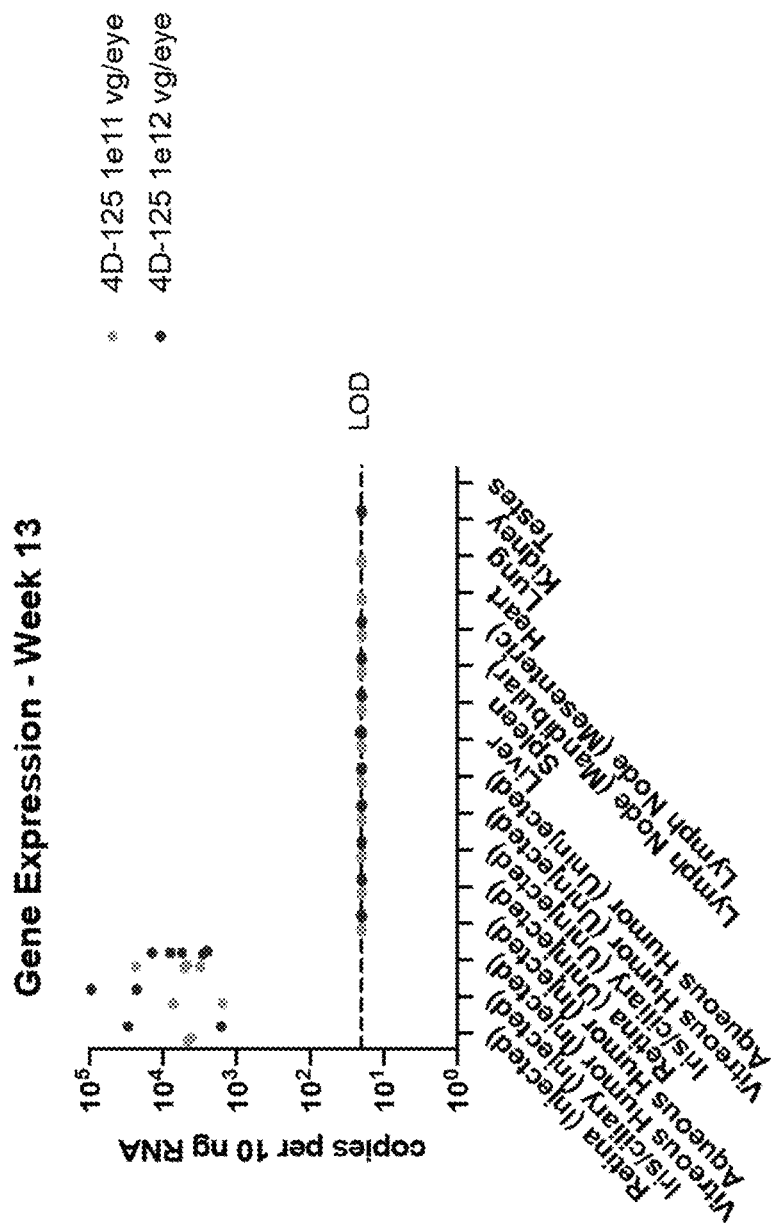
Figure 11:
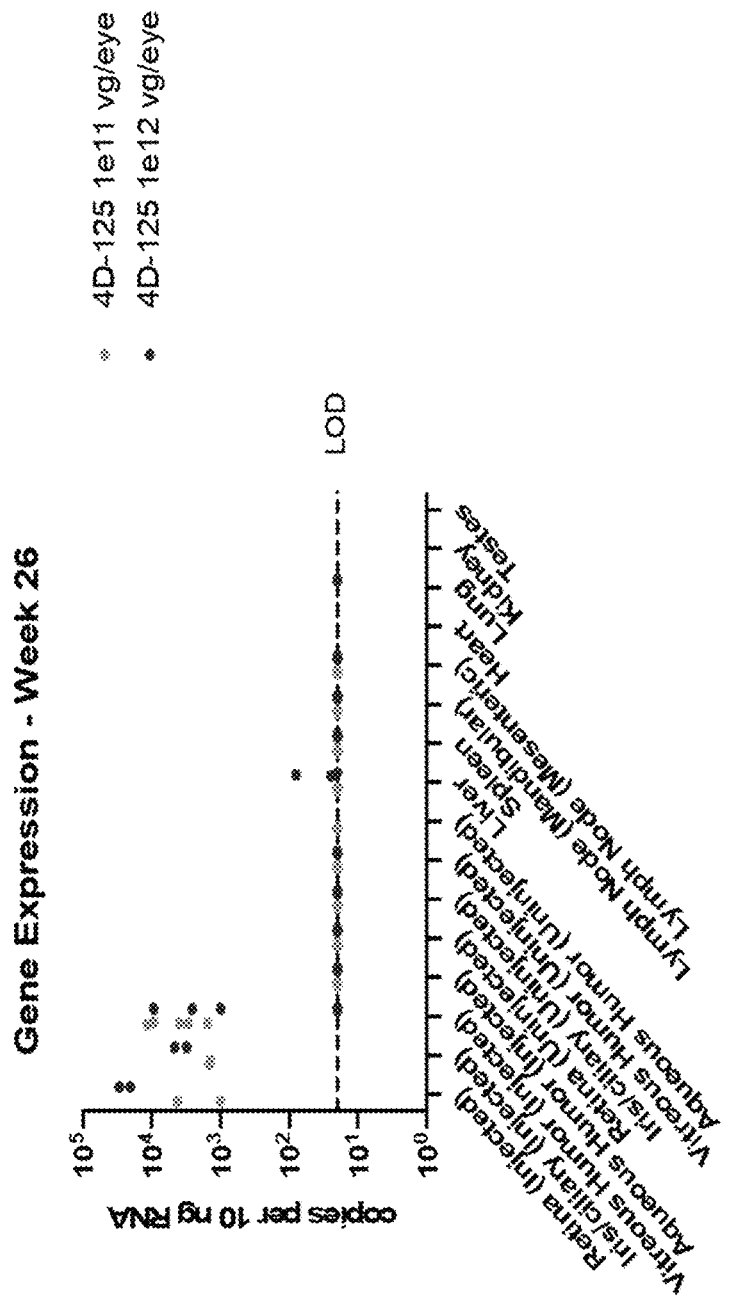

Very high levels of vector genomes were present in the retina of the treated eye at all timepoints (week 3, left panel; week 13, middle panel; week 26, right panel), indicating persistence of the vector in ocular tissue (FIG. 10). In addition to the retina, vector genomes were detected in the treated eye within samples from the aqueous humor, vitreous humor, iris/ciliary body, and the optic nerve at all timepoints. Non-ocular tissues generally had no detectable vector genomes with the exception of low levels in liver, spleen, and the lymph nodes (FIG. 10). R100 vector-derived transgene expression was detected in the treated retina and iris/ciliary body from both low and high dose groups (FIG. 11). Gene expression was dose-dependent and increased from Week 3 to Week 13 and remained stable at Week 26 (FIG. 11, left, middle and right panel respectively). No non-ocular vector expression was detected at Week 26 (FIG. 11).

Using an ELISpot assay to evaluate cellular immune responses, no animals developed significant responses to R100 capsid peptides or transgene peptides (data not shown). A majority of animals dosed with 4D-125 generated an anti-capsid antibody response post-administration (data not shown).

Summary 4D-125 (R100.GRK-cohRPGRorf15) has recently been translated into a clinical trial for the inherited retinal disease x-linked retinitis pigmentosa (NCT04517149). This therapeutic product has been evaluated in a GLP toxicology and biodistribution studies (Table 5). A total of 30 NHPs were injected with a single eye administration; a total of 30 NHP eyes were injected. No significant test-article-related adverse events or T-cell responses were reported. Mild to moderate, transient corticosteroid-responsive anterior uveitis was observed. Transgene expression was localized to the retina, and expression was not detected in any of the systemic organs evaluated. Human clinical trials are underway in order to determine the safety, pharmacodynamics, and efficacy (including through serial visual field testing and optical coherence tomography scans) of this product by intravitreal injection.

Example 5—Assessment of Safety of Codon Optimized RPGRorf15 cDNA Sequence Delivered by R100 Via Intravitreal Administration in Human X-Linked Retinitis Pigmentosa Patients Initial Phase 1 Dose Escalation Safety and Tolerability Data Summary Clinical Trial Designs and Enrollment The clinical trial employed a standard "3+3" dose-escalation designed to assess the safety, tolerability and biologic activity of a single intravitreal injection of 4D-125 at two dose levels (3E11 or 1E12 vg/eye). A total of six patients were enrolled across dose escalation cohorts, with three at each dose level. Patients received a standard immunosuppression regimen with taper; adjustments were determined by investigators. The results described are based on cut-offs between 4-9 months post-administration.

Initial Tolerability and Adverse Event Profile 4D-125 was well-tolerated throughout the assessment period as outlined in the treatment-emergent adverse event (AE) summary table (Table 6):

TABLE 6

Adverse Event Summary

| Patient # enrolled | 6 |
|---|---|
| Doses | 3E11 or 1E12 vg/eye |
| Follow-up at data cut-off (months) | 4-9 months |
| Dose-Limiting Toxicities (DLTs) | 0 (0%) |
| Serious AE | 0 (0%) |
| Any CTCAE Grade ≥ 3 | 0 (0%) |
| Retinal AE (Any Grade) | 0 (0%) |
| Uveitis CTCAE Grade 2 (moderate) | 1/6 (17%) |
| Uveitis CTCAE Grade 1 (mild) | 2/6 (33%) |

Clinical Assessments

Preliminary biological activity was assessed using microperimetry (MP) to measure retinal sensitivity and SD-OCT to measure ellipsoid zone area (EZA). Seven subjects (median age 42.5 years; range 27-56 years) received 4D-125 ($3 \times 10^{11}$ vg/eye (n=3) and $1 \times 10^{12}$ vg/eye (n=4)) with follow-up of 4.2-12.5 months. Intraocular inflammation (4/7 subjects) was mild or moderate, transient (duration 0.9-1.6 months) and steroid-responsive. Most of the subjects had advanced disease, with only 2 having both measurable EZA and mean MP retinal sensitivity (mMPRS) at baseline (BL) in both eyes and follow-up of at least 4 months. Both subjects had a greater increase from BL in mMPRS in the treated vs. untreated eye (+1.65 dB vs. +0.25 dB at 9 months and +0.50 dB vs. +0.10 dB at 4 months; BL values 1.5-3.2 dB) and number of loci gaining >7 dB sensitivity (6 vs. 1 at 9 months and 3 vs. 0 at 4 months). Relative decreases from BL EZA were less in the treated vs. untreated eye for both subjects (−12.4% vs. −16.2% at 9 months and −20.2% vs. −28.7% at 6 months).

During the Phase 1/2 study, patients' ocular and systemic status is closely monitored including detailed ophthalmic evaluations and retinal imaging together with blood testing and systemic examinations, as necessary. A variety of visual function and anatomical assessments are performed to detect any preliminary efficacy signal. These assessments include, but are not limited to, measurements of ellipsoid zone (EZ) area, fundus autofluorescence, microperimetry, static automated perimetry, and best corrected visual acuity (BCVA).

CONCLUSION

Intravitreally administered 4D-125 was well-tolerated with mild or moderate, transient, and steroid-responsive intraocular inflammation. Preliminary signs of biologic activity were observed in 2 evaluable dose escalation subjects based on microperimetry and SD-OCT. These findings support dose expansion with the $1 \times 10^{12}$ vg/eye dose in XLRP subjects with less advanced disease in the ongoing Phase 1/2 study.

While the materials and methods of this invention have been described in terms of preferred embodiments, it will be apparent to those of skill in the art that variations may be applied to the method described herein without departing from the concept, spirit and scope of the invention. All such similar substitutes and modifications apparent to those skilled in the art are deemed to be within the spirit, scope and concept of the invention.

The invention claimed is:

1. A nucleic acid encoding human retinitis pigmentosa GTPase regulator (RPGR) protein of SEQ ID NO:2 and codon optimized for expression in humans, the nucleic acid comprising the nucleotide sequence set forth as SEQ ID NO: 1 or comprising a nucleotide sequence at least 95% identical thereto, wherein the nucleic acid is expressed in a host cell at a greater level compared with the level of expression of the wild type RPGR nucleotide sequence of SEQ ID NO: 3 in the host cell under the same conditions.

2. The nucleic acid according to claim 1, wherein the nucleotide sequence has a codon adaptation index of at least 0.89.

3. The nucleic acid according to claim 1, comprising the nucleotide sequence set forth as SEQ ID NO: 1.

4. An expression cassette comprising a nucleic acid according to claim 1, wherein the nucleotide sequence set forth as SEQ ID NO: 1 or the nucleotide sequence at least 95% identical thereto is operably linked to an expression control sequence.

5. The expression cassette of claim 4, wherein the expression control sequence is a constitutive promoter or is a promoter that directs preferential expression of the nucleic acid in rod and cone cells.

6. The expression cassette of claim 5, wherein the expression control sequence is a human G protein-coupled receptor rhodopsin kinase 1 (hGRK) promoter.

7. The expression cassette of claim 6, comprising from 5' to 3': (a) an AAV2 terminal repeat (b) an hGRK promoter (c) codon optimized RPGRorf15 gene of SEQ ID NO:1 (d) an SV40 polyadenylation sequence and (e) an AAV2 terminal repeat.

8. The expression cassette of claim 7, wherein the 5' AAV2 terminal repeat has the nucleotide sequence set forth as SEQ ID NO:6 and/or wherein the hGRK promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

9. The expression cassette of claim 8, comprising or consisting of the nucleotide sequence of SEQ ID NO:5 or a sequence at least at least 95% identical thereto.

10. A recombinant adeno-associated virus (rAAV) vector comprising a heterologous nucleic acid comprising the expression cassette according to claim 4.

11. The rAAV vector of claim 10, wherein the rAAV vector comprises an AAV capsid of serotype 2, 5 or 8 or a variant thereof.

12. The rAAV vector of claim 11, wherein the rAAV vector comprises a variant AAV capsid protein comprising the amino acid sequence of SEQ ID NO:9.

13. The rAAV vector of claim 12, wherein the rAAV vector comprises a nucleic acid comprising from 5' to 3': (a) an AAV2 terminal repeat (b) an hGRK promoter (c) codon optimized RPGRorf15 gene of SEQ ID NO:1 and (d) an AAV2 terminal repeat.

14. The rAAV vector of claim 13, wherein the 5' AAV2 terminal repeat has the nucleotide sequence set forth as SEQ ID NO:6 and/or wherein the hGRK promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

15. The rAAV vector of claim 14, wherein the rAAV vector comprises a nucleic acid comprising the nucleotide sequence of SEQ ID NO:5 or a sequence at least 95% identical thereto.

16. The rAAV vector of claim 15, wherein the rAAV vector comprises (i) a capsid comprising a capsid protein comprising or consisting of the sequence of SEQ ID NO:9 and (ii) a nucleic acid comprising or consisting of the nucleotide sequence of SEQ ID NO:5.

17. A method for treating XLRP in a human subject in need thereof, comprising administering to the subject a therapeutically effective amount of pharmaceutical composition comprising an rAAV vector according to claim 13 and a pharmaceutically acceptable excipient, whereby the XLRP is treated in the human subject.

18. The method according to claim 17, wherein the 5' AAV2 terminal repeat has the nucleotide sequence set forth as SEQ ID NO:6 and/or wherein the hGRK promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

19. The method according to claim 18, wherein the rAAV vector comprises (i) a capsid comprising a capsid protein comprising or consisting of the sequence of SEQ ID NO:9 and (ii) a nucleic acid comprising or consisting of the nucleotide sequence of SEQ ID NO:5.

20. The method according to claim 19, wherein the pharmaceutical composition is administered to the subject by periocular, intravitreal, suprachoroidal or subretinal injection.

21. The method according to claim 20, wherein the vector is administered to the subject at a dosage from $10^{10}$ vector genomes (vg)/eye to $10^{13}$ vg/eye.

22. The method according to claim 21, wherein the vector is administered to the subject at a dosage from $1 \times 10^{11}$ vg/eye to $5 \times 10^{12}$ vg/eye.

23. The method according to according to claim 22, wherein the vector is administered to the subject at a dosage of $3 \times 10^{11}$ vg/eye or at a dosage of $1 \times 10^{12}$ vg/eye.

24. A pharmaceutical composition comprising an rAAV according to claim 16 and at least one pharmaceutically acceptable excipient.

25. The pharmaceutical composition according to claim 24, wherein the pharmaceutical composition comprises between $10^9$ vg and $10^{14}$ vg of the rAAV or comprises between $10^{10}$ vg and $10^{13}$ vg of the rAAV, or comprises $3 \times 10^{11}$ vg or $1 \times 10^{12}$ vg of the rAAV.

* * * * *

SEQUENCE LISTING

```
<160> NUMBER OF SEQ ID NOS: 10

<210> SEQ ID NO 1
<211> LENGTH: 3459
<212> TYPE: DNA
<213> ORGANISM: Artificial Sequence
<220> FEATURE:
<223> OTHER INFORMATION: codon-optimized RPGRorf15

<400> SEQUENCE: 1
atgagagaac ccgaggaact gatgcccgac tctggcgccg tgtttacctt cggcaagagc      60
aagttcgccg agaacaaccc cggcaagttc tggttcaaga cgacgtgcc agtgcacctg     120 agctgcggag atgaacactc tgccgtggtc accggcaaca acaagctgta catgttcggc     180
agcaacaact ggggccagct cggcctggga tctaagtctg ccatcagcaa gcctacctgc     240
gtgaaggccc tgaagcctga gaaagtgaaa ctggccgcct gcggcagaaa tcacaccctg     300
gtttctaccg aaggcggcaa tgtgtatgcc accggcggaa acaatgaggg acagcttgga     360
ctgggcgaca ccgaggaaag aaacaccttc cacgtgatca gcttttcac cagcgagcac     420 aagatcaagc agctgagcgc cggctctaat acctctgccg ctctgacaga ggacggcaga     480
ctgtttatgt ggggcgacaa ttctgagggc cagatcggac tgaagaacgt gtccaatgtg     540
tgcgtgcccc agcaagtgac aatcggcaag cctgtgtctt ggatcagctg cggctactac     600
cacagcgcct ttgtgacaac cgatggcgag ctgtatgtgt cggcgagcc agagaatggc     660 aagctgggac tgcctaacca gctgctgggc aatcacagaa cccctcagct ggtgtctgag     720
atccccgaaa aagtgatcca ggtggcctgt ggcggagagc acacagtggt gctgacagag     780
aatgccgtgt acaccttggg cctgggccag tttggacaac tcggactggg aaccttcctg     840
ttcgagacaa gcgagcccaa agtgatcgag aacatccggg accagaccat cagctacatc     900
agctgtggcg agaaccacac agccctgatc acagacatcg gcctgatgta cacattcggc     960
gacggaaggc atggaaagct cggacttggc ctggaaaact tcaccaacca cttcatccct    1020
acgctgtgca gcaacttcct gcggttcatt gtgaagctgg tggcctgcgg aggatgccac    1080
atggtggttt ttgctgcccc tcacagaggc gtggccaaag agattgagtt cgacgagatc    1140
aacgatacct gcctgagcgt ggccaccttc ctgccttaca gcagcctgac atctggcaac    1200
gtgctgcaga ggacactgag cgccagaatg cgcagacggg aaagagagag aagccccgac    1260
agcttcagca tgagaagaac cctgcctcca atcgagggca cactgggcct gtctgcctgc    1320
tttctgccta acagcgtgtt ccccagatgc agcgagagaa acctgcaaga gagcgtgctg    1380
agcgagcagg atctgatgca gcctgaggaa cccgactacc tgctggacga gatgaccaaa    1440
gaggccgaga tcgacaacag cagcacagtg gaaagcctgg gcgagacaac cgacatcctg    1500
aacatgaccc acatcatgag cctgaacagc aacgagaagt ctctgaagct gagccccgtg    1560
cagaagcaga agaagcagca gaccatcggc gagctgacac aggatactgc cctgaccgag    1620
```

|  |  |
|---|---|
| aacgacgaca gcgacgagta cgaagagatg agcgagatga aggaaggcaa ggcctgcaag | 1680 |
| cagcacgtgt cccagggcat ctttatgacc cagcctgcca ccaccatcga ggccttttcc | 1740 |
| gacgaggaag tggaaatccc cgaggaaaaa gagggcgccg aggacagcaa aggcaacggc | 1800 |
| attgaggaac aagaggtgga agccaacgaa gagaacgtga aggtgcacgg cggacgaaaa | 1860 |
| gaaaagaccg agatcctgag cgacgacctg accgataagg ccgaggtttc cgagggcaaa | 1920 |
| gccaagtctg tgggagaagc cgaggatgga cctgaaggcc gcggagatgg aacctgtgaa | 1980 |
| gaaggatcta gcggagccga gcactggcag gatgaggaac gcgagaaggg cgagaaagac | 2040 |
| aaaggcagag gcgagatgga aagacccggc gagggcgaaa aagagctggc cgagaaagag | 2100 |
| gaatggaaga acgcgacgg cgaagaacaa gagcagaaag aaagagagca gggccaccag | 2160 |
| aaagaacgga atcaagagat ggaagaaggc ggcgaggaag aacacggcga aggggaagaa | 2220 |
| gaggaaggcg accgagagga agaagaagag aaagaaggcg aaggcaaaga agaaggcgag | 2280 |
| ggcgaagagg tggaaggcga gcgtgaaaaa gaagagggcg aacgcaagaa agaagaacgc | 2340 |
| gccggaaaag aggaaaaagg cgaggaagag ggcgaccaag gcgaaggcga ggaagaagaa | 2400 |
| actgaaggca gaggggaaga gaaagaggaa ggcggcgaag tcgaaggcgg agaggttgaa | 2460 |
| gaaggcaaag cgagcgagaa agaggaagaa gaagaaggcg aaggcgagga gaggaaggc | 2520 |
| gaaggcgaag aggaagaagg cgaagggaa gaagaagaag gcgaaggcaa gggcgaagag | 2580 |
| gagggcgaag aaggcgaggg cgaagaggag ggcgaagaag gcgaaggcga gggcgaagaa | 2640 |
| gaagaaggcg aaggcgaagg cgaggaagaa ggcgaaggcg aagggaaga gaggaaggc | 2700 |
| gaaggcgaag gcgaagaaga aggcgaaggc gagggcgaag aggaagaagg cgaaggcaaa | 2760 |
| ggggaagaag aaggcgagga aggcgaaggc gaaggcgagg aagaagaagg cgaaggcgag | 2820 |
| ggcgaagatg gcgaaggcga aggcgaagag gaagagggcg agtgggaggg cgaagaagag | 2880 |
| gaaggcgaag gcgagggcga gaggaaggc gaaggcgagg gcgaagaagg cgaaggcgaa | 2940 |
| ggcgaggaag aggaaggcga aggcgaaggg gaagaagaag agggcgaaga agaaggcgaa | 3000 |
| gaggaaggcg aaggggaaga gaaaggcgaa ggcgaaggcg aagaagagga gagggcgaa | 3060 |
| gttgaaggcg aggttgaggg cgaagaaggc gaaggcgaag gggaagaaga agaaggcgag | 3120 |
| gaagaagggg aagagagaga aaaagaaggc gagggcgaag aaaaccgccg gaaccgcgaa | 3180 |
| gaggaagagg aagaagaggg caagtaccaa gagactggcg aggaagagaa cgagcggcag | 3240 |
| gatggcgaag agtacaagaa ggtgtccaag atcaagggca gcgtgaagta cggcaagcac | 3300 |
| aagacctacc agaagaagtc cgtcaccaac acgcaaggca atggaaaaga acagcggagc | 3360 |
| aagatgcccg tgcagtccaa gaggctgctg aagaatggcc ctagcggcag caagaaattc | 3420 |
| tggaacaatg tgctgcccca ctacctcgag ctgaagtga | 3459 |

<210> SEQ ID NO 2
<211> LENGTH: 1152
<212> TYPE: PRT
<213> ORGANISM: Homo sapiens

<400> SEQUENCE: 2

Met Arg Glu Pro Glu Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
                20                  25                  30

Lys Asn Asp Val Pro Val His Leu Ser Cys Gly Asp Glu His Ser Ala
            35                  40                  45

-continued

```
Val Val Thr Gly Asn Asn Lys Leu Tyr Met Phe Gly Ser Asn Asn Trp
 50                  55                  60
Gly Gln Leu Gly Leu Gly Ser Lys Ser Ala Ile Ser Lys Pro Thr Cys
 65                  70                  75                  80
Val Lys Ala Leu Lys Pro Glu Lys Val Lys Leu Ala Ala Cys Gly Arg
                 85                  90                  95
Asn His Thr Leu Val Ser Thr Glu Gly Gly Asn Val Tyr Ala Thr Gly
                100                 105                 110
Gly Asn Asn Glu Gly Gln Leu Gly Leu Gly Asp Thr Glu Glu Arg Asn
            115                 120                 125
Thr Phe His Val Ile Ser Phe Phe Thr Ser Glu His Lys Ile Lys Gln
130                 135                 140
Leu Ser Ala Gly Ser Asn Thr Ser Ala Ala Leu Thr Glu Asp Gly Arg
145                 150                 155                 160
Leu Phe Met Trp Gly Asp Asn Ser Glu Gly Gln Ile Gly Leu Lys Asn
                165                 170                 175
Val Ser Asn Val Cys Val Pro Gln Gln Val Thr Ile Gly Lys Pro Val
            180                 185                 190
Ser Trp Ile Ser Cys Gly Tyr Tyr His Ser Ala Phe Val Thr Thr Asp
        195                 200                 205
Gly Glu Leu Tyr Val Phe Gly Glu Pro Glu Asn Gly Lys Leu Gly Leu
210                 215                 220
Pro Asn Gln Leu Leu Gly Asn His Arg Thr Pro Gln Leu Val Ser Glu
225                 230                 235                 240
Ile Pro Glu Lys Val Ile Gln Val Ala Cys Gly Gly Glu His Thr Val
                245                 250                 255
Val Leu Thr Glu Asn Ala Val Tyr Thr Phe Gly Leu Gly Gln Phe Gly
            260                 265                 270
Gln Leu Gly Leu Gly Thr Phe Leu Phe Glu Thr Ser Glu Pro Lys Val
        275                 280                 285
Ile Glu Asn Ile Arg Asp Gln Thr Ile Ser Tyr Ile Ser Cys Gly Glu
290                 295                 300
Asn His Thr Ala Leu Ile Thr Asp Ile Gly Leu Met Tyr Thr Phe Gly
305                 310                 315                 320
Asp Gly Arg His Gly Lys Leu Gly Leu Gly Leu Glu Asn Phe Thr Asn
                325                 330                 335
His Phe Ile Pro Thr Leu Cys Ser Asn Phe Leu Arg Phe Ile Val Lys
            340                 345                 350
Leu Val Ala Cys Gly Gly Cys His Met Val Val Phe Ala Ala Pro His
        355                 360                 365
Arg Gly Val Ala Lys Glu Ile Glu Phe Asp Glu Ile Asn Asp Thr Cys
370                 375                 380
Leu Ser Val Ala Thr Phe Leu Pro Tyr Ser Ser Leu Thr Ser Gly Asn
385                 390                 395                 400
Val Leu Gln Arg Thr Leu Ser Ala Arg Met Arg Arg Arg Glu Arg Glu
                405                 410                 415
Arg Ser Pro Asp Ser Phe Ser Met Arg Arg Thr Leu Pro Pro Ile Glu
            420                 425                 430
Gly Thr Leu Gly Leu Ser Ala Cys Phe Leu Pro Asn Ser Val Phe Pro
        435                 440                 445
Arg Cys Ser Glu Arg Asn Leu Gln Glu Ser Val Leu Ser Glu Gln Asp
450                 455                 460
Leu Met Gln Pro Glu Glu Pro Asp Tyr Leu Leu Asp Glu Met Thr Lys
```

-continued

```
465                 470                 475                 480
Glu Ala Glu Ile Asp Asn Ser Ser Thr Val Glu Ser Leu Gly Glu Thr
                485                 490                 495
Thr Asp Ile Leu Asn Met Thr His Ile Met Ser Leu Asn Ser Asn Glu
            500                 505                 510
Lys Ser Leu Lys Leu Ser Pro Val Gln Lys Gln Lys Gln Gln Thr
        515                 520                 525
Ile Gly Glu Leu Thr Gln Asp Thr Ala Leu Thr Glu Asn Asp Asp Ser
    530                 535                 540
Asp Glu Tyr Glu Glu Met Ser Glu Met Lys Glu Gly Lys Ala Cys Lys
545                 550                 555                 560
Gln His Val Ser Gln Gly Ile Phe Met Thr Gln Pro Ala Thr Thr Ile
                565                 570                 575
Glu Ala Phe Ser Asp Glu Glu Val Glu Ile Pro Glu Glu Lys Glu Gly
            580                 585                 590
Ala Glu Asp Ser Lys Gly Asn Gly Ile Glu Glu Gln Glu Val Glu Ala
        595                 600                 605
Asn Glu Glu Asn Val Lys Val His Gly Gly Arg Lys Glu Lys Thr Glu
    610                 615                 620
Ile Leu Ser Asp Asp Leu Thr Asp Lys Ala Glu Val Ser Glu Gly Lys
625                 630                 635                 640
Ala Lys Ser Val Gly Glu Ala Asp Gly Pro Glu Gly Arg Gly Asp
                645                 650                 655
Gly Thr Cys Glu Glu Gly Ser Ser Gly Ala Glu His Trp Gln Asp Glu
            660                 665                 670
Glu Arg Glu Lys Gly Glu Lys Asp Lys Gly Arg Gly Glu Met Glu Arg
        675                 680                 685
Pro Gly Glu Gly Glu Lys Glu Leu Ala Glu Lys Glu Glu Trp Lys Lys
    690                 695                 700
Arg Asp Gly Glu Glu Gln Glu Gln Lys Glu Arg Glu Gln Gly His Gln
705                 710                 715                 720
Lys Glu Arg Asn Gln Glu Met Glu Glu Gly Glu Glu His Gly
                725                 730                 735
Glu Gly Glu Glu Glu Gly Asp Arg Glu Glu Glu Glu Lys Glu
            740                 745                 750
Gly Glu Gly Lys Glu Glu Gly Glu Gly Glu Val Glu Gly Glu Arg
        755                 760                 765
Glu Lys Glu Glu Gly Glu Arg Lys Lys Glu Arg Ala Gly Lys Glu
    770                 775                 780
Glu Lys Gly Glu Glu Gly Asp Gln Gly Glu Gly Glu Glu Glu
785                 790                 795                 800
Thr Glu Gly Arg Gly Glu Glu Lys Glu Glu Gly Glu Val Glu Gly
                805                 810                 815
Gly Glu Val Glu Glu Gly Lys Gly Glu Arg Glu Glu Glu Glu Glu
            820                 825                 830
Gly Glu Gly Glu Glu Glu Glu Gly Glu Glu Glu Glu Gly Glu
        835                 840                 845
Gly Glu Glu Glu Gly Glu Gly Lys Gly Glu Glu Glu Gly Glu Glu
    850                 855                 860
Gly Glu Gly Glu Glu Gly Glu Glu Gly Glu Gly Glu Gly Glu Glu
865                 870                 875                 880
Glu Glu Gly Glu Gly Glu Gly Glu Glu Gly Glu Gly Glu Gly Glu
                885                 890                 895
```

```
Glu Gly Glu Gly Glu Gly Glu Gly Glu Gly Glu Gly Glu Gly
        900             905             910
Glu Glu Glu Glu Gly Glu Gly Lys Gly Glu Glu Gly Glu Gly
        915             920             925
Glu Gly Glu Gly Glu Gly Glu Gly Glu Gly Glu Gly Asp Gly
        930             935             940
Glu Gly Glu Gly Glu Gly Glu Gly Glu Trp Glu Gly Glu Glu
945             950             955             960
Glu Gly Glu Gly Glu Gly Glu Gly Glu Gly Glu Gly Glu Glu
        965             970             975
Gly Glu Gly Glu Gly Glu Gly Glu Gly Glu Gly Glu Gly Glu Glu
        980             985             990
Glu Glu Gly Glu Gly Glu Gly Glu Glu Glu Gly Glu Gly Glu Glu Glu
        995             1000            1005
Gly Glu Gly Glu Gly Glu Glu Glu Glu Gly Glu Val Glu Gly
        1010            1015            1020
Glu Val Glu Gly Glu Glu Gly Glu Gly Glu Gly Glu Glu Glu
        1025            1030            1035
Gly Glu Glu Glu Gly Glu Glu Arg Glu Lys Glu Gly Glu Gly Glu
        1040            1045            1050
Glu Asn Arg Arg Asn Arg Glu Glu Glu Glu Glu Glu Gly Lys
        1055            1060            1065
Tyr Gln Glu Thr Gly Glu Glu Glu Asn Glu Arg Gln Asp Gly Glu
        1070            1075            1080
Glu Tyr Lys Lys Val Ser Lys Ile Lys Gly Ser Val Lys Tyr Gly
        1085            1090            1095
Lys His Lys Thr Tyr Gln Lys Lys Ser Val Thr Asn Thr Gln Gly
        1100            1105            1110
Asn Gly Lys Glu Gln Arg Ser Lys Met Pro Val Gln Ser Lys Arg
        1115            1120            1125
Leu Leu Lys Asn Gly Pro Ser Gly Ser Lys Lys Phe Trp Asn Asn
        1130            1135            1140
Val Leu Pro His Tyr Leu Glu Leu Lys
        1145            1150

<210> SEQ ID NO 3
<211> LENGTH: 3459
<212> TYPE: DNA
<213> ORGANISM: Homo sapiens

<400> SEQUENCE: 3
atgagggagc cggaagagct gatgcccgat tcgggtgctg tgtttacatt tgggaaaagt      60
aaatttgctg aaaataatcc cggtaaattc tggtttaaaa atgatgtccc tgtacatctt    120
tcatgtggag atgaacattc tgctgttgtt accggaaata taaactttta catgtttggc    180
agtaacaact ggggtcagtt aggattagga tcaaagtcag ccatcagcaa gccaacatgt    240
gtcaaagctc taaaacctga aaaagtgaaa ttagctgcct gtggaaggaa ccacaccctg    300
gtgtcaacag aaggaggcaa tgtatatgca actggtggaa ataatgaagg acagttgggg    360
cttggtgaca ccgaagaaag aaacactttt catgtaatta gctttttac atccgagcat    420 aagattaagc agctgtctgc tggatctaat acttcagctg ccctaactga ggatggaaga    480 cttttttatgt ggggtgacaa ttccgaaggg caaattggtt taaaaaatgt aagtaatgtc    540
tgtgtccctc agcaagtgac cattgggaaa cctgtctcct ggatctcttg tggatattac    600
```

```
cattcagctt tgtaacaac agatggtgag ctatatgtgt ttggagaacc tgagaatggg    660
aagttaggtc ttcccaatca gctcctgggc aatcacagaa caccccagct ggtgtctgaa    720
attccggaga aggtgatcca agtagcctgt ggtggagagc atactgtggt tctcacggag    780
aatgctgtgt atacctttgg gctgggacaa tttggtcagc tgggtcttgg cacttttctt    840
tttgaaactt cagaacccaa agtcattgag aatattaggg atcaaacaat aagttatatt    900
tcttgtggag aaaatcacac agctttgata acagatatcg gccttatgta tacttttgga    960
gatggtcgcc acggaaaatt aggacttgga ctggagaatt ttaccaatca cttcattcct   1020
actttgtgct ctaattttt gaggtttata gttaaattgg ttgcttgtgg tggatgtcac   1080
atggtagttt ttgctgctcc tcatcgtggt gtggcaaaag aaattgaatt cgatgaaata   1140
aatgatactt gcttatctgt ggcgactttt ctgccgtata gcagtttaac ctcaggaaat   1200
gtactgcaga ggactctatc agcacgtatg cggcgaagag agagggagag gtctccagat   1260 tcttttcaa tgaggagaac actacctcca atagaaggga ctcttggcct ttctgcttgt   1320
tttctcccca attcagtctt tccacgatgt tctgagagaa acctccaaga gagtgtctta   1380
tctgaacagg acctcatgca gccagaggaa ccagattatt tgctagatga atgaccaaa   1440 gaagcagaga tagataattc ttcaactgta gaaagccttg gagaaactac tgatatctta   1500
aacatgacac acatcatgag cctgaattcc aatgaaaagt cattaaaatt atcaccagtt   1560
cagaaacaaa agaaacaaca acaattggg gaactgacgc aggatacagc tcttactgaa   1620
aacgatgata gtgatgaata tgaagaaatg tcagaaatga agaagggaa agcatgtaaa   1680 caacatgtgt cacaagggat tttcatgacg cagccagcta cgactatcga agcattttca   1740
gatgaggaag tagagatccc agaggagaag gaaggagcag aggattcaaa aggaaatgga   1800
atagaggagc aagaggtaga agcaaatgag gaaaatgtga aggtgcatgg aggaagaaag   1860
gagaaaacag agatcctatc agatgaccct acagacaaag cagaggtgag tgaaggcaag   1920
gcaaaatcag tgggagaagc agaggatggg cctgaaggta gagggatgg aacctgtgag   1980 gaaggtagtt caggagcaga acactggcaa gatgaggaga gggagaaggg ggagaaagac   2040
aagggtagag gagaaatgga gaggccagga gagggagaga aggaactagc agagaaggaa   2100
gaatggaaga gagggatgg ggaagagcag gagcaaaagg agaggagca gggccatcag   2160 aaggaaagaa accaagagat ggaggaggga ggggaggagg agcatggaga aggagaagaa   2220
gaggagggag acagagaaga ggaagaagag aaggagggag aagggaaaga ggaaggagaa   2280
ggggaagaag tggagggaga acgtgaaaag gaggaaggag agaggaaaaa ggaggaagaa   2340 gcgggggaagg aggagaaagg aggaggaagaa ggagaccaag gagaggggga agaggaggaa   2400
acagagggga gagggaggaa aaagaggag ggagggaag tagagggagg ggaagtagag   2460
gaggggaaag agagagggga agaggaagag gaggagggtg agggggaaga ggaggaaggg   2520
gaggggaaag aggaggaagg ggaggggaa gaggaggaag gagaagggaa agggaggaa   2580 gaaggggaag aaggagaagg ggaggaagaa ggggaggaag gagaaggga gggggaagag   2640 gaggaaggag aaggggaggg agaagaggaa ggagaagggg agggagaaga ggaggaagga   2700
gaaggggagg gagaagagga aggagaaggg gagggagaag aggaggaagg agaagggaaa   2760
ggggaggagg aaggagagga agagggaagg gaggggaagg agaaggggaa   2820
ggggaggatg gagaagggga ggggaagag gaggaaggag aatggagggg ggaagaggag   2880
gaaggagaag gggaggggga agaggaagga gaagggaagg gggaggaagg agaaggggag   2940
```

| | |
|---|---|
| ggggaagagg aggaaggaga aggggagggg gaagaggagg aagggggaaga agaaggggag | 3000 |
| gaagaaggag agggagagga agaagggagg ggagaagggg aggaagaaga ggaagggga | 3060 |
| gtggaagggg aggtggaagg ggaggaagga gaggggaag gagaggaag gaaggagag | 3120 |
| gaggaaggag aagaaaggga aaaggagggg gaaggagaag aaaacaggag gaacagagaa | 3180 |
| gaggaggagg aagaagaggg gaagtatcag gagacaggcg aagaagagaa tgaaaggcag | 3240 |
| gatggagagg agtacaaaaa agtgagcaaa ataaaaggat ctgtgaaata tggcaaacat | 3300 |
| aaaacatatc aaaaaaagtc agttactaac acacagggaa atgggaaaga gcagaggtcc | 3360 |
| aaaatgccag tccagtcaaa acgacttta aaaaacgggc catcaggttc caaaaagttc | 3420 |
| tggaataatg tattaccaca ttacttggaa ttgaagtaa | 3459 |

```
<210> SEQ ID NO 4
<211> LENGTH: 199
<212> TYPE: DNA
<213> ORGANISM: Artificial Sequence
<220> FEATURE:
<223> OTHER INFORMATION: hGRK promoter

<400> SEQUENCE: 4
```

| | |
|---|---|
| gggccccaga agcctggtgg ttgtttgtcc ttctcagggg aaaagtgagg cggccccttg | 60 |
| gaggaagggg ccgggcagaa tgatctaatc ggattccaag cagctcaggg gattgtcttt | 120 |
| ttctagcacc ttccttgccac tcctaagcgt cctccgtgac cccggctggg atttagcctg | 180 |
| gtgctgtgtc agccccggg | 199 |

```
<210> SEQ ID NO 5
<211> LENGTH: 4303
<212> TYPE: DNA
<213> ORGANISM: Artificial Sequence
<220> FEATURE:
<223> OTHER INFORMATION: cohRPGR expression cassette

<400> SEQUENCE: 5
```

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctatcga ttgaattccc cggggatccg ggccccagaa | 180 |
| gcctggtggt tgtttgtcct tctcagggga aaagtgaggc ggccccttgg aggaaggggc | 240 |
| cgggcagaat gatctaatcg gattccaagc agctcagggg attgtctttt tctagcacct | 300 |
| tcttgccact cctaagcgtc ctccgtgacc ccggctggga tttagcctgg tgctgtgtca | 360 |
| gccccgggtc tagagtcgac ctgcagaagc ttccaccatg agagaacccg aggaactgat | 420 |
| gcccgactct ggcgccgtgt ttaccttcgg caagagcaag ttcgccgaga caaccccgg | 480 |
| caagttctgg ttcaagaacg acgtgccagt gcacctgagc tgcggagatg aacactctgc | 540 |
| cgtggtcacc ggcaacaaca agctgtacat gttcggcagc aacaactggg gccagctcgg | 600 |
| cctgggatct aagtctgcca tcagcaagcc tacctgcgtg aaggccctga gcctgagaa | 660 |
| agtgaaactg gccgcctgcg gcagaaatca caccctggtt tctaccgaag gcggcaatgt | 720 |
| gtatgccacc ggcggaaaca atgagggaca gcttggactg ggcgacaccg aggaaagaaa | 780 |
| caccttccac gtgatcagct ttttccaccag cgagcacaag atcaagcagc tgagcgccgg | 840 |
| ctctaatacc tctgccgctc tgacagagga cggcagactg tttatgtggg gcgacaattc | 900 |
| tgagggccag atcggactga agaacgtgtc caatgtgtgc gtgccccagc aagtgacaat | 960 |
| cggcaagcct gtgtcttgga tcagctgcgg ctactaccac agcgcctttg tgacaaccga | 1020 |

```
tggcgagctg tatgtgttcg gcgagccaga gaatggcaag ctgggactgc ctaaccagct    1080
gctgggcaat cacagaaccc ctcagctggt gtctgagatc cccgaaaaag tgatccaggt    1140
ggcctgtggc ggagagcaca cagtggtgct gacagagaat gccgtgtaca cctttggcct    1200
gggccagttt ggacaactcg gactgggaac cttcctgttc gagacaagcg agcccaaagt    1260
gatcgagaac atccgggacc agaccatcag ctacatcagc tgtggcgaga accacacagc    1320
cctgatcaca gacatcggcc tgatgtacac attcggcgac ggaaggcatg aaagctcgg     1380 acttggcctg gaaaacttca ccaaccactt catccctacg ctgtgcagca acttcctgcg    1440
gttcattgtg aagctggtgg cctgcggagg atgccacatg gtggttttg ctgcccctca     1500 cagaggcgtg gccaaagaga ttgagttcga cgagatcaac gatacctgcc tgagcgtggc    1560
caccttcctg ccttacagca gcctgacatc tggcaacgtg ctgcagagga cactgagcgc    1620
cagaatgcgc agacgggaaa gagagagaag ccccgacagc ttcagcatga agaacccct    1680 gcctccaatc gagggcacac tgggcctgtc tgcctgcttt ctgcctaaca gcgtgttccc    1740
cagatgcagc gagagaaacc tgcaagagag cgtgctgagc gagcaggatc tgatgcagcc    1800
tgaggaaccc gactacctgc tggacgagat gaccaaagag gccgagatcg acaacagcag    1860
cacagtggaa agcctgggcg agacaaccga catcctgaac atgacccaca tcatgagcct    1920
gaacagcaac gagaagtctc tgaagctgag ccccgtgcag aagcagaaga agcagcagac    1980
catcggcgag ctgacacagg atactgccct gaccgagaac gacgacagcg acgagtacga    2040
agagatgagc gagatgaagg aaggcaaggc ctgcaagcag cacgtgtccc agggcatctt    2100
tatgacccag cctgccacca ccatcgaggc cttttccgac gaggaagtgg aaatccccga    2160
ggaaaaagag ggcgccgagg acagcaaagg caacggcatt gaggaacaag aggtggaagc    2220
caacgaagag aacgtgaagg tgcacggcgg acggaaagaa aagaccgaga tcctgagcga    2280
cgacctgacc gataaggccg aggtttccga gggcaaagcc aagtctgtgg agaagccga    2340 ggatggacct gaaggccgcg gagatggaac ctgtgaagaa ggatctagcg agccgagca    2400 ctggcaggat gaggaacgcg agaagggcga gaaagacaaa ggcagaggcg agatggaaag    2460
acccggcgag ggcgaaaaag agctggccga gaaagaggaa tggaagaaac gcgacggcga    2520
agaacaagag cagaaagaaa gagagcaggg ccaccagaaa gaacggaatc aagagatgga    2580
agaaggcggc gaggaagaac acggcgaagg gaagaagag gaaggcgacc gagaggaaga    2640
agaagagaaa gaaggcgaag gcaaagaaga aggcgagggc gaagaggtgg aaggcgagcg    2700
tgaaaaagaa gagggcgaac gcaagaaaga gaacgcgcc ggaaaagagg aaaaaggcga     2760
ggaagagggc gaccaaggcg aaggcgagga agaagaaact gaaggcagag gggaagagaa    2820
agaggaaggc ggcgaagtcg aaggcggaga ggttgaagaa ggcaaaggcg agcgagaaga    2880
ggaagaagaa gaaggcgaag gcgaggaaga ggaaggcgaa ggcgaagagg aagaaggcga    2940
aggggaagaa gaagaaggcg aaggcaaggg cgaagaggag ggcgaagaag cgagggcga     3000 agaggagggc gaagaaggcg aaggcgaggg cgaagaagaa gaaggcgaag gcgaaggcga    3060
ggaagaaggc gaaggcgaag gggaagaaga ggaaggcgaa ggcgaaggcg aagaagaagg    3120
cgaaggcgag ggcgaagagg aagaaggcga aggcaaaggg gaagaagaag gcgaggaagg    3180
cgaaggcgaa ggcgaggaag aagaaggcga aggcgagggc gaagatggcg aaggcgaagg    3240
cgaagaggaa gagggcgagt gggagggcga agaagaggaa ggcgaaggcg agggcgaaga    3300
ggaaggcgaa ggcgagggcg aagaaggcga aggcgaaggc gaggaagagg aaggcgaagg    3360
```

```
cgaaggggaa gaagaagagg gcgaagaaga aggcgaagag gaaggcgaag gggaagaaga       3420
aggcgaaggc gaaggcgaag aagaggaaga gggcgaagtt gaaggcgagg ttgagggcga       3480
agaaggcgaa ggcgaagggg aagaagaaga aggcgaggaa gaaggggaag agagagaaaa       3540
agaaggcgag ggcgaagaaa accgccggaa ccgcgaagag gaagaggaag aagagggcaa       3600
gtaccaagag actggcgagg aagagaacga gcggcaggat ggcgaagagt acaagaaggt       3660
gtccaagatc aagggcagcg tgaagtacgg caagcacaag acctaccaga agaagtccgt       3720
caccaacacg caaggcaatg aaaagaaca gcggagcaag atgcccgtgc agtccaagag        3780
gctgctgaag aatggcccta gcggcagcaa gaaattctgg aacaatgtgc tgccccacta       3840
cctcgagctg aagtgagcct cgagcagcgc tgctcgagag atctgcggcc gcgagctcgg       3900
ggatccagac atgataagat acattgatga gtttggacaa accacaacta gaatgcagtg       3960
aaaaaaatgc tttatttgtg aaatttgtga tgctattgct ttatttgtaa ccattataag       4020
ctgcaataaa caagttaaca acaacaattg cattcatttt atgtttcagg ttcaggggga       4080
ggtgtgggag gttttttaaa gcaagtaaaa cctctacaaa tgtggtatgg ctgattatga       4140
tcaatgcatc ctagccggag gaaccccctag tgatggagtt ggccactccc tctctgcgcg       4200
ctcgctcgct cactgaggcc gcccgggcaa agcccgggcg tcgggcgacc tttggtcgcc       4260
cggcctcagt gagcgagcga gcgcgcagag agggagtggc caa                        4303

<210> SEQ ID NO 6
<211> LENGTH: 145
<212> TYPE: DNA
<213> ORGANISM: adeno-associated virus 2

<400> SEQUENCE: 6
ttggccactc cctctctgcg cgctcgctcg ctcactgagg ccgggcgacc aaaggtcgcc        60
cgacgcccgg gctttgcccg gcggcctcag tgagcgagc gagcgcgcag agagggagtg       120
gccaactcca tcactagggg ttcct                                             145

<210> SEQ ID NO 7
<211> LENGTH: 145
<212> TYPE: DNA
<213> ORGANISM: adeno-associated virus 2

<400> SEQUENCE: 7
aggaacccct agtgatggag ttggccactc cctctctgcg cgctcgctcg ctcactgagg        60
ccgcccgggc aaagcccggg cgtcgggcga cctttggtcg cccggcctca gtgagcgagc       120
gagcgcgcag agagggagtg gccaa                                             145

<210> SEQ ID NO 8
<211> LENGTH: 245
<212> TYPE: DNA
<213> ORGANISM: Artificial Sequence
<220> FEATURE:
<223> OTHER INFORMATION: SV40 polyadenylation sequence

<400> SEQUENCE: 8
ggggatccag acatgataag atacattgat gagtttggac aaaccacaac tagaatgcag        60
tgaaaaaaat gctttatttg tgaaatttgt gatgctattg ctttatttgt aaccattata       120
agctgcaata acaagttaa caacaacaat tgcattcatt ttatgtttca ggttcagggg       180
gaggtgtggg aggttttttt aaagcaagta aaacctctac aatgtggtat ggctgattat       240
gatca                                                                   245
```

<210> SEQ ID NO 9
<211> LENGTH: 745
<212> TYPE: PRT
<213> ORGANISM: Artificial Sequence
<220> FEATURE:
<223> OTHER INFORMATION: rAAV variant capsid protein

<400> SEQUENCE: 9

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Ala Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365
```

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Ile Ser Asp
            580                 585                 590

Gln Thr Lys His Ala Arg Gln Ala Thr Ala Asp Val Asn Thr Gln
        595                 600                 605

Gly Val Leu Pro Gly Met Val Trp Gln Asp Arg Asp Val Tyr Leu Gln
    610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
                645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
        675                 680                 685

Ser Val Glu Ile Glu Trp Glu Leu Gln Lys Glu Asn Ser Lys Arg Trp
    690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745

<210> SEQ ID NO 10
<211> LENGTH: 3459
<212> TYPE: DNA
<213> ORGANISM: Artificial Sequence
<220> FEATURE:

<223> OTHER INFORMATION: codon optimized human RPGR

<400> SEQUENCE: 10

```
atgagagagc ctgaagagct gatgcctgat agcggagcag tgtttacctt tgggaagagc      60
aagttcgcag agaataaccc tgggaaattc tggtttaaga cgacgtgcc cgtgcacctg      120
agctgtggcg atgagcactc cgccgtggtg acaggcaaca ataagctgta catgttcggc    180
tctaacaatt ggggacagct gggcctggga agcaagtccg ccatcagcaa gccaacctgc    240
gtgaaggccc tgaagcccga aaggtgaag ctggccgcct gtggcagaaa ccacacactg     300
gtgagcaccg agggaggaaa cgtgtacgca caggaggca acaatgaagg ccagctgggc     360
ctgggcgaca cagaggagag gaatacccttt cacgtgatca gcttctttac ctccgagcac   420
aagatcaagc agctgtccgc cggctctaac acaagcgccg ccctgaccga ggacggccgc    480
ctgttcatgt ggggcgataa tagcgagggc cagatcggcc tgaagaacgt gtccaacgtg    540
tgcgtgcctc agcaggtgac catcggcaag ccagtgtcct ggatctcttg tggctactat    600
cacagcgcct tcgtgaccac agatggcgag ctgtacgtgt ttggagagcc agagaacggc    660
aagctgggcc tgcctaacca gctgctgggc aatcaccgga caccccagct ggtgtccgag    720
atccctgaga aagtgatcca ggtggcatgc ggaggagagc acacagtggt gctgaccgag    780
aatgccgtgt ataccttcgg cctgggacag ttgacagcg tgggcctggg cacattcctg    840
tttgagacaa gcagccaaaa agtgatcgag aacatccgcg accagacaat cagctacatc    900
tcctgcggcg agaatcacac agccctgatc accgacatcg gcctgatgta cctttggc     960
gatgccggc acggcaagct gggcctgggc ctggagaact tcacaaatca ctttatcccc    1020
accctgtgct ctaacttcct gcggttcatc gtgaagctgg tggcctgcgg cggctgtcac    1080
atggtggtgt tcgcagcacc tcacagggga gtggccaagg agatcgagtt tgacgagatc    1140
aacgatacat gcctgtccgt ggccaccttc ctgccataca gctccctgac atccggcaat    1200
gtgctgcagc gcaccctgtc tgccaggatg cggagaaggg agaggagcg tcccctgac      1260
tctttcagca tgaggcggac actgccacct atcgagggca ccctgggcct gtctgcctgc    1320
ttcctgccta cagcgtgtt ccaagatgt agcgagagga tctgcagga gtctgtgctg       1380
agcgagcagg atctgatgca gccagaggag cccgactacc tgctggatga gatgacaaag    1440
gaggccgaga tcgacaactc tagcaccgtg gagagcctgg gcgagacaac agatatcctg    1500
aatatgacac acatcatgtc cctgaactct aatgagaagt ctctgaagct gagcccagtg    1560
cagaagcaga gaagcagca gaccatcggc gagctgaccc aggacacagc cctgaccgag    1620
aacgacgatt ctgatgagta tgaggagatg agcgagatga aggagggcaa ggcctgtaag    1680
cagcacgtgt cccagggcat cttcatgacc cagccagcca ccacaatcga ggccttttct    1740
gacgaagagg tggagatccc cgaggagaag gaggcgccg aggatagcaa gggcaatggc    1800
atcgaggagc aggaggtgga ggccaacgag gagaatgtga aggtgcacgg cggcagaaag    1860
gagaagacag agatcctgtc cgacgatctg accgacaagg ccgaggtgtc cgagggcaag    1920
gccaagtctg tgggagaggc agaggacgga ccagagggac gcggcgatgg aacctgcgag    1980
gagggatcct ctggagcaga gcactggcag gacgaagaaa gagagaaggg cgagaaggat    2040
aagggcagag gagagatgga gaggcctgga gagggagaga aggagctggc agagaaggag    2100
gagtggaaga gagggacgg cgaggagcag gagcagaagg agagagagca gggccaccag    2160
aaggagagga accaggagat ggaggaggga ggagaggagg agcacggcga gggagaggag    2220
gaggagggcg atagagagga agaagaggag aaggagggag agggcaagga ggaaggcgag    2280
```

```
                                                       -continued
ggagaggagg tggagggaga aagggagaag gaggagggag agcgcaagaa ggaagaaaga     2340
gcaggcaagg aagagaaggg agaggaggag ggcgatcagg gcgaaggaga ggaggaggag     2400
acagagggaa ggggagagga gaaggaggag ggaggagagg tcgaaggagg agaagtggag     2460
gagggcaagg gcgaaagaga agaggaggag gaggaaggcg agggcgaaga agaggagggc     2520
gagggcgagg aagaagaggg cgagggcgaa gaggaagaag gcgagggcaa gggcgaggag     2580
gagggcgaag aaggcgaagg ggaggaggag ggcgaagagg gagagggcga gggcgaggag     2640
gaagaaggcg aaggcgaagg cgaagaagaa ggagaaggag agggcgaaga ggaggaaggc     2700
gaaggagaag gagaggagga aggagaaggg gagggcgaag aggaggaggg agaaggcaag     2760
ggagaagaag aaggcgaaga aggcgaggga gaaggcgagg aagaagaagg cgagggagag     2820
ggagaggacg gcgaaggcga gggcgaggaa gaggaaggag agtgggaggg cgaggaagag     2880
gagggagaag gagaaggcga agaagaaggg gaaggagagg gcgaggaagg agaaggcgaa     2940
ggcgaagagg aggagggga aggggagggc gaggaggaag agggagaaga ggaaggcgaa     3000
gaagagggag aaggcgaaga ggaaggagaa ggcgagggag aagaagagga ggagggcgag     3060
gtcgaaggcg aggtggaggg cgaagagggg gaaggcgaag gcgaggagga ggaaggggaa     3120
gaagaaggcg aggagagaga gaaagaaggc gagggcgagg agaacagaag gaatcgcgaa     3180
gaagaagagg aagaagaggg caagtaccag gagacaggcg aggaggagaa cgagcggcag     3240
gatggcgagg agtataagaa ggtgtccaag atcaagggct ctgtgaagta cggcaagcac     3300
aagacctatc agaagaagag cgtgaccaac acacagggca atggcaagga gcagcgcagc     3360
aagatgcctg tgcagtccaa gcggctgctg aagaatggcc cctctgggag caagaagttt     3420
tggaataatg tcctgccaca ctacctggag ctgaaatga                           3459
```